(12) United States Patent
Chaddock et al.

(10) Patent No.: US 10,704,038 B2
(45) Date of Patent: Jul. 7, 2020

(54) THERAPEUTIC FUSION PROTEINS

(71) Applicant: Ipsen Bioinnovation Limited, Abingdon, Oxfordshire (GB)

(72) Inventors: John Chaddock, Abingdon (GB); Elaine Harper, Abingdon (GB)

(73) Assignee: IPSEN BIOINNOVATION LIMTIED, Abingdon (GB)

( * ) Notice: Subject to any disclaimer, the term of this patent is extended or adjusted under 35 U.S.C. 154(b) by 0 days.

(21) Appl. No.: 16/105,203

(22) Filed: Aug. 20, 2018

(65) Prior Publication Data
US 2019/0062721 A1 Feb. 28, 2019

Related U.S. Application Data

(62) Division of application No. 14/117,286, filed as application No. PCT/GB2012/051104 on May 16, 2012, now Pat. No. 10,081,803.

(30) Foreign Application Priority Data

May 16, 2011 (GB) .................................. 1108108.0

(51) Int. Cl.
| | |
|---|---|
| C12N 9/12 | (2006.01) |
| C12N 9/88 | (2006.01) |
| C12N 1/20 | (2006.01) |
| C12N 15/00 | (2006.01) |
| C12P 21/04 | (2006.01) |
| C12P 21/06 | (2006.01) |
| C07H 21/04 | (2006.01) |
| A61K 38/43 | (2006.01) |
| C07K 1/00 | (2006.01) |
| C12N 9/96 | (2006.01) |
| C07K 7/18 | (2006.01) |
| C07K 7/23 | (2006.01) |
| C07K 14/575 | (2006.01) |
| C12N 9/52 | (2006.01) |
| C12N 15/62 | (2006.01) |
| C07K 14/60 | (2006.01) |
| C12N 9/50 | (2006.01) |
| A61K 38/00 | (2006.01) |

(52) U.S. Cl.
CPC .................. *C12N 9/96* (2013.01); *C07K 7/18* (2013.01); *C07K 7/23* (2013.01); *C07K 14/575* (2013.01); *C07K 14/57572* (2013.01); *C07K 14/60* (2013.01); *C12N 9/50* (2013.01); *C12N 9/52* (2013.01); *C12N 15/62* (2013.01); *A61K 38/00* (2013.01); *C07K 2319/00* (2013.01); *C07K 2319/06* (2013.01); *C07K 2319/21* (2013.01); *C07K 2319/50* (2013.01); *C07K 2319/74* (2013.01)

(58) Field of Classification Search
None
See application file for complete search history.

(56) References Cited

U.S. PATENT DOCUMENTS

| | | |
|---|---|---|
| 5,843,446 A | 12/1998 | Ladd et al. |
| 7,452,543 B2 | 11/2008 | Chaddock et al. |
| 7,658,933 B2 * | 2/2010 | Foster .................. A61K 31/711 424/239.1 |
| 7,659,092 B2 | 2/2010 | Foster et al. |
| 8,399,400 B2 | 3/2013 | Foster et al. |
| 8,940,870 B2 | 1/2015 | Foster et al. |
| 2006/0024331 A1 | 2/2006 | Fernandez-Salas et al. |
| 2006/0211619 A1 | 9/2006 | Steward et al. |
| 2008/0187960 A1 | 8/2008 | Foster et al. |
| 2009/0048431 A1 | 2/2009 | Steward et al. |

FOREIGN PATENT DOCUMENTS

| | | |
|---|---|---|
| WO | 9807864 A1 | 2/1998 |
| WO | 2005023309 A2 | 3/2005 |
| WO | 2006059093 A2 | 6/2006 |
| WO | 2007106799 A2 | 9/2007 |
| WO | 2007138339 A2 | 12/2007 |
| WO | 2008105901 A2 | 9/2008 |
| WO | 2009150469 | 12/2009 |
| WO | 2010094905 A1 | 8/2010 |

OTHER PUBLICATIONS

Shimohigashi et al., J. Biol. Chem. 271:23642-23645 (1996).

* cited by examiner

*Primary Examiner* — Yong D Pak
(74) *Attorney, Agent, or Firm* — Gene J. Yao; Barnes & Thornburg LLP

(57) ABSTRACT

The present invention relates to the construction of a new class of Targeted Secretion Inhibitors (TSIs), which comprise a non-cytotoxic protease, translocation peptide and a targeting moiety peptide, wherein the targeting moiety peptide has a free N-terminal domain and a free C-terminal domain; to a single-chain fusion protein precursor thereof, and to a method of activating said single-chain fusion protein precursor.

19 Claims, 1 Drawing Sheet
Specification includes a Sequence Listing.

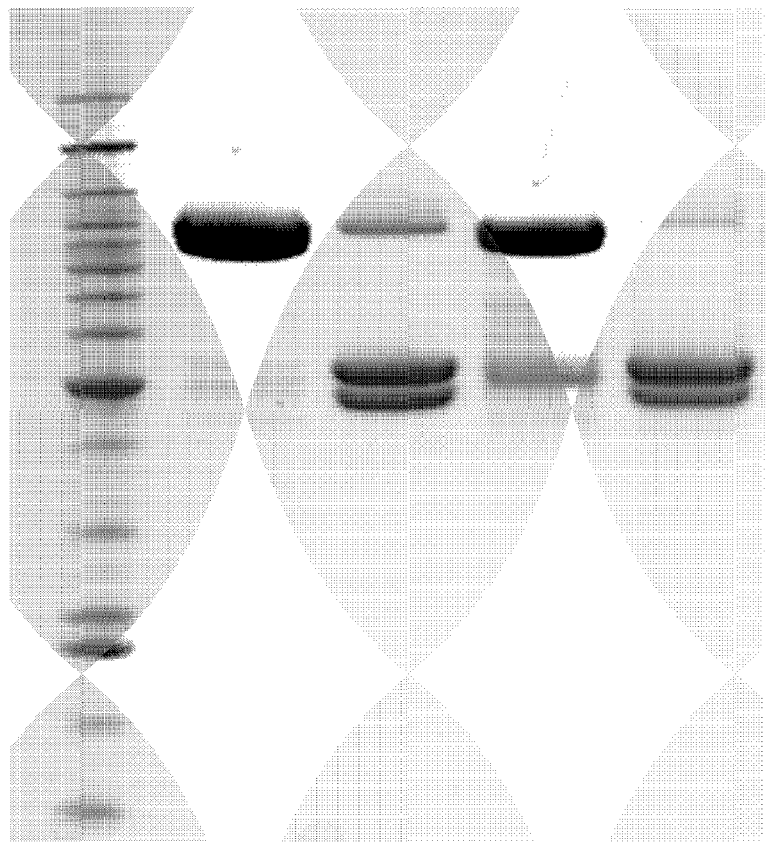

SEQUENCE LISTING

<160> NUMBER OF SEQ ID NOS: 54

<210> SEQ ID NO 1
<211> LENGTH: 2769
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 1

```
atgcatcacc atcaccatca ccatcaccat catgggagct cgaacaataa caacaataac    60
aataacaata acgatccat  gacgtggcca gttaaggatt tcaactactc agatcctgta   120
aatgacaacg atattctgta ccttcgcatt ccacaaaata aactgatcac cacaccagtc   180
aaagcattca tgattactca aaacatttgg gtcattccag aacgcttttc tagtgacaca   240
aatccgagtt tatctaaacc tccgcgtccg acgtccaaat atcagagcta ttacgatccc   300
tcatatctca gtacggacga acaaaaagat actttcctta aggtatcat  taaactgttt   360
aagcgtatta atgagcgcga tatcgggaaa aagttgatta attatcttgt tgtgggttcc   420
ccgttcatgg gcgatagctc tacccccgaa gacactttg  attttacccg tcatacgaca   480
aacatcgcgg tagagaagtt tgagaacgga tcgtggaaag tcacaaacat cattacacct   540
agcgtcttaa tttttggtcc gctgccaaac atcttagatt atacagccag cctgactttg   600
caggggcaac agtcgaatcc gagtttcgaa ggttttggta ccctgagcat tctgaaagtt   660
gccccggaat ttctgctcac ttttttcagat gtcaccagca accagagctc agcagtatta   720
ggaaagtcaa ttttttgcat ggacccggtt attgcactga tgcacgaact gacgcactct   780
ctgcatcaac tgtatgggat caacatcccc agtgacaaac gtattcgtcc ccaggtgtct   840
gaaggatttt tctcacagga tgggccgaac gtccagttcg aagagttgta ctttcgga    900
ggcctggacg tagagatcat tccccagatt gagcgcagtc agctgcgtga aaggcattg    960
ggccattata aggatattgc aaaacgcctg aataacatta acaaaacgat ccatcttcg  1020
tggatctcga atattgataa atataagaaa atttttagcg agaaatataa ttttgataaa  1080
gataatacag gtaactttgt ggttaacatt gacaaattca actcccttta cagtgatttg  1140
acgaatgtaa tgagcgaagt tgtgtatagt tcccaataca acgttaagaa tcgtacccat  1200
tacttctctc gtcactacct gccggttttc gcgaacatcc ttgacgataa tatttacact  1260
attcgtgacg gctttaactt gaccaacaag ggcttcaata ttgaaaattc aggccagaac  1320
attgaacgca ccccggcctt gcagaaactg tcgagtgaat ccgtggttga cctgtttacc  1380
aaagtctgcg tcgacggcat cattacctcc aaaactaaat ctctgataga aggtagaaac  1440
aaagcgctga acctgcagtg tattaaagtg aaaaacaatc ggctgcctta tgtagcagat  1500
aaagatagca ttagtcagga gattttcgaa aataaaatta tcactgacga accaatgtt   1560
cagaattatt cagataaatt ttcactggac gaaagcatct tagatggcca agttccgatt  1620
aacccggaaa ttgttgatcc gttactgccg aacgtgaata tggaaccgtt aaacctccct  1680
ggcgaagaga tcgtattta  tgatgacatt acgaaatatg tggactacct taattcttat  1740
tactatttgg aaagccagaa actgtccaat aacgtggaaa acattactct gaccacaagc  1800
gtggaagagg cttaggcta  ctcaaataag atttatacct tcctcccgtc gctggcggaa  1860
aaagtaaata aggtgtgca  ggctggtctg ttcctcaact gggcgaatga agttgtcgaa  1920
gactttacca cgaatattat gaaaaaggat accctggata aaatctccga cgtctcggtt  1980
attatcccat atattggccc tgcgttaaat atcggtaata gtgcgctgcg ggggaatttt  2040
aaccaggcct tgctaccgc  gggcgtcgcg ttcctcctgg agggctttcc tgaatttact  2100
atcccggcgc tcggtgtttt tacatttac  tcttccatcc aggagcgtga aaaattatc   2160
aaaaccatcg aaaactgcct ggagcagcgg gtgaaacgct ggaaagattc ttatcaatgg  2220
```

```
atggtgtcaa actggttatc tcgcatcacg acccaattca accatattaa ttaccagatg    2280
tatgatagtc tgtcgtacca agctgacgcc attaaagcca aaattgatct ggaatataaa    2340
aagtactctg gtagcgataa ggagaacatc aaaagccagg tggagaacct taagaatagt    2400
ctggatgtga aaatctctga agctatgaat aacattaaca aattcattcg tgaatgttcg    2460
gtgacgtacc tgttcaagaa tatgctgcca aaagttattg atgaactgaa taaatttgat    2520
ctgcgtacca aaaccgaact tatcaacctc atcgactccc acaacattat ccttgtgggc    2580
gaagtggatc gtctgaaggc caaagtaaac gagagctttg aaaatacgat gccgtttaat    2640
attttttcat ataccaataa ctccttgctg aaagatatca tcaatgaata tttcaatcta    2700
gaatgtggcg gtggcggtag catcgaaggt cgtcagcact ggtcctattg cctgcgccct    2760
ggttgataa                                                            2769
```

<210> SEQ ID NO 2
<211> LENGTH: 921
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met His His His His His His His His His Gly Ser Ser Asn Asn
1               5                   10                  15

Asn Asn Asn Asn Asn Asn Asn Asn Gly Ser Met Thr Trp Pro Val Lys
            20                  25                  30

Asp Phe Asn Tyr Ser Asp Pro Val Asn Asp Asn Asp Ile Leu Tyr Leu
        35                  40                  45

Arg Ile Pro Gln Asn Lys Leu Ile Thr Thr Pro Val Lys Ala Phe Met
    50                  55                  60

Ile Thr Gln Asn Ile Trp Val Ile Pro Glu Arg Phe Ser Ser Asp Thr
65                  70                  75                  80

Asn Pro Ser Leu Ser Lys Pro Pro Arg Pro Thr Ser Lys Tyr Gln Ser
                85                  90                  95

Tyr Tyr Asp Pro Ser Tyr Leu Ser Thr Asp Glu Gln Lys Asp Thr Phe
            100                 105                 110

Leu Lys Gly Ile Ile Lys Leu Phe Lys Arg Ile Asn Glu Arg Asp Ile
        115                 120                 125

Gly Lys Lys Leu Ile Asn Tyr Leu Val Val Gly Ser Pro Phe Met Gly
    130                 135                 140

Asp Ser Ser Thr Pro Glu Asp Thr Phe Asp Phe Thr Arg His Thr Thr
145                 150                 155                 160

Asn Ile Ala Val Glu Lys Phe Glu Asn Gly Ser Trp Lys Val Thr Asn
                165                 170                 175

Ile Ile Thr Pro Ser Val Leu Ile Phe Gly Pro Leu Pro Asn Ile Leu
            180                 185                 190

Asp Tyr Thr Ala Ser Leu Thr Leu Gln Gly Gln Gln Ser Asn Pro Ser
        195                 200                 205

Phe Glu Gly Phe Gly Thr Leu Ser Ile Leu Lys Val Ala Pro Glu Phe
    210                 215                 220

Leu Leu Thr Phe Ser Asp Val Thr Ser Asn Gln Ser Ser Ala Val Leu
225                 230                 235                 240

Gly Lys Ser Ile Phe Cys Met Asp Pro Val Ile Ala Leu Met His Glu
                245                 250                 255
```

```
Leu Thr His Ser Leu His Gln Leu Tyr Gly Ile Asn Ile Pro Ser Asp
            260                 265                 270

Lys Arg Ile Arg Pro Gln Val Ser Glu Gly Phe Phe Ser Gln Asp Gly
        275                 280                 285

Pro Asn Val Gln Phe Glu Glu Leu Tyr Thr Phe Gly Gly Leu Asp Val
    290                 295                 300

Glu Ile Ile Pro Gln Ile Glu Arg Ser Gln Leu Arg Glu Lys Ala Leu
305                 310                 315                 320

Gly His Tyr Lys Asp Ile Ala Lys Arg Leu Asn Asn Ile Asn Lys Thr
            325                 330                 335

Ile Pro Ser Ser Trp Ile Ser Asn Ile Asp Lys Tyr Lys Lys Ile Phe
            340                 345                 350

Ser Glu Lys Tyr Asn Phe Asp Lys Asp Asn Thr Gly Asn Phe Val Val
            355                 360                 365

Asn Ile Asp Lys Phe Asn Ser Leu Tyr Ser Asp Leu Thr Asn Val Met
        370                 375                 380

Ser Glu Val Val Tyr Ser Ser Gln Tyr Asn Val Lys Asn Arg Thr His
385                 390                 395                 400

Tyr Phe Ser Arg His Tyr Leu Pro Val Phe Ala Asn Ile Leu Asp Asp
            405                 410                 415

Asn Ile Tyr Thr Ile Arg Asp Gly Phe Asn Leu Thr Asn Lys Gly Phe
            420                 425                 430

Asn Ile Glu Asn Ser Gly Gln Asn Ile Glu Arg Asn Pro Ala Leu Gln
        435                 440                 445

Lys Leu Ser Ser Glu Ser Val Val Asp Leu Phe Thr Lys Val Cys Val
    450                 455                 460

Asp Gly Ile Ile Thr Ser Lys Thr Lys Ser Leu Ile Glu Gly Arg Asn
465                 470                 475                 480

Lys Ala Leu Asn Leu Gln Cys Ile Lys Val Lys Asn Asn Arg Leu Pro
            485                 490                 495

Tyr Val Ala Asp Lys Asp Ser Ile Ser Gln Glu Ile Phe Glu Asn Lys
            500                 505                 510

Ile Ile Thr Asp Glu Thr Asn Val Gln Asn Tyr Ser Asp Lys Phe Ser
        515                 520                 525

Leu Asp Glu Ser Ile Leu Asp Gly Gln Val Pro Ile Asn Pro Glu Ile
    530                 535                 540

Val Asp Pro Leu Leu Pro Asn Val Asn Met Glu Pro Leu Asn Leu Pro
545                 550                 555                 560

Gly Glu Glu Ile Val Phe Tyr Asp Asp Ile Thr Lys Tyr Val Asp Tyr
            565                 570                 575

Leu Asn Ser Tyr Tyr Tyr Leu Glu Ser Gln Lys Leu Ser Asn Asn Val
            580                 585                 590

Glu Asn Ile Thr Leu Thr Thr Ser Val Glu Glu Ala Leu Gly Tyr Ser
        595                 600                 605

Asn Lys Ile Tyr Thr Phe Leu Pro Ser Leu Ala Glu Lys Val Asn Lys
    610                 615                 620

Gly Val Gln Ala Gly Leu Phe Leu Asn Trp Ala Asn Glu Val Val Glu
625                 630                 635                 640

Asp Phe Thr Thr Asn Ile Met Lys Lys Asp Thr Leu Asp Lys Ile Ser
            645                 650                 655

Asp Val Ser Val Ile Ile Pro Tyr Ile Gly Pro Ala Leu Asn Ile Gly
            660                 665                 670

Asn Ser Ala Leu Arg Gly Asn Phe Asn Gln Ala Phe Ala Thr Ala Gly
```

```
                675                 680                 685
Val Ala Phe Leu Leu Glu Gly Phe Pro Glu Phe Thr Ile Pro Ala Leu
    690                 695                 700

Gly Val Phe Thr Phe Tyr Ser Ser Ile Gln Glu Arg Glu Lys Ile Ile
705                 710                 715                 720

Lys Thr Ile Glu Asn Cys Leu Glu Gln Arg Val Lys Arg Trp Lys Asp
                725                 730                 735

Ser Tyr Gln Trp Met Val Ser Asn Trp Leu Ser Arg Ile Thr Thr Gln
            740                 745                 750

Phe Asn His Ile Asn Tyr Gln Met Tyr Asp Ser Leu Ser Tyr Gln Ala
        755                 760                 765

Asp Ala Ile Lys Ala Lys Ile Asp Leu Glu Tyr Lys Lys Tyr Ser Gly
    770                 775                 780

Ser Asp Lys Glu Asn Ile Lys Ser Gln Val Glu Asn Leu Lys Asn Ser
785                 790                 795                 800

Leu Asp Val Lys Ile Ser Glu Ala Met Asn Asn Ile Asn Lys Phe Ile
                805                 810                 815

Arg Glu Cys Ser Val Thr Tyr Leu Phe Lys Asn Met Leu Pro Lys Val
            820                 825                 830

Ile Asp Glu Leu Asn Lys Phe Asp Leu Arg Thr Lys Thr Glu Leu Ile
        835                 840                 845

Asn Leu Ile Asp Ser His Asn Ile Ile Leu Val Gly Glu Val Asp Arg
    850                 855                 860

Leu Lys Ala Lys Val Asn Glu Ser Phe Glu Asn Thr Met Pro Phe Asn
865                 870                 875                 880

Ile Phe Ser Tyr Thr Asn Asn Ser Leu Leu Lys Asp Ile Ile Asn Glu
                885                 890                 895

Tyr Phe Asn Leu Glu Cys Gly Gly Gly Ser Ile Glu Gly Arg Gln
            900                 905                 910

His Trp Ser Tyr Cys Leu Arg Pro Gly
        915                 920

<210> SEQ ID NO 3
<211> LENGTH: 2739
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgcatcacc atcaccatca ccatcaccat catgggagct cgaacaataa caacaataac      60
aataacaata acgatccat ggagttcgtt aacaaacagt tcaactataa agacccagtt     120
aacggtgttg acattgctta catcaaaatc ccgaacgctg ccagatgca gccggtaaag     180 gcattcaaaa tccacaacaa atctggggtt atcccggaac gtgataccet tactaaccceg     240 gaagaaggtg acctgaaccc gccaccggaa gcgaaacagg tgccggtatc ttactatgac     300
tccacctacc tgtctaccga taacgaaaag acaactacc tgaaaggtgt tactaaactg     360
ttcgagcgta tttactccac cgacctgggc cgtatgctgc tgactagcat cgttcgcggt     420
atcccgttct gggcggttc taccatcgat accgaactga agtaatcga cactaactgc     480 atcaacgtta ttcagccgga cggttcctat cgttccgaag aactgaacct ggtgatcatc     540 ggccgtctg ctgatatcat ccagttcgag tgtaagagc ttggtcacga agttctgaac     600
ctcacccgta acggctacgg ttccactcag tacatccgtt ctctccggga cttcaccttc     660
```

```
ggttttgaag aatccctgga agtagacacg aacccactgc tgggcgctgg taaattcgca    720
actgatcctg cggttaccct ggctcacgaa ctgattcatg caggccaccg cctgtacggt    780
atcgccatca atccgaaccg tgtcttcaaa gttaacacca acgcgtatta cgagatgtcc    840
ggtctggaag ttagcttcga agaactgcgt acttttggcg tcacgacgc taaattcatc    900 gactctctgc aagaaaacga gttccgtctg tactactata acaagttcaa agatatcgca    960
tccaccctga caaagcgaa atccatcgtg ggtaccactc cttctctcca gtacatgaag   1020
aacgttttta agaaaaata cctgctcagc gaagacacct ccggcaaatt ctctgtagac   1080
aagttgaaat tcgataaact ttacaaaatg ctgactgaaa tttacaccga agacaacttc   1140
gttaagttct ttaaagttct gaaccgcaaa acctatctga acttcgacaa ggcagtattc   1200
aaaatcaaca tcgtgccgaa agttaactac actatctacg atggtttcaa cctgcgtaac   1260
accaacctgg ctgctaattt taacggccag aacacggaaa tcaacaacat gaacttcaca   1320
aaactgaaaa acttcactgg tctgttcgag ttttacaagc tgctgtgcgt cgacggcatc   1380
attacctcca aaactaaatc tctgatagaa ggtagaaaca aagcgctgaa cgacctctgt   1440
atcaaggtta caactggga tttattcttc agcccgagtg aagacaactt caccaacgac   1500
ctgaacaaag gtgaagaaat cacctcagat actaacatcg aagcagccga agaaaacatc   1560
tcgctggacc tgatccagca gtactacctg acctttaatt tcgacaacga gccggaaaac   1620
atttctatcg aaaacctgag ctctgatatc atcggccagc tggaactgat gccgaacatc   1680
gaacgttttc caaacggtaa aaagtacgag ctggacaaat ataccatgtt ccactacctg   1740
cgcgcgcagg aatttgaaca cggcaaatcc cgtatcgcac tgactaactc cgttaacgaa   1800
gctctgctca acccgtcccg tgtatacacc ttcttctcta gcgactacgt gaaaaaggtc   1860
aacaaagcga ctgaagctgc aatgttcttg ggttgggttg aacagcttgt ttatgatttt   1920
accgacgaga cgtccgaagt atctactacc gacaaaattg cggatatcac tatcatcatc   1980
ccgtacatcg gtccggctct gaacattggc aacatgctgt acaaagacga cttcgttggc   2040
gcactgatct ctctccggtgc ggtgatcctg ctggagttca tcccggaaat cgccatcccg   2100
gtactgggca cctttgctct ggtttcttac attgcaaaca aggttctgac tgtacaaacc   2160
atcgacaacg cgctgagcaa acgtaacgaa aaatgggatg aagtttacaa atatatcgtg   2220
accaactggc tggctaaggt taatactcag atcgacctca tccgcaaaaa aatgaaagaa   2280
gcactggaaa accaggcgga agctaccaag gcaatcatta actaccagta caaccagtac   2340
accgaggaag aaaaaaacaa catcaacttc aacatcgacg atctgtcctc taaactgaac   2400
gaatccatca caaagctat gatcaacatc aacaagttcc tgaaccagtg ctctgtaagc   2460
tatctgatga actccatgat cccgtacggt gttaacgtc tggaggactt cgatgcgtct   2520
ctgaaagacg ccctgctgaa atacatttac gacaaccgtg gcactctgat cggtcaggtt   2580
gatcgtctga aggacaaagt gaacaatacc ttatcgaccg acatcccctt tcagctcagt   2640
aaatatgtcg ataaccaacg cctttgtcc acttgtggcg gtggcggtag catcgaaggt   2700
cgtcagcact ggtcctattg cctgcgcccct ggttgataa                         2739
```

<210> SEQ ID NO 4  
<211> LENGTH: 911  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 4

```
Met His His His His His His His His Gly Ser Ser Asn Asn
1               5                   10                  15

Asn Asn Asn Asn Asn Asn Asn Gly Ser Met Glu Phe Val Asn Lys
                20                  25                  30

Gln Phe Asn Tyr Lys Asp Pro Val Asn Gly Val Asp Ile Ala Tyr Ile
            35                  40                  45

Lys Ile Pro Asn Ala Gly Gln Met Gln Pro Val Lys Ala Phe Lys Ile
    50                  55                  60

His Asn Lys Ile Trp Val Ile Pro Glu Arg Asp Thr Phe Thr Asn Pro
65                  70                  75                  80

Glu Gly Asp Leu Asn Pro Pro Glu Ala Lys Gln Val Pro Val
                85                  90                  95

Ser Tyr Tyr Asp Ser Thr Tyr Leu Ser Thr Asp Asn Glu Lys Asp Asn
            100                 105                 110

Tyr Leu Lys Gly Val Thr Lys Leu Phe Glu Arg Ile Tyr Ser Thr Asp
        115                 120                 125

Leu Gly Arg Met Leu Leu Thr Ser Ile Val Arg Gly Ile Pro Phe Trp
130                 135                 140

Gly Gly Ser Thr Ile Asp Thr Glu Leu Lys Val Ile Asp Thr Asn Cys
145                 150                 155                 160

Ile Asn Val Ile Gln Pro Asp Gly Ser Tyr Arg Ser Glu Glu Leu Asn
                165                 170                 175

Leu Val Ile Ile Gly Pro Ser Ala Asp Ile Ile Gln Phe Glu Cys Lys
            180                 185                 190

Ser Phe Gly His Glu Val Leu Asn Leu Thr Arg Asn Gly Tyr Gly Ser
        195                 200                 205

Thr Gln Tyr Ile Arg Phe Ser Pro Asp Phe Thr Phe Gly Phe Glu Glu
    210                 215                 220

Ser Leu Glu Val Asp Thr Asn Pro Leu Leu Gly Ala Gly Lys Phe Ala
225                 230                 235                 240

Thr Asp Pro Ala Val Thr Leu Ala His Glu Leu Ile His Ala Gly His
                245                 250                 255

Arg Leu Tyr Gly Ile Ala Ile Asn Pro Asn Arg Val Phe Lys Val Asn
            260                 265                 270

Thr Asn Ala Tyr Tyr Glu Met Ser Gly Leu Glu Val Ser Phe Glu Glu
        275                 280                 285

Leu Arg Thr Phe Gly Gly His Asp Ala Lys Phe Ile Asp Ser Leu Gln
    290                 295                 300

Glu Asn Glu Phe Arg Leu Tyr Tyr Tyr Asn Lys Phe Lys Asp Ile Ala
305                 310                 315                 320

Ser Thr Leu Asn Lys Ala Lys Ser Ile Val Gly Thr Thr Ala Ser Leu
                325                 330                 335

Gln Tyr Met Lys Asn Val Phe Lys Glu Lys Tyr Leu Leu Ser Glu Asp
            340                 345                 350

Thr Ser Gly Lys Phe Ser Val Asp Lys Leu Lys Phe Asp Lys Leu Tyr
        355                 360                 365

Lys Met Leu Thr Glu Ile Tyr Thr Glu Asp Asn Phe Val Lys Phe Phe
    370                 375                 380

Lys Val Leu Asn Arg Lys Thr Tyr Leu Asn Phe Asp Lys Ala Val Phe
385                 390                 395                 400

Lys Ile Asn Ile Val Pro Lys Val Asn Tyr Thr Ile Tyr Asp Gly Phe
```

```
            405                 410                 415
Asn Leu Arg Asn Thr Asn Leu Ala Ala Asn Phe Asn Gly Gln Asn Thr
            420                 425                 430

Glu Ile Asn Asn Met Asn Phe Thr Lys Leu Lys Asn Phe Thr Gly Leu
            435                 440                 445

Phe Glu Phe Tyr Lys Leu Leu Cys Val Asp Gly Ile Ile Thr Ser Lys
450                 455                 460

Thr Lys Ser Leu Ile Glu Gly Arg Asn Lys Ala Leu Asn Asp Leu Cys
465                 470                 475                 480

Ile Lys Val Asn Asn Trp Asp Leu Phe Phe Ser Pro Ser Glu Asp Asn
                485                 490                 495

Phe Thr Asn Asp Leu Asn Lys Gly Glu Ile Thr Ser Asp Thr Asn
            500                 505                 510

Ile Glu Ala Ala Glu Asn Ile Ser Leu Asp Leu Ile Gln Gln Tyr
            515                 520                 525

Tyr Leu Thr Phe Asn Phe Asp Asn Glu Pro Glu Asn Ile Ser Ile Glu
530                 535                 540

Asn Leu Ser Ser Asp Ile Ile Gly Gln Leu Glu Leu Met Pro Asn Ile
545                 550                 555                 560

Glu Arg Phe Pro Asn Gly Lys Lys Tyr Glu Leu Asp Lys Tyr Thr Met
                565                 570                 575

Phe His Tyr Leu Arg Ala Gln Glu Phe Glu His Gly Lys Ser Arg Ile
            580                 585                 590

Ala Leu Thr Asn Ser Val Asn Glu Ala Leu Leu Asn Pro Ser Arg Val
            595                 600                 605

Tyr Thr Phe Phe Ser Ser Asp Tyr Val Lys Lys Val Asn Lys Ala Thr
            610                 615                 620

Glu Ala Ala Met Phe Leu Gly Trp Val Glu Gln Leu Val Tyr Asp Phe
625                 630                 635                 640

Thr Asp Glu Thr Ser Glu Val Ser Thr Thr Asp Lys Ile Ala Asp Ile
                645                 650                 655

Thr Ile Ile Ile Pro Tyr Ile Gly Pro Ala Leu Asn Ile Gly Asn Met
            660                 665                 670

Leu Tyr Lys Asp Asp Phe Val Gly Ala Leu Ile Phe Ser Gly Ala Val
            675                 680                 685

Ile Leu Leu Glu Phe Ile Pro Glu Ile Ala Ile Pro Val Leu Gly Thr
            690                 695                 700

Phe Ala Leu Val Ser Tyr Ile Ala Asn Lys Val Leu Thr Val Gln Thr
705                 710                 715                 720

Ile Asp Asn Ala Leu Ser Lys Arg Asn Glu Lys Trp Asp Glu Val Tyr
                725                 730                 735

Lys Tyr Ile Val Thr Asn Trp Leu Ala Lys Val Asn Thr Gln Ile Asp
            740                 745                 750

Leu Ile Arg Lys Lys Met Lys Glu Ala Leu Glu Asn Gln Ala Glu Ala
            755                 760                 765

Thr Lys Ala Ile Ile Asn Tyr Gln Tyr Asn Gln Tyr Thr Glu Glu Glu
            770                 775                 780

Lys Asn Asn Ile Asn Phe Asn Ile Asp Asp Leu Ser Ser Lys Leu Asn
785                 790                 795                 800

Glu Ser Ile Asn Lys Ala Met Ile Asn Ile Asn Lys Phe Leu Asn Gln
                805                 810                 815

Cys Ser Val Ser Tyr Leu Met Asn Ser Met Ile Pro Tyr Gly Val Lys
            820                 825                 830
```

```
Arg Leu Glu Asp Phe Asp Ala Ser Leu Lys Asp Ala Leu Leu Lys Tyr
            835                 840                 845

Ile Tyr Asp Asn Arg Gly Thr Leu Ile Gly Gln Val Asp Arg Leu Lys
        850                 855                 860

Asp Lys Val Asn Asn Thr Leu Ser Thr Asp Ile Pro Phe Gln Leu Ser
865                 870                 875                 880

Lys Tyr Val Asp Asn Gln Arg Leu Leu Ser Thr Cys Gly Gly Gly
                885                 890                 895

Ser Ile Glu Gly Arg Gln His Trp Ser Tyr Cys Leu Arg Pro Gly
        900                 905                 910

<210> SEQ ID NO 5
<211> LENGTH: 2772
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgcatcacc atcaccatca ccatcaccat catgggagct cgaacaataa caacaataac    60
aataacaata acgatccat gacgtggcca gttaaggatt tcaactactc agatcctgta   120
aatgacaacg atattctgta ccttcgcatt ccacaaaata aactgatcac cacaccagtc   180
aaagcattca tgattactca aacatttggg gtcattccag aacgcttttc tagtgacaca   240
aatccgagtt tatctaaacc tccgcgtccg acgtccaaat atcagagcta ttacgatccc   300
tcatatctca gtacggacga caaaaaagat actttcctta aggtatcat taaactgttt   360 aagcgtatta tgagcgcga tatcgggaaa aagttgatta attatcttgt tgtgggttcc   420
ccgttcatgg gcgatagctc tacccccgaa gacactttg attttacccg tcatacgaca   480
aacatcgcgg tagagaagtt tgagaacgga tcgtggaaag tcacaaacat cattacacct   540
agcgtcttaa tttttggtcc gctgccaaac atcttagatt atacagccag cctgactttg   600
caggggcaac agtcgaatcc gagtttcgaa ggttttggta ccctgagcat tctgaaagtt   660
gccccggaat tctgctcac ttttcagat gtcaccagca accagagctc agcagtatta   720
ggaaagtcaa ttttttgcat ggacccggtt attgcactga tgcacgaact gacgcactct   780
ctgcatcaac tgtatgggat caacatcccc agtgacaaac gtattcgtcc ccaggtgtct   840
gaaggatttt tctcacagga tgggccgaac gtccagttcg aagagttgta ctttcgga    900 ggcctggacg tagagatcat tccccagatt gagcgcagtc agctgcgtga aggcattg    960 ggccattata aggatattgc aaaacgcctg aataacatta caaaacgat ccatcttcg   1020 tggatctcga atattgataa atataagaaa atttttagcg agaaatataa ttttgataaa   1080
gataatacag gtaactttgt ggttaacatt gacaaattca actcccttta cagtgatttg   1140
acgaatgtaa tgagcgaagt tgtgtatagt tcccaataca acgttaagaa tcgtacccat   1200
tacttctctc gtcactacct gccggttttc gcgaacatcc ttgacgataa tatttacact   1260
attcgtgacg gctttaactt gaccaacaag ggcttcaata ttgaaaattc aggccagaac   1320
attgaacgca acccggcctt gcagaaactg tcgagtgaat ccgtggttga cctgtttacc   1380
aaagtctgcg tcgacggcat cattacctcc aaaactaaat ctctgataga aggtagaaac   1440
aaagcgctga acctgcagtg tattaaagtg aaaaacaatc ggctgcctta tgtagcagat   1500
aaagatagca ttagtcagga gattttcgaa aataaaatta tcactgacga aaccaatgtt   1560
```

-continued

```
cagaattatt cagataaatt ttcactggac gaaagcatct tagatggcca agttccgatt    1620
aacccggaaa ttgttgatcc gttactgccg aacgtgaata tggaaccgtt aaacctccct    1680
ggcgaagaga tcgtatttta tgatgacatt acgaaatatg tggactacct taattcttat    1740
tactatttgg aaagccagaa actgtccaat aacgtggaaa acattactct gaccacaagc    1800
gtggaagagg ctttaggcta ctcaaataag atttatacct tcctcccgtc gctggcggaa    1860
aaagtaaata aggtgtgca ggctggtctg ttcctcaact gggcgaatga agttgtcgaa     1920
gactttacca cgaatattat gaaaaaggat accctggata aaatctccga cgtctcggtt    1980
attatcccat atattggccc tgcgttaaat atcggtaata gtgcgctgcg ggggaatttt    2040
aaccaggcct ttgctaccgc gggcgtcgcg ttcctcctgg agggctttcc tgaatttact    2100
atcccggcgc tcggtgtttt tacatttttac tcttccatcc aggagcgtga gaaaattatc    2160
aaaaccatcg aaaactgcct ggagcagcgg gtgaaacgct ggaaagattc ttatcaatgg    2220
atggtgtcaa actggttatc tcgcatcacg acccaattca accatattaa ttaccagatg    2280
tatgatagtc tgtcgtacca agctgacgcc attaaagcca aaattgatct ggaatataaa    2340
aagtactctg gtagcgataa ggagaacatc aaaagccagg tggagaacct taagaatagt    2400
ctggatgtga aatctctga agctatgaat aacattaaca aattcattcg tgaatgttcg     2460
gtgacgtacc tgttcaagaa tatgctgcca aaagttattg atgaactgaa taaatttgat    2520
ctgcgtacca aaaccgaact tatcaacctc atcgactccc acaacattat ccttgtgggc    2580
gaagtggatc gtctgaaggc caaagtaaac gagagctttg aaaatacgat gccgtttaat    2640
attttttcat ataccaataa ctccttgctg aaagatatca tcaatgaata tttcaatcta    2700
gaatgtggcg gtggcggtag cgacgatgac gataaacagc actggtccta ttgcctgcgc    2760
cctggttgat aa                                                        2772
```

<210> SEQ ID NO 6
<211> LENGTH: 922
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 6

```
Met His His His His His His His His His Gly Ser Ser Asn Asn
1               5                   10                  15

Asn Asn Asn Asn Asn Asn Asn Asn Gly Ser Met Thr Trp Pro Val Lys
            20                  25                  30

Asp Phe Asn Tyr Ser Asp Pro Val Asn Asp Asn Asp Ile Leu Tyr Leu
        35                  40                  45

Arg Ile Pro Gln Asn Lys Leu Ile Thr Thr Pro Val Lys Ala Phe Met
    50                  55                  60

Ile Thr Gln Asn Ile Trp Val Ile Pro Glu Arg Phe Ser Ser Asp Thr
65                  70                  75                  80

Asn Pro Ser Leu Ser Lys Pro Arg Pro Thr Ser Lys Tyr Gln Ser
                85                  90                  95

Tyr Tyr Asp Pro Ser Tyr Leu Ser Thr Asp Glu Gln Lys Asp Thr Phe
            100                 105                 110

Leu Lys Gly Ile Ile Lys Leu Phe Lys Arg Ile Asn Glu Arg Asp Ile
        115                 120                 125

Gly Lys Lys Leu Ile Asn Tyr Leu Val Val Gly Ser Pro Phe Met Gly
    130                 135                 140
```

```
Asp Ser Ser Thr Pro Glu Asp Thr Phe Asp Phe Thr Arg His Thr Thr
145                 150                 155                 160

Asn Ile Ala Val Glu Lys Phe Glu Asn Gly Ser Trp Lys Val Thr Asn
                165                 170                 175

Ile Ile Thr Pro Ser Val Leu Ile Phe Gly Pro Leu Pro Asn Ile Leu
            180                 185                 190

Asp Tyr Thr Ala Ser Leu Thr Leu Gln Gly Gln Gln Ser Asn Pro Ser
        195                 200                 205

Phe Glu Gly Phe Gly Thr Leu Ser Ile Leu Lys Val Ala Pro Glu Phe
    210                 215                 220

Leu Leu Thr Phe Ser Asp Val Thr Ser Asn Gln Ser Ser Ala Val Leu
225                 230                 235                 240

Gly Lys Ser Ile Phe Cys Met Asp Pro Val Ile Ala Leu Met His Glu
                245                 250                 255

Leu Thr His Ser Leu His Gln Leu Tyr Gly Ile Asn Ile Pro Ser Asp
            260                 265                 270

Lys Arg Ile Arg Pro Gln Val Ser Glu Gly Phe Phe Ser Gln Asp Gly
        275                 280                 285

Pro Asn Val Gln Phe Glu Glu Leu Tyr Thr Phe Gly Gly Leu Asp Val
    290                 295                 300

Glu Ile Ile Pro Gln Ile Glu Arg Ser Gln Leu Arg Glu Lys Ala Leu
305                 310                 315                 320

Gly His Tyr Lys Asp Ile Ala Lys Arg Leu Asn Asn Ile Asn Lys Thr
                325                 330                 335

Ile Pro Ser Ser Trp Ile Ser Asn Ile Asp Lys Tyr Lys Lys Ile Phe
            340                 345                 350

Ser Glu Lys Tyr Asn Phe Asp Lys Asp Asn Thr Gly Asn Phe Val Val
        355                 360                 365

Asn Ile Asp Lys Phe Asn Ser Leu Tyr Ser Asp Leu Thr Asn Val Met
    370                 375                 380

Ser Glu Val Val Tyr Ser Ser Gln Tyr Asn Val Lys Asn Arg Thr His
385                 390                 395                 400

Tyr Phe Ser Arg His Tyr Leu Pro Val Phe Ala Asn Ile Leu Asp Asp
                405                 410                 415

Asn Ile Tyr Thr Ile Arg Asp Gly Phe Asn Leu Thr Asn Lys Gly Phe
            420                 425                 430

Asn Ile Glu Asn Ser Gly Gln Asn Ile Glu Arg Asn Pro Ala Leu Gln
        435                 440                 445

Lys Leu Ser Ser Glu Ser Val Val Asp Leu Phe Thr Lys Val Cys Val
    450                 455                 460

Asp Gly Ile Ile Thr Ser Lys Thr Lys Ser Leu Ile Glu Gly Arg Asn
465                 470                 475                 480

Lys Ala Leu Asn Leu Gln Cys Ile Lys Val Lys Asn Asn Arg Leu Pro
                485                 490                 495

Tyr Val Ala Asp Lys Asp Ser Ile Ser Gln Glu Ile Phe Glu Asn Lys
            500                 505                 510

Ile Ile Thr Asp Glu Thr Asn Val Gln Asn Tyr Ser Asp Lys Phe Ser
        515                 520                 525

Leu Asp Glu Ser Ile Leu Asp Gly Gln Val Pro Ile Asn Pro Glu Ile
    530                 535                 540

Val Asp Pro Leu Leu Pro Asn Val Asn Met Glu Pro Leu Asn Leu Pro
545                 550                 555                 560
```

Gly Glu Glu Ile Val Phe Tyr Asp Asp Ile Thr Lys Tyr Val Asp Tyr
                565                 570                 575

Leu Asn Ser Tyr Tyr Leu Glu Ser Gln Lys Leu Ser Asn Asn Val
    580                 585                 590

Glu Asn Ile Thr Leu Thr Thr Ser Val Glu Glu Ala Leu Gly Tyr Ser
            595                 600                 605

Asn Lys Ile Tyr Thr Phe Leu Pro Ser Leu Ala Glu Lys Val Asn Lys
        610                 615                 620

Gly Val Gln Ala Gly Leu Phe Leu Asn Trp Ala Asn Glu Val Val Glu
625                 630                 635                 640

Asp Phe Thr Thr Asn Ile Met Lys Lys Asp Thr Leu Asp Lys Ile Ser
                645                 650                 655

Asp Val Ser Val Ile Ile Pro Tyr Ile Gly Pro Ala Leu Asn Ile Gly
            660                 665                 670

Asn Ser Ala Leu Arg Gly Asn Phe Asn Gln Ala Phe Ala Thr Ala Gly
        675                 680                 685

Val Ala Phe Leu Leu Glu Gly Phe Pro Glu Phe Thr Ile Pro Ala Leu
    690                 695                 700

Gly Val Phe Thr Phe Tyr Ser Ser Ile Gln Glu Arg Glu Lys Ile Ile
705                 710                 715                 720

Lys Thr Ile Glu Asn Cys Leu Glu Gln Arg Val Lys Arg Trp Lys Asp
                725                 730                 735

Ser Tyr Gln Trp Met Val Ser Asn Trp Leu Ser Arg Ile Thr Thr Gln
            740                 745                 750

Phe Asn His Ile Asn Tyr Gln Met Tyr Asp Ser Leu Ser Tyr Gln Ala
        755                 760                 765

Asp Ala Ile Lys Ala Lys Ile Asp Leu Glu Tyr Lys Lys Tyr Ser Gly
    770                 775                 780

Ser Asp Lys Glu Asn Ile Lys Ser Gln Val Glu Asn Leu Lys Asn Ser
785                 790                 795                 800

Leu Asp Val Lys Ile Ser Glu Ala Met Asn Asn Ile Asn Lys Phe Ile
                805                 810                 815

Arg Glu Cys Ser Val Thr Tyr Leu Phe Lys Asn Met Leu Pro Lys Val
            820                 825                 830

Ile Asp Glu Leu Asn Lys Phe Asp Leu Arg Thr Lys Thr Glu Leu Ile
        835                 840                 845

Asn Leu Ile Asp Ser His Asn Ile Ile Leu Val Gly Glu Val Asp Arg
    850                 855                 860

Leu Lys Ala Lys Val Asn Glu Ser Phe Glu Asn Thr Met Pro Phe Asn
865                 870                 875                 880

Ile Phe Ser Tyr Thr Asn Asn Ser Leu Leu Lys Asp Ile Ile Asn Glu
                885                 890                 895

Tyr Phe Asn Leu Glu Cys Gly Gly Gly Ser Asp Asp Asp Asp Lys
            900                 905                 910

Gln His Trp Ser Tyr Cys Leu Arg Pro Gly
        915                 920

<210> SEQ ID NO 7
<211> LENGTH: 2850
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

-continued

```
atgcatcacc atcaccatca ccatcaccat catgggagct cgaacaataa caacaataac    60
aataacaata acggatccat gacgtggcca gttaaggatt tcaactactc agatcctgta   120
aatgacaacg atattctgta ccttcgcatt ccacaaaata aactgatcac cacaccagtc   180
aaagcattca tgattactca aaacatttgg gtcattccag aacgcttttc tagtgacaca   240
aatccgagtt tatctaaacc tccgcgtccg acgtccaaat atcagagcta ttacgatccc   300
tcatatctca gtacggacga acaaaaagat actttcctta aggtatcat  taaactgttt   360
aagcgtatta atgagcgcga tatcgggaaa aagttgatta attatcttgt tgtgggttcc   420
ccgttcatgg gcgatagctc tacccccgaa gacactttg  attttacccg tcatacgaca   480
aacatcgcgg tagagaagtt tgagaacgga tcgtggaaag tcacaaacat cattacacct   540
agcgtcttaa tttttggtcc gctgccaaac atcttagatt atacagccag cctgactttg   600
caggggcaac agtcgaatcc gagtttcgaa ggttttggta ccctgagcat tctgaaagtt   660
gccccggaat ttctgctcac ttttcagat  gtcaccagca accagagctc agcagtatta   720
ggaaagtcaa tttttgcat  ggacccggtt attgcactga tgcacgaact gacgcactct   780
ctgcatcaac tgtatgggat caacatcccc agtgacaaac gtattcgtcc ccaggtgtct   840
gaaggatttt tctcacagga tgggccgaac gtccagttcg aagagttgta tactttcgga   900
ggcctggacg tagagatcat tccccagatt gagcgcagtc agctgcgtga aaggcattg    960
ggccattata aggatattgc aaaacgcctg aataacatta acaaaacgat tccatcttcg  1020
tggatctcga atattgataa atataagaaa atttttagcg agaaatataa ttttgataaa  1080
gataatacag gtaactttgt ggttaacatt gacaaattca actcccttta cagtgatttg  1140
acgaatgtaa tgagcgaagt tgtgtatagt tcccaataca acgttaagaa tcgtacccat  1200
tacttctctc gtcactacct gccggttttc gcgaacatcc ttgacgataa tatttacact  1260
attcgtgacg gctttaactt gaccaacaag ggcttcaata ttgaaaattc aggccagaac  1320
attgaacgca acccggcctt gcagaaactg tcgagtgaat ccgtggttga cctgtttacc  1380
aaagtctgcg tcgacggcat cattacctcc aaaactaaat ctctgataga aggtagaaac  1440
aaagcgctga acctgcagtg tattaaagtg aaaaacaatc ggctgcctta tgtagcagat  1500
aaagatagca ttagtcagga gattttcgaa aataaaatta tcactgacga accaatgtt   1560
cagaattatt cagataaatt ttcactggac gaaagcatct tagatggcca agttccgatt  1620
aacccggaaa ttgttgatcc gttactgccg aacgtgaata tggaaccgtt aaacctccct  1680
ggcgaagaga tcgtatttta tgatgacatt acgaaatatg tggactacct taattcttat  1740
tactatttgg aaagccagaa actgtccaat aacgtggaaa acattactct gaccacaagc  1800
gtggaagagg ctttaggcta ctcaaataag atttatacct tcctcccgtc gctggcggaa  1860
aaagtaaata aggtgtgcat ggctggtctg ttcctcaact gggcgaatga agttgtcgaa  1920
gactttacca cgaatattat gaaaaaggat accctgata  aaatctccga cgtctcggtt  1980
attatcccat atattggccc tgcgttaaat atcggtaata gtgcgctgcg ggggaatttt  2040
aaccaggcct tgctaccgc  gggcgtcgcg ttcctcctgg agggctttcc tgaatttact  2100
atcccggcgc tcggtgtttt tacatttac  tcttccatcc aggagcgtga gaaaattatc  2160
aaaaccatcg aaaactgcct ggagcagcgg gtgaaacgct ggaaagattc ttatcaatgg  2220
atggtgtcaa actggttatc tcgcatcacg acccaattca accatattaa ttaccagatg  2280
tatgatagtc tgtcgtacca agctgacgcc attaaagcca aaattgatct ggaatataaa  2340
```

```
aagtactctg gtagcgataa ggagaacatc aaaagccagg tggagaacct taagaatagt    2400
ctggatgtga aaatctctga agctatgaat aacattaaca aattcattcg tgaatgttcg    2460
gtgacgtacc tgttcaagaa tatgctgcca aaagttattg atgaactgaa taaatttgat    2520
ctgcgtacca aaaccgaact tatcaacctc atcgactccc acaacattat ccttgtgggc    2580
gaagtggatc gtctgaaggc caaagtaaac gagagctttg aaaatacgat gccgtttaat    2640
attttttcat ataccaataa ctccttgctg aaagatatca tcaatgaata tttcaatcta    2700
gaatgtggcg gtggcggtag catcgaaggt cgttatggag gttttttgag aaggatacga    2760
ccaaaattaa agtgggataa tcaaggcggt gggggtagtt gcggcggtgg cggttcgcgt    2820
ccgccgggtt tctctccgtt ccgttgataa                                     2850
```

<210> SEQ ID NO 8
<211> LENGTH: 948
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met His His His His His His His His Gly Ser Ser Asn Asn
1               5                   10                  15

Asn Asn Asn Asn Asn Asn Asn Asn Gly Ser Met Thr Trp Pro Val Lys
            20                  25                  30

Asp Phe Asn Tyr Ser Asp Pro Val Asn Asp Asn Asp Ile Leu Tyr Leu
        35                  40                  45

Arg Ile Pro Gln Asn Lys Leu Ile Thr Thr Pro Val Lys Ala Phe Met
    50                  55                  60

Ile Thr Gln Asn Ile Trp Val Ile Pro Glu Arg Phe Ser Ser Asp Thr
65                  70                  75                  80

Asn Pro Ser Leu Ser Lys Pro Pro Arg Pro Thr Ser Lys Tyr Gln Ser
                85                  90                  95

Tyr Tyr Asp Pro Ser Tyr Leu Ser Thr Asp Glu Gln Lys Asp Thr Phe
            100                 105                 110

Leu Lys Gly Ile Ile Lys Leu Phe Lys Arg Ile Asn Glu Arg Asp Ile
        115                 120                 125

Gly Lys Lys Leu Ile Asn Tyr Leu Val Val Gly Ser Pro Phe Met Gly
    130                 135                 140

Asp Ser Ser Thr Pro Glu Asp Thr Phe Asp Phe Thr Arg His Thr Thr
145                 150                 155                 160

Asn Ile Ala Val Glu Lys Phe Glu Asn Gly Ser Trp Lys Val Thr Asn
                165                 170                 175

Ile Ile Thr Pro Ser Val Leu Ile Phe Gly Pro Leu Pro Asn Ile Leu
            180                 185                 190

Asp Tyr Thr Ala Ser Leu Thr Leu Gln Gly Gln Gln Ser Asn Pro Ser
        195                 200                 205

Phe Glu Gly Phe Gly Thr Leu Ser Ile Leu Lys Val Ala Pro Glu Phe
    210                 215                 220

Leu Leu Thr Phe Ser Asp Val Thr Ser Asn Gln Ser Ser Ala Val Leu
225                 230                 235                 240

Gly Lys Ser Ile Phe Cys Met Asp Pro Val Ile Ala Leu Met His Glu
                245                 250                 255

Leu Thr His Ser Leu His Gln Leu Tyr Gly Ile Asn Ile Pro Ser Asp
            260                 265                 270
```

-continued

```
Lys Arg Ile Arg Pro Gln Val Ser Glu Gly Phe Phe Ser Gln Asp Gly
            275                 280                 285

Pro Asn Val Gln Phe Glu Glu Leu Tyr Thr Phe Gly Gly Leu Asp Val
        290                 295                 300

Glu Ile Ile Pro Gln Ile Glu Arg Ser Gln Leu Arg Glu Lys Ala Leu
305                 310                 315                 320

Gly His Tyr Lys Asp Ile Ala Lys Arg Leu Asn Asn Ile Asn Lys Thr
                325                 330                 335

Ile Pro Ser Ser Trp Ile Ser Asn Ile Asp Lys Tyr Lys Lys Ile Phe
                340                 345                 350

Ser Glu Lys Tyr Asn Phe Asp Lys Asp Asn Thr Gly Asn Phe Val Val
            355                 360                 365

Asn Ile Asp Lys Phe Asn Ser Leu Tyr Ser Asp Leu Thr Asn Val Met
        370                 375                 380

Ser Glu Val Val Tyr Ser Ser Gln Tyr Asn Val Lys Asn Arg Thr His
385                 390                 395                 400

Tyr Phe Ser Arg His Tyr Leu Pro Val Phe Ala Asn Ile Leu Asp Asp
                405                 410                 415

Asn Ile Tyr Thr Ile Arg Asp Gly Phe Asn Leu Thr Asn Lys Gly Phe
                420                 425                 430

Asn Ile Glu Asn Ser Gly Gln Asn Ile Glu Arg Asn Pro Ala Leu Gln
            435                 440                 445

Lys Leu Ser Ser Glu Ser Val Val Asp Leu Phe Thr Lys Val Cys Val
        450                 455                 460

Asp Gly Ile Ile Thr Ser Lys Thr Lys Ser Leu Ile Glu Gly Arg Asn
465                 470                 475                 480

Lys Ala Leu Asn Leu Gln Cys Ile Lys Val Lys Asn Asn Arg Leu Pro
                485                 490                 495

Tyr Val Ala Asp Lys Asp Ser Ile Ser Gln Glu Ile Phe Glu Asn Lys
                500                 505                 510

Ile Ile Thr Asp Glu Thr Asn Val Gln Asn Tyr Ser Asp Lys Phe Ser
            515                 520                 525

Leu Asp Glu Ser Ile Leu Asp Gly Gln Val Pro Ile Asn Pro Glu Ile
        530                 535                 540

Val Asp Pro Leu Leu Pro Asn Val Asn Met Glu Pro Leu Asn Leu Pro
545                 550                 555                 560

Gly Glu Glu Ile Val Phe Tyr Asp Asp Ile Thr Lys Tyr Val Asp Tyr
                565                 570                 575

Leu Asn Ser Tyr Tyr Tyr Leu Glu Ser Gln Lys Leu Ser Asn Asn Val
                580                 585                 590

Glu Asn Ile Thr Leu Thr Thr Ser Val Glu Glu Ala Leu Gly Tyr Ser
            595                 600                 605

Asn Lys Ile Tyr Thr Phe Leu Pro Ser Leu Ala Glu Lys Val Asn Lys
        610                 615                 620

Gly Val Gln Ala Gly Leu Phe Leu Asn Trp Ala Asn Glu Val Val Glu
625                 630                 635                 640

Asp Phe Thr Thr Asn Ile Met Lys Lys Asp Thr Leu Asp Lys Ile Ser
                645                 650                 655

Asp Val Ser Val Ile Ile Pro Tyr Ile Gly Pro Ala Leu Asn Ile Gly
                660                 665                 670

Asn Ser Ala Leu Arg Gly Asn Phe Asn Gln Ala Phe Ala Thr Ala Gly
            675                 680                 685
```

```
Val Ala Phe Leu Leu Glu Gly Phe Pro Glu Phe Thr Ile Pro Ala Leu
    690                 695                 700

Gly Val Phe Thr Phe Tyr Ser Ser Ile Gln Glu Arg Glu Lys Ile Ile
705                 710                 715                 720

Lys Thr Ile Glu Asn Cys Leu Glu Gln Arg Val Lys Arg Trp Lys Asp
                725                 730                 735

Ser Tyr Gln Trp Met Val Ser Asn Trp Leu Ser Arg Ile Thr Thr Gln
            740                 745                 750

Phe Asn His Ile Asn Tyr Gln Met Tyr Asp Ser Leu Ser Tyr Gln Ala
        755                 760                 765

Asp Ala Ile Lys Ala Lys Ile Asp Leu Glu Tyr Lys Lys Tyr Ser Gly
    770                 775                 780

Ser Asp Lys Glu Asn Ile Lys Ser Gln Val Glu Asn Leu Lys Asn Ser
785                 790                 795                 800

Leu Asp Val Lys Ile Ser Glu Ala Met Asn Asn Ile Asn Lys Phe Ile
                805                 810                 815

Arg Glu Cys Ser Val Thr Tyr Leu Phe Lys Asn Met Leu Pro Lys Val
            820                 825                 830

Ile Asp Glu Leu Asn Lys Phe Asp Leu Arg Thr Lys Thr Glu Leu Ile
        835                 840                 845

Asn Leu Ile Asp Ser His Asn Ile Ile Leu Val Gly Glu Val Asp Arg
    850                 855                 860

Leu Lys Ala Lys Val Asn Glu Ser Phe Glu Asn Thr Met Pro Phe Asn
865                 870                 875                 880

Ile Phe Ser Tyr Thr Asn Asn Ser Leu Leu Lys Asp Ile Ile Asn Glu
                885                 890                 895

Tyr Phe Asn Leu Glu Cys Gly Gly Gly Ser Ile Glu Gly Arg Tyr
            900                 905                 910

Gly Gly Phe Leu Arg Arg Ile Arg Pro Lys Leu Lys Trp Asp Asn Gln
        915                 920                 925

Gly Gly Gly Gly Ser Cys Gly Gly Gly Ser Arg Pro Pro Gly Phe
    930                 935                 940

Ser Pro Phe Arg
945
```

<210> SEQ ID NO 9
<211> LENGTH: 2862
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgcatcacc atcaccatca ccatcaccat catgggagct cgaacaataa caacaataac     60
aataacaata acggatccat ggagttcgtt aacaaacagt tcaactataa agacccagtt    120
aacggtgttg acattgctta catcaaaatc ccgaacgctg ccagatgca gccggtaaag    180 gcattcaaaa tccacaacaa atctggggtt atcccggaac gtgataccttt actaacccg    240 gaagaaggtg acctgaaccc gccaccggaa gcgaaacagg tgccggtatc ttactatgac    300
tccacctacc tgtctaccga taacgaaaag gacaactacc tgaaaggtgt tactaaactg    360
ttcgagcgta tttactccac cgacctgggc cgtatgctgc tgactagcat cgttcgcggt    420
atcccgttct ggggcggttc taccatcgat accgaactga agtaatcga cactaactgc    480 atcaacgtta ttcagccgga cggttcctat cgttccgaag aactgaacct ggtgatcatc    540
```

```
ggcccgtctg ctgatatcat ccagttcgag tgtaagagct ttggtcacga agttctgaac    600
ctcacccgta acggctacgg ttccactcag tacatccgtt tctctccgga cttcaccttc    660
ggttttgaag aatccctgga agtagacacg aacccactgc tgggcgctgg taaattcgca    720
actgatcctg cggttaccct ggctcacgaa ctgattcatg caggccaccg cctgtacggt    780
atcgccatca atccgaaccg tgtcttcaaa gttaacacca acgcgtatta cgagatgtcc    840
ggtctggaag ttagcttcga agaactgcgt acttttggcg gtcacgacgc taaattcatc    900
gactctctgc aagaaaacga gttccgtctg tactactata acaagttcaa agatatcgca    960
tccaccctga caaagcgaaa tccatcgtg ggtaccactg cttctctcca gtacatgaag   1020
aacgttttta agaaaaata cctgctcagc gaagacacct ccggcaaatt ctctgtagac   1080
aagttgaaat tcgataaact ttacaaaatg ctgactgaaa tttacaccga agacaacttc   1140
gttaagttct ttaaagttct gaaccgcaaa acctatctga acttcgacaa ggcagtattc   1200
aaaatcaaca tcgtgccgaa agttaactac actatctacg atggtttcaa cctgcgtaac   1260
accaacctgg ctgctaattt taacggccag aacacggaaa tcaacaacat gaacttcaca   1320
aaactgaaaa acttcactgg tctgttcgag ttttacaagc tgctgtgcgt cgacggcatc   1380
attacctcca aaactaaatc tctgatagaa ggtagaaaca aagcgctgaa cgacctctgt   1440
atcaaggtta caactgggga tttattcttc agcccgagtg aagacaactt caccaacgac   1500
ctgaacaaag gtgaagaaat cacctcagat actaacatcg aagcagccga agaaaacatc   1560
tcgctggacc tgatccagca gtactacctg acctttaatt tcgacaacga gccgaaaaac   1620
atttctatcg aaacctgag ctctgatatc atcggccagc tggaactgat gccgaacatc   1680
gaacgtttcc caaacggtaa aaagtacgag ctggacaaat ataccatgtt ccactacctg   1740
cgcgcgcagg aatttgaaca cggcaaatcc cgtatcgcac tgactaactc cgttaacgaa   1800
gctctgctca acccgtcccg tgtatacacc ttcttctcta gcgactacgt gaaaaaggtc   1860
aacaaagcga ctgaagctgc aatgttcttg ggttgggttg aacagcttgt ttatgatttt   1920
accgacgaga cgtccgaagt atctactacc gacaaaattg cggatatcac tatcatcatc   1980
ccgtacatcg gtccggctct gaacattggc aacatgctgt acaaagacga cttcgttggc   2040
gcactgatct tctccggtgc ggtgatcctg ctggagttca tcccggaaat cgccatcccg   2100
gtactgggca ccttttgctct ggttcttac attgcaaaca aggttctgac tgtacaaacc   2160
atcgacaacg cgctgagcaa acgtaacgaa aaatgggatg aagtttacaa atatatcgtg   2220
accaactggc tggctaaggt taatactcag atcgacctca tccgcaaaaa aatgaaagaa   2280
gcactggaaa accaggcgga agctaccaag gcaatcatta actaccagta caaccagtac   2340
accgaggaag aaaaaaacaa catcaacttc aacatcgacg atctgtcctc taaactgaac   2400
gaatccatca caaagctat gatcaacatc aacaagttcc tgaaccagtg ctctgtaagc   2460
tatctgatga actccatgat cccgtacggt gttaacgtc tggaggactt cgatgcgtct   2520
ctgaaagacg ccctgctgaa atacatttac gacaaccgtg gcactctgat cggtcaggtt   2580
gatcgtctga aggacaaagt gaacaatacc ttatcgaccg acatcccttt tcagctcagt   2640
aaatatgtcg ataaccaacg cctttttgtcc acttgtggcg gtggcggtag catcgaaggt   2700
cgttacggtg gtttcatgac ctctgaaaaa tctcagaccc cgctggttac cctgttcaaa   2760
aacgctatca tcaaaaacgc ttacaaaaaa ggtgaaggcg gtggggtag ttgcggcggt   2820 ggcggttcgc gtccgccggg tttctctccg ttccgttgat aa                     2862
```

<210> SEQ ID NO 10
<211> LENGTH: 952
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met His His His His His His His His His Gly Ser Ser Asn Asn
1               5                   10                  15

Asn Asn Asn Asn Asn Asn Asn Asn Gly Ser Met Glu Phe Val Asn Lys
                20                  25                  30

Gln Phe Asn Tyr Lys Asp Pro Val Asn Gly Val Asp Ile Ala Tyr Ile
            35                  40                  45

Lys Ile Pro Asn Ala Gly Gln Met Gln Pro Val Lys Ala Phe Lys Ile
    50                  55                  60

His Asn Lys Ile Trp Val Ile Pro Glu Arg Asp Thr Phe Thr Asn Pro
65                  70                  75                  80

Glu Glu Gly Asp Leu Asn Pro Pro Glu Ala Lys Gln Val Pro Val
                85                  90                  95

Ser Tyr Tyr Asp Ser Thr Tyr Leu Ser Thr Asp Asn Glu Lys Asp Asn
            100                 105                 110

Tyr Leu Lys Gly Val Thr Lys Leu Phe Glu Arg Ile Tyr Ser Thr Asp
        115                 120                 125

Leu Gly Arg Met Leu Leu Thr Ser Ile Val Arg Gly Ile Pro Phe Trp
    130                 135                 140

Gly Gly Ser Thr Ile Asp Thr Glu Leu Lys Val Ile Asp Thr Asn Cys
145                 150                 155                 160

Ile Asn Val Ile Gln Pro Asp Gly Ser Tyr Arg Ser Glu Glu Leu Asn
                165                 170                 175

Leu Val Ile Ile Gly Pro Ser Ala Asp Ile Ile Gln Phe Glu Cys Lys
            180                 185                 190

Ser Phe Gly His Glu Val Leu Asn Leu Thr Arg Asn Gly Tyr Gly Ser
        195                 200                 205

Thr Gln Tyr Ile Arg Phe Ser Pro Asp Phe Thr Phe Gly Phe Glu Glu
    210                 215                 220

Ser Leu Glu Val Asp Thr Asn Pro Leu Leu Gly Ala Gly Lys Phe Ala
225                 230                 235                 240

Thr Asp Pro Ala Val Thr Leu Ala His Glu Leu Ile His Ala Gly His
                245                 250                 255

Arg Leu Tyr Gly Ile Ala Ile Asn Pro Asn Arg Val Phe Lys Val Asn
            260                 265                 270

Thr Asn Ala Tyr Tyr Glu Met Ser Gly Leu Glu Val Ser Phe Glu Glu
        275                 280                 285

Leu Arg Thr Phe Gly Gly His Asp Ala Lys Phe Ile Asp Ser Leu Gln
    290                 295                 300

Glu Asn Glu Phe Arg Leu Tyr Tyr Asn Lys Phe Lys Asp Ile Ala
305                 310                 315                 320

Ser Thr Leu Asn Lys Ala Lys Ser Ile Val Gly Thr Thr Ala Ser Leu
                325                 330                 335

Gln Tyr Met Lys Asn Val Phe Lys Glu Lys Tyr Leu Leu Ser Glu Asp
            340                 345                 350

Thr Ser Gly Lys Phe Ser Val Asp Lys Leu Lys Phe Asp Lys Leu Tyr
        355                 360                 365
```

```
Lys Met Leu Thr Glu Ile Tyr Thr Glu Asp Asn Phe Val Lys Phe Phe
    370                 375                 380

Lys Val Leu Asn Arg Lys Thr Tyr Leu Asn Phe Asp Lys Ala Val Phe
385                 390                 395                 400

Lys Ile Asn Ile Val Pro Lys Val Asn Tyr Thr Ile Tyr Asp Gly Phe
                405                 410                 415

Asn Leu Arg Asn Thr Asn Leu Ala Ala Asn Phe Asn Gly Gln Asn Thr
            420                 425                 430

Glu Ile Asn Asn Met Asn Phe Thr Lys Leu Lys Asn Phe Thr Gly Leu
        435                 440                 445

Phe Glu Phe Tyr Lys Leu Leu Cys Val Asp Gly Ile Ile Thr Ser Lys
    450                 455                 460

Thr Lys Ser Leu Ile Glu Gly Arg Asn Lys Ala Leu Asn Asp Leu Cys
465                 470                 475                 480

Ile Lys Val Asn Asn Trp Asp Leu Phe Phe Ser Pro Ser Glu Asp Asn
                485                 490                 495

Phe Thr Asn Asp Leu Asn Lys Gly Glu Ile Thr Ser Asp Thr Asn
            500                 505                 510

Ile Glu Ala Ala Glu Glu Asn Ile Ser Leu Asp Leu Ile Gln Gln Tyr
        515                 520                 525

Tyr Leu Thr Phe Asn Phe Asp Asn Glu Pro Glu Asn Ile Ser Ile Glu
    530                 535                 540

Asn Leu Ser Ser Asp Ile Ile Gly Gln Leu Glu Leu Met Pro Asn Ile
545                 550                 555                 560

Glu Arg Phe Pro Asn Gly Lys Lys Tyr Glu Leu Asp Lys Tyr Thr Met
                565                 570                 575

Phe His Tyr Leu Arg Ala Gln Glu Phe Glu His Gly Lys Ser Arg Ile
            580                 585                 590

Ala Leu Thr Asn Ser Val Asn Glu Ala Leu Leu Asn Pro Ser Arg Val
        595                 600                 605

Tyr Thr Phe Phe Ser Ser Asp Tyr Val Lys Lys Val Asn Lys Ala Thr
    610                 615                 620

Glu Ala Ala Met Phe Leu Gly Trp Val Glu Gln Leu Val Tyr Asp Phe
625                 630                 635                 640

Thr Asp Glu Thr Ser Glu Val Ser Thr Thr Asp Lys Ile Ala Asp Ile
                645                 650                 655

Thr Ile Ile Ile Pro Tyr Ile Gly Pro Ala Leu Asn Ile Gly Asn Met
            660                 665                 670

Leu Tyr Lys Asp Asp Phe Val Gly Ala Leu Ile Phe Ser Gly Ala Val
        675                 680                 685

Ile Leu Leu Glu Phe Ile Pro Glu Ile Ala Ile Pro Val Leu Gly Thr
    690                 695                 700

Phe Ala Leu Val Ser Tyr Ile Ala Asn Lys Val Leu Thr Val Gln Thr
705                 710                 715                 720

Ile Asp Asn Ala Leu Ser Lys Arg Asn Glu Lys Trp Asp Glu Val Tyr
                725                 730                 735

Lys Tyr Ile Val Thr Asn Trp Leu Ala Lys Val Asn Thr Gln Ile Asp
            740                 745                 750

Leu Ile Arg Lys Lys Met Lys Glu Ala Leu Glu Asn Gln Ala Glu Ala
        755                 760                 765

Thr Lys Ala Ile Ile Asn Tyr Gln Tyr Asn Gln Tyr Thr Glu Glu Glu
    770                 775                 780
```

```
Lys Asn Asn Ile Asn Phe Asn Ile Asp Asp Leu Ser Ser Lys Leu Asn
785                 790                 795                 800

Glu Ser Ile Asn Lys Ala Met Ile Asn Ile Asn Lys Phe Leu Asn Gln
            805                 810                 815

Cys Ser Val Ser Tyr Leu Met Asn Ser Met Ile Pro Tyr Gly Val Lys
            820                 825                 830

Arg Leu Glu Asp Phe Asp Ala Ser Leu Lys Asp Ala Leu Leu Lys Tyr
            835                 840                 845

Ile Tyr Asp Asn Arg Gly Thr Leu Ile Gly Gln Val Asp Arg Leu Lys
    850                 855                 860

Asp Lys Val Asn Asn Thr Leu Ser Thr Asp Ile Pro Phe Gln Leu Ser
865                 870                 875                 880

Lys Tyr Val Asp Asn Gln Arg Leu Leu Ser Thr Cys Gly Gly Gly Gly
            885                 890                 895

Ser Ile Glu Gly Arg Tyr Gly Gly Phe Met Thr Ser Glu Lys Ser Gln
            900                 905                 910

Thr Pro Leu Val Thr Leu Phe Lys Asn Ala Ile Ile Lys Asn Ala Tyr
            915                 920                 925

Lys Lys Gly Glu Gly Gly Gly Ser Cys Gly Gly Gly Ser Arg
            930                 935                 940

Pro Pro Gly Phe Ser Pro Phe Arg
945                 950

<210> SEQ ID NO 11
<211> LENGTH: 3012
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgcatcacc atcaccatca ccatcaccat catgggagct cgaacaataa caacaataac        60
aataacaata acgatccat gacgtggcca gttaaggatt tcaactactc agatcctgta       120
aatgacaacg atattctgta ccttcgcatt ccacaaaata aactgatcac cacaccagtc       180
aaagcattca tgattactca aaacatttgg gtcattccag aacgcttttc tagtgacaca       240
aatccgagtt atctaaaacc tccgcgtccg acgtccaaat atcagagcta ttacgatccc       300
tcatatctca gtacggacga acaaaaagat actttcctta aaggtatcat taaactgttt       360
aagcgtatta tgagcgcga tatcgggaaa aagttgatta ttatcttgt tgtgggttcc        420 ccgttcatgg gcgatagctc tacccccgaa gacactttg attttacccg tcatacgaca       480
aacatcgcgg tagagaagtt tgagaacgga tcgtggaaag tcacaaacat cattacacct       540
agcgtcttaa ttttttggtcc gctgccaaac atcttagatt atacagccag cctgactttg       600
caggggcaac agtcgaatcc gagtttcgaa ggttttggta ccctgagcat tctgaaagtt       660
gccccggaat ttctgctcac ttttcagat gtcaccagca accagagctc agcagtatta       720
ggaaagtcaa tttttgcat ggacccggt tattgcactga tgcacgaact gacgcactct        780
ctgcatcaac tgtatgggat caacatcccc agtgacaaac gtattcgtcc ccaggtgtct       840
gaaggatttt tctcacagga tgggccgaac gtccagttcg aagagttgta tctttcgga        900 ggcctggacg tagagatcat tccccagatt gagcgcagtc agctgcgtga aaggcattg       960 ggccattata aggatattgc aaaacgccct aataacatta caaaacgat tccatcttcg       1020 tggatctcga atattgataa atataagaaa attttttagcg agaaatataa ttttgataaa       1080
```

```
gataatacag gtaactttgt ggttaacatt gacaaattca actcccttta cagtgatttg    1140
acgaatgtaa tgagcgaagt tgtgtatagt tcccaataca acgttaagaa tcgtacccat    1200
tacttctctc gtcactacct gccggttttc gcgaacatcc ttgacgataa tatttacact    1260
attcgtgacg gctttaactt gaccaacaag ggcttcaata ttgaaaattc aggccagaac    1320
attgaacgca acccggcctt gcagaaactg tcgagtgaat ccgtggttga cctgtttacc    1380
aaagtctgcg tcgacggcat cattacctcc aaaactaaat ctctgataga aggtagaaac    1440
aaagcgctga acctgcagtg tattaaagtg aaaaacaatc ggctgcctta tgtagcagat    1500
aaagatagca ttagtcagga gattttcgaa aataaaatta tcactgacga aaccaatgtt    1560
cagaattatt cagataaatt ttcactggac gaaagcatct tagatggcca agttccgatt    1620
aacccggaaa ttgttgatcc gttactgccg aacgtgaata tggaaccgtt aaacctccct    1680
ggcgaagaga tcgtatttta tgatgacatt acgaaatatg tggactacct taattcttat    1740
tactatttgg aaagccagaa actgtccaat aacgtggaaa acattactct gaccacaagc    1800
gtggaagagg ctttaggcta ctcaaataag atttatacct tcctcccgtc gctggcggaa    1860
aaagtaaata aggtgtgca ggctggtctg ttcctcaact gggcgaatga agttgtcgaa    1920
gactttacca cgaatattat gaaaaaggat accctggata aaatctccga cgtctcggtt    1980
attatcccat atattggccc tgcgttaaat atcggtaata gtgcgctgcg ggggaatttt    2040
aaccaggcct ttgctaccgc gggcgtcgcg ttcctcctgg agggctttcc tgaatttact    2100
atcccggcgc tcggtgtttt tacattttac tcttccatcc aggagcgtga gaaaattatc    2160
aaaaccatcg aaaactgcct ggagcagcgg gtgaaacgct ggaaagattc ttatcaatgg    2220
atggtgtcaa actggttatc tcgcatcacg acccaattca accatattaa ttaccagatg    2280
tatgatagtc tgtcgtacca agctgacgcc attaaagcca aaattgatct ggaatataaa    2340
aagtactctg gtagcgataa ggagaacatc aaaagccagg tggagaacct taagaatagt    2400
ctggatgtga aaatctctga agctatgaat aacattaaca aattcattcg tgaatgttcg    2460
gtgacgtacc tgttcaagaa tatgctgcca aaagttattg atgaactgaa taaatttgat    2520
ctgcgtacca aaaccgaact tatcaacctc atcgactccc acaacattat ccttgtgggc    2580
gaagtggatc gtctgaaggc caaagtaaac gagagctttg aaaatacgat gccgtttaat    2640 atttttttcat ataccaataa ctccttgctg aaagatatca tcaatgaata tttcaatcta    2700
gaatgtggcg gtggcggtag catcgaaggt cgtcacgtgg atgcgatctt cactcagtct    2760
taccgtaaag ttctggcgca gctgagcgct cgtaaactgc tgcaggatat cctgaaccgt    2820
cagcagggtg aacgtaacca ggaacagggc gctggcggtg ggggtagttg cggcggtggc    2880
ggttcgcacg tggatgcgat cttcactcag tcttaccgta aagttctggc gcagctgagc    2940
gctcgtaaac tgctgcagga tatcctgaac cgtcagcagg gtgaacgtaa ccaggaacag    3000
ggcgcttgat aa                                                        3012
```

<210> SEQ ID NO 12
<211> LENGTH: 1002
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met His His His His His His His His His Gly Ser Ser Asn Asn

-continued

```
1               5                   10                  15
Asn Asn Asn Asn Asn Asn Asn Gly Ser Met Thr Trp Pro Val Lys
                20                  25                  30
Asp Phe Asn Tyr Ser Asp Pro Val Asn Asp Asn Asp Ile Leu Tyr Leu
                35                  40                  45
Arg Ile Pro Gln Asn Lys Leu Ile Thr Thr Pro Val Lys Ala Phe Met
    50                  55                  60
Ile Thr Gln Asn Ile Trp Val Ile Pro Glu Arg Phe Ser Ser Asp Thr
65                  70                  75                  80
Asn Pro Ser Leu Ser Lys Pro Pro Arg Pro Thr Ser Lys Tyr Gln Ser
                85                  90                  95
Tyr Tyr Asp Pro Ser Tyr Leu Ser Thr Asp Glu Gln Lys Asp Thr Phe
                100                 105                 110
Leu Lys Gly Ile Ile Lys Leu Phe Lys Arg Ile Asn Glu Arg Asp Ile
                115                 120                 125
Gly Lys Lys Leu Ile Asn Tyr Leu Val Val Gly Ser Pro Phe Met Gly
    130                 135                 140
Asp Ser Ser Thr Pro Glu Asp Thr Phe Asp Phe Thr Arg His Thr Thr
145                 150                 155                 160
Asn Ile Ala Val Glu Lys Phe Glu Asn Gly Ser Trp Lys Val Thr Asn
                165                 170                 175
Ile Ile Thr Pro Ser Val Leu Ile Phe Gly Pro Leu Pro Asn Ile Leu
                180                 185                 190
Asp Tyr Thr Ala Ser Leu Thr Leu Gln Gly Gln Gln Ser Asn Pro Ser
                195                 200                 205
Phe Glu Gly Phe Gly Thr Leu Ser Ile Leu Lys Val Ala Pro Glu Phe
                210                 215                 220
Leu Leu Thr Phe Ser Asp Val Thr Ser Asn Gln Ser Ser Ala Val Leu
225                 230                 235                 240
Gly Lys Ser Ile Phe Cys Met Asp Pro Val Ile Ala Leu Met His Glu
                245                 250                 255
Leu Thr His Ser Leu His Gln Leu Tyr Gly Ile Asn Ile Pro Ser Asp
                260                 265                 270
Lys Arg Ile Arg Pro Gln Val Ser Glu Gly Phe Phe Ser Gln Asp Gly
                275                 280                 285
Pro Asn Val Gln Phe Glu Glu Leu Tyr Thr Phe Gly Gly Leu Asp Val
                290                 295                 300
Glu Ile Ile Pro Gln Ile Glu Arg Ser Gln Leu Arg Glu Lys Ala Leu
305                 310                 315                 320
Gly His Tyr Lys Asp Ile Ala Lys Arg Leu Asn Asn Ile Asn Lys Thr
                325                 330                 335
Ile Pro Ser Ser Trp Ile Ser Asn Ile Asp Lys Tyr Lys Lys Ile Phe
                340                 345                 350
Ser Glu Lys Tyr Asn Phe Asp Lys Asp Asn Thr Gly Asn Phe Val Val
                355                 360                 365
Asn Ile Asp Lys Phe Asn Ser Leu Tyr Ser Asp Leu Thr Asn Val Met
                370                 375                 380
Ser Glu Val Val Tyr Ser Ser Gln Tyr Asn Val Lys Asn Arg Thr His
385                 390                 395                 400
Tyr Phe Ser Arg His Tyr Leu Pro Val Phe Ala Asn Ile Leu Asp Asp
                405                 410                 415
Asn Ile Tyr Thr Ile Arg Asp Gly Phe Asn Leu Thr Asn Lys Gly Phe
                420                 425                 430
```

```
Asn Ile Glu Asn Ser Gly Gln Asn Ile Glu Arg Asn Pro Ala Leu Gln
            435                 440                 445

Lys Leu Ser Ser Glu Ser Val Val Asp Leu Phe Thr Lys Val Cys Val
    450                 455                 460

Asp Gly Ile Ile Thr Ser Lys Thr Lys Ser Leu Ile Glu Gly Arg Asn
465                 470                 475                 480

Lys Ala Leu Asn Leu Gln Cys Ile Lys Val Lys Asn Asn Arg Leu Pro
                485                 490                 495

Tyr Val Ala Asp Lys Asp Ser Ile Ser Gln Glu Ile Phe Glu Asn Lys
                500                 505                 510

Ile Ile Thr Asp Glu Thr Asn Val Gln Asn Tyr Ser Asp Lys Phe Ser
            515                 520                 525

Leu Asp Glu Ser Ile Leu Asp Gly Gln Val Pro Ile Asn Pro Glu Ile
            530                 535                 540

Val Asp Pro Leu Leu Pro Asn Val Asn Met Glu Pro Leu Asn Leu Pro
545                 550                 555                 560

Gly Glu Glu Ile Val Phe Tyr Asp Asp Ile Thr Lys Tyr Val Asp Tyr
                565                 570                 575

Leu Asn Ser Tyr Tyr Leu Glu Ser Gln Lys Leu Ser Asn Asn Val
                580                 585                 590

Glu Asn Ile Thr Leu Thr Thr Ser Val Glu Glu Ala Leu Gly Tyr Ser
            595                 600                 605

Asn Lys Ile Tyr Thr Phe Leu Pro Ser Leu Ala Glu Lys Val Asn Lys
            610                 615                 620

Gly Val Gln Ala Gly Leu Phe Leu Asn Trp Ala Asn Glu Val Val Glu
625                 630                 635                 640

Asp Phe Thr Thr Asn Ile Met Lys Lys Asp Thr Leu Asp Lys Ile Ser
                645                 650                 655

Asp Val Ser Val Ile Ile Pro Tyr Ile Gly Pro Ala Leu Asn Ile Gly
                660                 665                 670

Asn Ser Ala Leu Arg Gly Asn Phe Asn Gln Ala Phe Ala Thr Ala Gly
            675                 680                 685

Val Ala Phe Leu Leu Glu Gly Phe Pro Glu Phe Thr Ile Pro Ala Leu
            690                 695                 700

Gly Val Phe Thr Phe Tyr Ser Ser Ile Gln Glu Arg Glu Lys Ile Ile
705                 710                 715                 720

Lys Thr Ile Glu Asn Cys Leu Glu Gln Arg Val Lys Arg Trp Lys Asp
                725                 730                 735

Ser Tyr Gln Trp Met Val Ser Asn Trp Leu Ser Arg Ile Thr Thr Gln
                740                 745                 750

Phe Asn His Ile Asn Tyr Gln Met Tyr Asp Ser Leu Ser Tyr Gln Ala
                755                 760                 765

Asp Ala Ile Lys Ala Lys Ile Asp Leu Glu Tyr Lys Lys Tyr Ser Gly
            770                 775                 780

Ser Asp Lys Glu Asn Ile Lys Ser Gln Val Glu Asn Leu Lys Asn Ser
785                 790                 795                 800

Leu Asp Val Lys Ile Ser Glu Ala Met Asn Asn Ile Asn Lys Phe Ile
                805                 810                 815

Arg Glu Cys Ser Val Thr Tyr Leu Phe Lys Asn Met Leu Pro Lys Val
                820                 825                 830

Ile Asp Glu Leu Asn Lys Phe Asp Leu Arg Thr Lys Thr Glu Leu Ile
                835                 840                 845
```

```
Asn Leu Ile Asp Ser His Asn Ile Ile Leu Val Gly Glu Val Asp Arg
850                 855                 860

Leu Lys Ala Lys Val Asn Glu Ser Phe Glu Asn Thr Met Pro Phe Asn
865                 870                 875                 880

Ile Phe Ser Tyr Thr Asn Asn Ser Leu Leu Lys Asp Ile Ile Asn Glu
            885                 890                 895

Tyr Phe Asn Leu Glu Cys Gly Gly Gly Ser Ile Glu Gly Arg His
        900                 905                 910

Val Asp Ala Ile Phe Thr Gln Ser Tyr Arg Lys Val Leu Ala Gln Leu
            915                 920                 925

Ser Ala Arg Lys Leu Leu Gln Asp Ile Leu Asn Arg Gln Gln Gly Glu
930                 935                 940

Arg Asn Gln Glu Gln Gly Ala Gly Gly Gly Ser Cys Gly Gly Gly
945                 950                 955                 960

Gly Ser His Val Asp Ala Ile Phe Thr Gln Ser Tyr Arg Lys Val Leu
            965                 970                 975

Ala Gln Leu Ser Ala Arg Lys Leu Leu Gln Asp Ile Leu Asn Arg Gln
            980                 985                 990

Gln Gly Glu Arg Asn Gln Glu Gln  Gly Ala
            995                 1000

<210> SEQ ID NO 13
<211> LENGTH: 2814
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgcatcacc atcaccatca ccatcaccat catgggagct cgaacaataa caacaataac      60
aataacaata acggatccat gacgtggcca gttaaggatt tcaactactc agatcctgta     120
aatgacaacg atattctgta ccttcgcatt ccacaaaata aactgatcac cacaccagtc     180
aaagcattca tgattactca aaacatttgg gtcattccag aacgcttttc tagtgacaca     240
aatccgagtt tatctaaacc tccgcgtccg acgtccaaat atcagagcta ttacgatccc     300
tcatatctca gtacggacga acaaaaagat actttcctta aaggtatcat taaactgttt     360
aagcgtatta tgagcgcga tatcgggaaa agttgatta ttatcttgt tgtgggttcc        420 ccgttcatgg gcgatagctc taccccgaa gacactttg atttacccg tcatacgaca       480 aacatcgcgg tagagaagtt tgagaacgga tcgtggaaag tcacaaacat cattacacct     540
agcgtcttaa tttttggtcc gctgccaaac atcttagatt atacagccag cctgactttg     600 cagggcaac agtcgaatcc gagtttcgaa ggttttggta ccctgagcat tctgaaagtt     660
gccccggaat ttctgctcac ttttcagat gtcaccagca accagagctc agcagtatta     720
ggaaagtcaa ttttttgcat ggacccggtt attgcactga tgcacgaact gacgcactct     780
ctgcatcaac tgtatgggat caacatcccc agtgacaaac gtattcgtcc ccaggtgtct     840
gaaggatttt tctcacagga tgggccgaac gtccagttcg aagagttgta cttttcgga     900 ggcctggacg tagagatcat tccccagatt gagcgcagtc agctgcgtga aaggcattg     960 ggccattata aggatattgc aaaacgcctg aataacatta caaaacgat ccatcttcg     1020 tggatctcga atattgataa atataagaaa atttttagcg agaaatataa ttttgataaa    1080
gataatacag gtaactttgt ggttaacatt gacaaattca actcccttta cagtgatttg    1140
```

-continued
acgaatgtaa tgagcgaagt tgtgtatagt tcccaataca acgttaagaa tcgtacccat 1200
tacttctctc gtcactacct gccggttttc gcgaacatcc ttgacgataa tatttacact 1260
attcgtgacg gctttaactt gaccaacaag ggcttcaata ttgaaaattc aggccagaac 1320
attgaacgca acccggcctt gcagaaactg tcgagtgaat ccgtggttga cctgtttacc 1380
aaagtctgcg tcgacggcat cattacctcc aaaactaaat ctctgataga aggtagaaac 1440
aaagcgctga acctgcagtg tattaaagtg aaaaacaatc ggctgcctta tgtagcagat 1500
aaagatagca ttagtcagga gattttcgaa aataaaatta tcactgacga aaccaatgtt 1560
cagaattatt cagataaatt ttcactggac gaaagcatct tagatggcca agttccgatt 1620
aacccggaaa ttgttgatcc gttactgccg aacgtgaata tggaaccgtt aaacctccct 1680
ggcgaagaga tcgtatttta tgatgacatt acgaaatatg tggactacct taattcttat 1740
tactatttgg aaagccagaa actgtccaat aacgtggaaa acattactct gaccacaagc 1800
gtggaagagg ctttaggcta ctcaaataag atttatacct tcctcccgtc gctggcggaa 1860
aaagtaaata aaggtgtgca ggctggtctg ttcctcaact gggcgaatga agttgtcgaa 1920
gactttacca cgaatattat gaaaaaggat accctggata aaatctccga cgtctcggtt 1980
attatcccat atattggccc tgcgttaaat atcggtaata gtgcgctgcg gggggaattt 2040
aaccaggcct ttgctaccgc gggcgtcgcg ttcctcctgg agggctttcc tgaatttact 2100
atcccggcgc tcggtgtttt tacattttac tcttccatcc aggagcgtga gaaaattatc 2160
aaaaccatcg aaaactgcct ggagcagcgg gtgaaacgct ggaaagattc ttatcaatgg 2220
atggtgtcaa actggttatc tcgcatcacg acccaattca accatattaa ttaccagatg 2280
tatgatagtc tgtcgtacca agctgacgcc attaaagcca aaattgatct ggaatataaa 2340
aagtactctg gtagcgataa ggagaacatc aaaagccagg tggagaacct taagaatagt 2400
ctggatgtga aaatctctga agctatgaat aacattaaca aattcattcg tgaatgttcg 2460
gtgacgtacc tgttcaagaa tatgctgcca aaagttattg atgaactgaa taaatttgat 2520
ctgcgtacca aaaccgaact tatcaacctc atcgactccc acaacattat ccttgtgggc 2580
gaagtggatc gtctgaaggc caaagtaaac gagagctttg aaaatacgat gccgtttaat 2640
attttttcat ataccaataa ctccttgctg aaagatatca tcaatgaata tttcaatcta 2700
gaatgtggtg gcggtggctc tggtggcggc ggttctattg aaggtcgcgg tggcggtggc 2760
tctggtggcg gcggttctca gcactggtcc tattgcctgc gccctggttg ataa 2814

<210> SEQ ID NO 14
<211> LENGTH: 936
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Met His His His His His His His His His His Gly Ser Ser Asn Asn
1 5 10 15

Asn Asn Asn Asn Asn Asn Asn Asn Gly Ser Met Thr Trp Pro Val Lys
20 25 30

Asp Phe Asn Tyr Ser Asp Pro Val Asn Asp Asn Asp Ile Leu Tyr Leu
35 40 45

Arg Ile Pro Gln Asn Lys Leu Ile Thr Thr Pro Val Lys Ala Phe Met
50 55 60

```
Ile Thr Gln Asn Ile Trp Val Ile Pro Glu Arg Phe Ser Ser Asp Thr
 65                  70                  75                  80

Asn Pro Ser Leu Ser Lys Pro Pro Arg Pro Thr Ser Lys Tyr Gln Ser
                 85                  90                  95

Tyr Tyr Asp Pro Ser Tyr Leu Ser Thr Asp Glu Gln Lys Asp Thr Phe
            100                 105                 110

Leu Lys Gly Ile Ile Lys Leu Phe Lys Arg Ile Asn Glu Arg Asp Ile
        115                 120                 125

Gly Lys Lys Leu Ile Asn Tyr Leu Val Val Gly Ser Pro Phe Met Gly
    130                 135                 140

Asp Ser Ser Thr Pro Glu Asp Thr Phe Asp Phe Thr Arg His Thr Thr
145                 150                 155                 160

Asn Ile Ala Val Glu Lys Phe Glu Asn Gly Ser Trp Lys Val Thr Asn
                165                 170                 175

Ile Ile Thr Pro Ser Val Leu Ile Phe Gly Pro Leu Pro Asn Ile Leu
            180                 185                 190

Asp Tyr Thr Ala Ser Leu Thr Leu Gln Gly Gln Gln Ser Asn Pro Ser
        195                 200                 205

Phe Glu Gly Phe Gly Thr Leu Ser Ile Leu Lys Val Ala Pro Glu Phe
    210                 215                 220

Leu Leu Thr Phe Ser Asp Val Thr Ser Asn Gln Ser Ser Ala Val Leu
225                 230                 235                 240

Gly Lys Ser Ile Phe Cys Met Asp Pro Val Ile Ala Leu Met His Glu
                245                 250                 255

Leu Thr His Ser Leu His Gln Leu Tyr Gly Ile Asn Ile Pro Ser Asp
            260                 265                 270

Lys Arg Ile Arg Pro Gln Val Ser Glu Gly Phe Phe Ser Gln Asp Gly
        275                 280                 285

Pro Asn Val Gln Phe Glu Glu Leu Tyr Thr Phe Gly Gly Leu Asp Val
    290                 295                 300

Glu Ile Ile Pro Gln Ile Glu Arg Ser Gln Leu Arg Glu Lys Ala Leu
305                 310                 315                 320

Gly His Tyr Lys Asp Ile Ala Lys Arg Leu Asn Asn Ile Asn Lys Thr
                325                 330                 335

Ile Pro Ser Ser Trp Ile Ser Asn Ile Asp Lys Tyr Lys Lys Ile Phe
            340                 345                 350

Ser Glu Lys Tyr Asn Phe Asp Lys Asp Asn Thr Gly Asn Phe Val Val
        355                 360                 365

Asn Ile Asp Lys Phe Asn Ser Leu Tyr Ser Asp Leu Thr Asn Val Met
    370                 375                 380

Ser Glu Val Val Tyr Ser Ser Gln Tyr Asn Val Lys Asn Arg Thr His
385                 390                 395                 400

Tyr Phe Ser Arg His Tyr Leu Pro Val Phe Ala Asn Ile Leu Asp Asp
                405                 410                 415

Asn Ile Tyr Thr Ile Arg Asp Gly Phe Asn Leu Thr Asn Lys Gly Phe
            420                 425                 430

Asn Ile Glu Asn Ser Gly Gln Asn Ile Glu Arg Asn Pro Ala Leu Gln
        435                 440                 445

Lys Leu Ser Ser Glu Ser Val Val Asp Leu Phe Thr Lys Val Cys Val
    450                 455                 460

Asp Gly Ile Ile Thr Ser Lys Thr Lys Ser Leu Ile Glu Gly Arg Asn
465                 470                 475                 480

Lys Ala Leu Asn Leu Gln Cys Ile Lys Val Lys Asn Asn Arg Leu Pro
```

```
                485                 490                 495
Tyr Val Ala Asp Lys Asp Ser Ile Ser Gln Glu Ile Phe Glu Asn Lys
            500                 505                 510
Ile Ile Thr Asp Glu Thr Asn Val Gln Asn Tyr Ser Asp Lys Phe Ser
            515                 520                 525
Leu Asp Glu Ser Ile Leu Asp Gly Gln Val Pro Ile Asn Pro Glu Ile
            530                 535                 540
Val Asp Pro Leu Leu Pro Asn Val Asn Met Glu Pro Leu Asn Leu Pro
545                 550                 555                 560
Gly Glu Glu Ile Val Phe Tyr Asp Asp Ile Thr Lys Tyr Val Asp Tyr
                565                 570                 575
Leu Asn Ser Tyr Tyr Leu Glu Ser Gln Lys Leu Ser Asn Asn Val
            580                 585                 590
Glu Asn Ile Thr Leu Thr Thr Ser Val Glu Glu Ala Leu Gly Tyr Ser
                595                 600                 605
Asn Lys Ile Tyr Thr Phe Leu Pro Ser Leu Ala Glu Lys Val Asn Lys
            610                 615                 620
Gly Val Gln Ala Gly Leu Phe Leu Asn Trp Ala Asn Glu Val Val Glu
625                 630                 635                 640
Asp Phe Thr Thr Asn Ile Met Lys Lys Asp Thr Leu Asp Lys Ile Ser
                    645                 650                 655
Asp Val Ser Val Ile Pro Tyr Ile Gly Pro Ala Leu Asn Ile Gly
                660                 665                 670
Asn Ser Ala Leu Arg Gly Asn Phe Asn Gln Ala Phe Ala Thr Ala Gly
            675                 680                 685
Val Ala Phe Leu Leu Glu Gly Phe Pro Glu Phe Thr Ile Pro Ala Leu
            690                 695                 700
Gly Val Phe Thr Phe Tyr Ser Ser Ile Gln Arg Glu Lys Ile Ile
705                 710                 715                 720
Lys Thr Ile Glu Asn Cys Leu Glu Gln Arg Val Lys Arg Trp Lys Asp
                    725                 730                 735
Ser Tyr Gln Trp Met Val Ser Asn Trp Leu Ser Arg Ile Thr Thr Gln
                740                 745                 750
Phe Asn His Ile Asn Tyr Gln Met Tyr Asp Ser Leu Ser Tyr Gln Ala
            755                 760                 765
Asp Ala Ile Lys Ala Lys Ile Asp Leu Glu Tyr Lys Lys Tyr Ser Gly
            770                 775                 780
Ser Asp Lys Glu Asn Ile Lys Ser Gln Val Glu Asn Leu Lys Asn Ser
785                 790                 795                 800
Leu Asp Val Lys Ile Ser Glu Ala Met Asn Asn Ile Asn Lys Phe Ile
                805                 810                 815
Arg Glu Cys Ser Val Thr Tyr Leu Phe Lys Asn Met Leu Pro Lys Val
                820                 825                 830
Ile Asp Glu Leu Asn Lys Phe Asp Leu Arg Thr Lys Thr Glu Leu Ile
            835                 840                 845
Asn Leu Ile Asp Ser His Asn Ile Ile Leu Val Gly Glu Val Asp Arg
850                 855                 860
Leu Lys Ala Lys Val Asn Glu Ser Phe Glu Asn Thr Met Pro Phe Asn
865                 870                 875                 880
Ile Phe Ser Tyr Thr Asn Asn Ser Leu Leu Lys Asp Ile Ile Asn Glu
                885                 890                 895
Tyr Phe Asn Leu Glu Cys Gly Gly Gly Ser Gly Gly Gly Ser
                900                 905                 910
```

```
Ile Glu Gly Arg Gly Gly Gly Ser Gly Gly Gly Ser Gln His
    915                 920                 925

Trp Ser Tyr Cys Leu Arg Pro Gly
    930                 935

<210> SEQ ID NO 15
<211> LENGTH: 2793
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgcatcacc atcaccatca ccatcaccat catgggagct cgaacaataa caacaataac     60
aataacaata acggatccat ggagttcgtt aacaaacagt tcaactataa agacccagtt    120
aacggtgttg acattgctta catcaaaatc ccgaacgctg ccagatgca gccggtaaag    180 gcattcaaaa tccacaacaa atctgggtt atcccggaac gtgataccttt actaacccg    240 gaagaaggtg acctgaaccc gccaccggaa gcgaaacagg tgccggtatc ttactatgac    300
tccacctacc tgtctaccga taacgaaaag gacaactacc tgaaaggtgt tactaaactg    360
ttcgagcgta tttactccac cgacctgggc cgtatgctgc tgactagcat cgttcgcggt    420
atcccgttct ggggcggttc taccatcgat accgaactga agtaatcga cactaactgc    480 atcaacgtta ttcagccgga cggttcctat cgttccgaag aactgaaccct ggtgatcatc    540 ggcccgtctg ctgatatcat ccagttcgag tgtaagagct ttggtcacga agttctgaac    600
ctcacccgta acggctacgg ttccactcag tacatccgtt tctctccgga cttcaccttc    660
ggttttgaag aatccctgga agtagacacg aacccactgc tgggcgctgg taaattcgca    720
actgatcctg cggttaccct ggctcacgaa ctgattcatg caggccaccg cctgtacggt    780
atcgccatca atccgaaccg tgtcttcaaa gttaacacca acgcgtatta cgagatgtcc    840
ggtctggaag ttagcttcga agaactgcgt acttttggcg gtcacgacgc taaattcatc    900
gactctctgc aagaaaacga gttccgtctg tactactata caagttcaa agatatcgca    960 tccaccctga caaagcgaa atccatcgtg gtaccactg cttctctcca gtacatgaag   1020
aacgttttta agaaaaata cctgctcagc gaagacacct ccggcaaatt ctctgtagac   1080
aagttgaaat tcgataaact ttacaaaatg ctgactgaaa tttacaccga agacaacttc   1140
gttaagttct ttaaagttct gaaccgcaaa acctatctga acttcgacaa ggcagtattc   1200
aaaatcaaca tcgtgccgaa agttaactac actatctacg atggtttcaa cctgcgtaac   1260
accaacctgg ctgctaattt taacggccag aacacggaaa tcaacaacat gaacttcaca   1320
aaactgaaaa acttcactgg tctgttcgag ttttacaagc tgctgtgcgt cgacggcatc   1380
attacctcca aaactaaatc tctgatagaa ggtagaaaca aagcgctgaa cgacctctgt   1440
atcaaggtta caactgggga tttattcttc agcccgagtg aagacaactt caccaacgac   1500
ctgaacaaag gtgaagaaat cacctcagat actaacatcg aagcagccga agaaacatc   1560 tcgctggacc tgatccagca gtactacctg accttaatt tcgacaacga gccggaaaac   1620
atttctatcg aaaacctgag ctctgatatc atcggccagc tggaactgat gccgaacatc   1680 gaacgttttcc caaacggtaa aaagtacgag ctggacaaat ataccatgtt ccactacctg   1740
cgcgcgcagg aatttgaaca cggcaaatcc cgtatcgcac tgactaactc cgttaacgaa   1800
gctctgctca acccgtcccg tgtatacacc ttcttctcta gcgactacgt gaaaaaggtc   1860
```

-continued

```
aacaaagcga ctgaagctgc aatgttcttg ggttgggttg aacagcttgt ttatgatttt    1920
accgacgaga cgtccgaagt atctactacc gacaaaattg cggatatcac tatcatcatc    1980
ccgtacatcg gtccggctct gaacattggc aacatgctgt acaaagacga cttcgttggc    2040
gcactgatct tctccggtgc ggtgatcctg ctggagttca tcccggaaat cgccatcccg    2100
gtactgggca cctttgctct ggtttcttac attgcaaaca aggttctgac tgtacaaacc    2160
atcgacaacg cgctgagcaa acgtaacgaa aaatgggatg aagtttacaa atatatcgtg    2220
accaactggc tggctaaggt taatactcag atcgacctca tccgcaaaaa aatgaaagaa    2280
gcactggaaa accaggcgga agctaccaag gcaatcatta actaccagta caaccagtac    2340
accgaggaag aaaaaaacaa catcaacttc aacatcgacg atctgtcctc taaactgaac    2400
gaatccatca caaagctat gatcaacatc aacaagttcc tgaaccagtg ctctgtaagc    2460
tatctgatga actccatgat cccgtacggt gttaaacgtc tggaggactt cgatgcgtct    2520
ctgaaagacg ccctgctgaa atacatttac gacaaccgtg gcactctgat cggtcaggtt    2580
gatcgtctga aggacaaagt gaacaatacc ttatcgaccg acatcccttt tcagctcagt    2640
aaatatgtcg ataaccaacg cctttttgtcc acttgtggcg gtggcggtag catcgaaggt    2700
cgtgttccat taccagcagg aggaggaaca gtattgacta aaatgtatcc atgcggaaat    2760
cactgggcag tgggacatct aatgggatga taa                                  2793
```

<210> SEQ ID NO 16
<211> LENGTH: 929
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met His His His His His His His His Gly Ser Ser Asn Asn
1               5                  10                  15

Asn Asn Asn Asn Asn Asn Asn Asn Gly Ser Met Glu Phe Val Asn Lys
            20                  25                  30

Gln Phe Asn Tyr Lys Asp Pro Val Asn Gly Val Asp Ile Ala Tyr Ile
        35                  40                  45

Lys Ile Pro Asn Ala Gly Gln Met Gln Pro Val Lys Ala Phe Lys Ile
    50                  55                  60

His Asn Lys Ile Trp Val Ile Pro Glu Arg Asp Thr Phe Thr Asn Pro
65                  70                  75                  80

Glu Glu Gly Asp Leu Asn Pro Pro Glu Ala Lys Gln Val Pro Val
                85                  90                  95

Ser Tyr Tyr Asp Ser Thr Tyr Leu Ser Thr Asp Asn Glu Lys Asp Asn
            100                 105                 110

Tyr Leu Lys Gly Val Thr Lys Leu Phe Glu Arg Ile Tyr Ser Thr Asp
        115                 120                 125

Leu Gly Arg Met Leu Leu Thr Ser Ile Val Arg Gly Ile Pro Phe Trp
    130                 135                 140

Gly Gly Ser Thr Ile Asp Thr Glu Leu Lys Val Ile Asp Thr Asn Cys
145                 150                 155                 160

Ile Asn Val Ile Gln Pro Asp Gly Ser Tyr Arg Ser Glu Glu Leu Asn
                165                 170                 175

Leu Val Ile Ile Gly Pro Ser Ala Asp Ile Ile Gln Phe Glu Cys Lys
            180                 185                 190
```

-continued

Ser Phe Gly His Glu Val Leu Asn Leu Thr Arg Asn Gly Tyr Gly Ser
            195                 200                 205

Thr Gln Tyr Ile Arg Phe Ser Pro Asp Phe Thr Phe Gly Phe Glu Glu
        210                 215                 220

Ser Leu Glu Val Asp Thr Asn Pro Leu Gly Ala Gly Lys Phe Ala
225                 230                 235                 240

Thr Asp Pro Ala Val Thr Leu Ala His Glu Leu Ile His Ala Gly His
                245                 250                 255

Arg Leu Tyr Gly Ile Ala Ile Asn Pro Asn Arg Val Phe Lys Val Asn
            260                 265                 270

Thr Asn Ala Tyr Tyr Glu Met Ser Gly Leu Glu Val Ser Phe Glu Glu
        275                 280                 285

Leu Arg Thr Phe Gly Gly His Asp Ala Lys Phe Ile Asp Ser Leu Gln
    290                 295                 300

Glu Asn Glu Phe Arg Leu Tyr Tyr Tyr Asn Lys Phe Lys Asp Ile Ala
305                 310                 315                 320

Ser Thr Leu Asn Lys Ala Lys Ser Ile Val Gly Thr Thr Ala Ser Leu
                325                 330                 335

Gln Tyr Met Lys Asn Val Phe Lys Glu Lys Tyr Leu Leu Ser Glu Asp
            340                 345                 350

Thr Ser Gly Lys Phe Ser Val Asp Lys Leu Lys Phe Asp Lys Leu Tyr
        355                 360                 365

Lys Met Leu Thr Glu Ile Tyr Thr Glu Asp Asn Phe Val Lys Phe Phe
    370                 375                 380

Lys Val Leu Asn Arg Lys Thr Tyr Leu Asn Phe Asp Lys Ala Val Phe
385                 390                 395                 400

Lys Ile Asn Ile Val Pro Lys Val Asn Tyr Thr Ile Tyr Asp Gly Phe
                405                 410                 415

Asn Leu Arg Asn Thr Asn Leu Ala Ala Asn Phe Asn Gly Gln Asn Thr
            420                 425                 430

Glu Ile Asn Asn Met Asn Phe Thr Lys Leu Lys Asn Phe Thr Gly Leu
        435                 440                 445

Phe Glu Phe Tyr Lys Leu Leu Cys Val Asp Gly Ile Ile Thr Ser Lys
    450                 455                 460

Thr Lys Ser Leu Ile Glu Gly Arg Asn Lys Ala Leu Asn Asp Leu Cys
465                 470                 475                 480

Ile Lys Val Asn Asn Trp Asp Leu Phe Phe Ser Pro Ser Glu Asp Asn
                485                 490                 495

Phe Thr Asn Asp Leu Asn Lys Gly Glu Ile Thr Ser Asp Thr Asn
            500                 505                 510

Ile Glu Ala Ala Glu Glu Asn Ile Ser Leu Asp Leu Ile Gln Gln Tyr
        515                 520                 525

Tyr Leu Thr Phe Asn Phe Asp Asn Glu Pro Glu Asn Ile Ser Ile Glu
    530                 535                 540

Asn Leu Ser Ser Asp Ile Ile Gly Gln Leu Glu Leu Met Pro Asn Ile
545                 550                 555                 560

Glu Arg Phe Pro Asn Gly Lys Lys Tyr Glu Leu Asp Lys Tyr Thr Met
                565                 570                 575

Phe His Tyr Leu Arg Ala Gln Glu Phe Glu His Gly Lys Ser Arg Ile
            580                 585                 590

Ala Leu Thr Asn Ser Val Asn Glu Ala Leu Leu Asn Pro Ser Arg Val
        595                 600                 605

```
Tyr Thr Phe Phe Ser Ser Asp Tyr Val Lys Lys Val Asn Lys Ala Thr
    610                 615                 620
Glu Ala Ala Met Phe Leu Gly Trp Val Glu Gln Leu Val Tyr Asp Phe
625                 630                 635                 640
Thr Asp Glu Thr Ser Glu Val Ser Thr Thr Asp Lys Ile Ala Asp Ile
                645                 650                 655
Thr Ile Ile Ile Pro Tyr Ile Gly Pro Ala Leu Asn Ile Gly Asn Met
            660                 665                 670
Leu Tyr Lys Asp Asp Phe Val Gly Ala Leu Ile Phe Ser Gly Ala Val
        675                 680                 685
Ile Leu Leu Glu Phe Ile Pro Glu Ile Ala Ile Pro Val Leu Gly Thr
    690                 695                 700
Phe Ala Leu Val Ser Tyr Ile Ala Asn Lys Val Leu Thr Val Gln Thr
705                 710                 715                 720
Ile Asp Asn Ala Leu Ser Lys Arg Asn Glu Lys Trp Asp Glu Val Tyr
                725                 730                 735
Lys Tyr Ile Val Thr Asn Trp Leu Ala Lys Val Asn Thr Gln Ile Asp
            740                 745                 750
Leu Ile Arg Lys Lys Met Lys Glu Ala Leu Glu Asn Gln Ala Glu Ala
        755                 760                 765
Thr Lys Ala Ile Ile Asn Tyr Gln Tyr Asn Gln Tyr Thr Glu Glu Glu
    770                 775                 780
Lys Asn Asn Ile Asn Phe Asn Ile Asp Asp Leu Ser Ser Lys Leu Asn
785                 790                 795                 800
Glu Ser Ile Asn Lys Ala Met Ile Asn Ile Asn Lys Phe Leu Asn Gln
                805                 810                 815
Cys Ser Val Ser Tyr Leu Met Asn Ser Met Ile Pro Tyr Gly Val Lys
            820                 825                 830
Arg Leu Glu Asp Phe Asp Ala Ser Leu Lys Asp Ala Leu Leu Lys Tyr
        835                 840                 845
Ile Tyr Asp Asn Arg Gly Thr Leu Ile Gly Gln Val Asp Arg Leu Lys
    850                 855                 860
Asp Lys Val Asn Asn Thr Leu Ser Thr Asp Ile Pro Phe Gln Leu Ser
865                 870                 875                 880
Lys Tyr Val Asp Asn Gln Arg Leu Leu Ser Thr Cys Gly Gly Gly Gly
                885                 890                 895
Ser Ile Glu Gly Arg Val Pro Leu Pro Ala Gly Gly Gly Thr Val Leu
            900                 905                 910
Thr Lys Met Tyr Pro Cys Gly Asn His Trp Ala Val Gly His Leu Met
        915                 920                 925
Gly

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Leu Ala Glu Ile Asp Gly Ile Glu Leu
1               5                   10

<210> SEQ ID NO 18
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Pro Leu Ala Glu Ile Asp Gly Ile Glu Leu Cys
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr His Ala Leu Trp His Thr
1               5

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Pro Phe Met Gln Cys Leu Cys Leu Ile Tyr Asp Ala Ser Cys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Asn Val Pro Pro Ile Phe Asn Asp Val Tyr Trp Ile Ala Phe
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Phe Arg Val Arg Pro Trp Tyr Gln Ser Thr Ser Gln Ser
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Asp Ser Ala Phe Val Thr Val Asp Trp Gly Arg Ser Met Ser Leu
```

```
1               5               10              15
Cys

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Glu Arg Ser Met Asn Phe
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Gly Leu Pro His Lys Phe
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Ser Gly Ala Ala Arg Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Pro His Lys Ser Met Pro
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Gln His Lys Ser Met Pro
1               5

<210> SEQ ID NO 29
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 29

Phe Ser Leu Ser Lys Pro Pro
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Ser Met Gln Leu Ser Thr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Thr Gln Ala Met Phe Gln
1               5

<210> SEQ ID NO 32
<211> LENGTH: 5
<212> TYPE: PRT
<213> ORGANISM: Unknown
<220> FEATURE:
<223> OTHER INFORMATION: Description of Unknown: Enterokinase
      sequence

<400> SEQUENCE: 32

Asp Asp Asp Asp Lys
1               5

<210> SEQ ID NO 33
<211> LENGTH: 4
<212> TYPE: PRT
<213> ORGANISM: Unknown
<220> FEATURE:
<223> OTHER INFORMATION: Description of Unknown: Factor Xa sequence

<400> SEQUENCE: 33

Ile Glu Gly Arg
1

<210> SEQ ID NO 34
<211> LENGTH: 4
<212> TYPE: PRT
<213> ORGANISM: Unknown
<220> FEATURE:
<223> OTHER INFORMATION: Description of Unknown: Factor Xa sequence

<400> SEQUENCE: 34

Ile Asp Gly Arg
1

<210> SEQ ID NO 35
```

```
<211> LENGTH: 7
<212> TYPE: PRT
<213> ORGANISM: Tobacco Etch virus

<400> SEQUENCE: 35

Glu Asn Leu Tyr Phe Gln Gly
1               5

<210> SEQ ID NO 36
<211> LENGTH: 6
<212> TYPE: PRT
<213> ORGANISM: Unknown
<220> FEATURE:
<223> OTHER INFORMATION: Description of Unknown: Thrombin sequence

<400> SEQUENCE: 36

Leu Val Pro Arg Gly Ser
1               5

<210> SEQ ID NO 37
<211> LENGTH: 8
<212> TYPE: PRT
<213> ORGANISM: Unknown
<220> FEATURE:
<223> OTHER INFORMATION: Description of Unknown: PreScission sequence

<400> SEQUENCE: 37

Leu Glu Val Leu Phe Gln Gly Pro
1               5

<210> SEQ ID NO 38
<211> LENGTH: 25
<212> TYPE: PRT
<213> ORGANISM: Clostridium botulinum

<400> SEQUENCE: 38

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 39
<211> LENGTH: 25
<212> TYPE: PRT
<213> ORGANISM: Clostridium botulinum

<400> SEQUENCE: 39

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 40
<211> LENGTH: 10
<212> TYPE: PRT
<213> ORGANISM: Clostridium botulinum

<400> SEQUENCE: 40

Cys Lys Ser Val Lys Ala Pro Gly Ile Cys
1               5                   10

<210> SEQ ID NO 41
<211> LENGTH: 17
<212> TYPE: PRT
<213> ORGANISM: Clostridium botulinum
```

-continued

```
<400> SEQUENCE: 41

Cys His Lys Ala Ile Asp Gly Arg Ser Leu Tyr Asn Lys Thr Leu Asp
1               5                   10                  15

Cys

<210> SEQ ID NO 42
<211> LENGTH: 14
<212> TYPE: PRT
<213> ORGANISM: Clostridium botulinum

<400> SEQUENCE: 42

Cys Leu Arg Leu Thr Lys Asn Ser Arg Asp Asp Ser Thr Cys
1               5                   10

<210> SEQ ID NO 43
<211> LENGTH: 15
<212> TYPE: PRT
<213> ORGANISM: Clostridium botulinum

<400> SEQUENCE: 43

Cys Lys Asn Ile Val Ser Val Lys Gly Ile Arg Lys Ser Ile Cys
1               5                   10                  15

<210> SEQ ID NO 44
<211> LENGTH: 17
<212> TYPE: PRT
<213> ORGANISM: Clostridium botulinum

<400> SEQUENCE: 44

Cys Lys Ser Val Ile Pro Arg Lys Gly Thr Lys Ala Pro Pro Arg Leu
1               5                   10                  15

Cys

<210> SEQ ID NO 45
<211> LENGTH: 15
<212> TYPE: PRT
<213> ORGANISM: Clostridium botulinum

<400> SEQUENCE: 45

Cys Lys Pro Val Met Tyr Lys Asn Thr Gly Lys Ser Glu Gln Cys
1               5                   10                  15

<210> SEQ ID NO 46
<211> LENGTH: 29
<212> TYPE: PRT
<213> ORGANISM: Clostridium tetani

<400> SEQUENCE: 46

Cys Lys Lys Ile Ile Pro Pro Thr Asn Ile Arg Glu Asn Leu Tyr Asn
1               5                   10                  15

Arg Thr Ala Ser Leu Thr Asp Leu Gly Gly Glu Leu Cys
            20                  25

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 47
```

```
His His His His His His
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His His His His His His His His His His
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asn Asn Asn Asn Asn Asn Asn Asn Asn Asn
1               5                   10

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Gly Gly Gly Ser
1               5

<210> SEQ ID NO 51
<211> LENGTH: 10
<212> TYPE: PRT
<213> ORGANISM: Unknown
<220> FEATURE:
<223> OTHER INFORMATION: Description of Unknown: GnRH sequence

<400> SEQUENCE: 51

Gln His Trp Ser Tyr Cys Leu Arg Pro Gly
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Ser Cys Gly Gly Gly Gly Ser
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
          peptide

<400> SEQUENCE: 53

Gly Gly Gly Gly Ser Ile Glu Gly Arg Gly Gly Gly Gly Ser
1               5                   10

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Pro Leu Pro Ala Gly Gly Thr Val Leu Thr Lys Met Tyr Pro
1               5                   10                  15

Cys Gly Asn His Trp Ala Val Gly His Leu Met Gly
                20                  25
```

THERAPEUTIC FUSION PROTEINS

CROSS-REFERENCE TO RELATED APPLICATIONS

This application is a division of U.S. application Ser. No. 14/117,286, now U.S. Pat. No. 10,081,803, which is a U.S. national stage filing of International Patent Application No. PCT/GB2012/051104, filed on May 16, 2012, which claims the priority of United Kingdom Application No. 11081018.0, filed May 16, 2011.

REFERENCE TO SEQUENCE LISTING

The instant application contains a Sequence Listing that has been submitted electronically in ASCII format and is hereby incorporated by reference in its entirety. Said ASCII copy, created on Nov. 13, 2018, is named 285623_ST25.txt and is 105,172 bytes in size.

BACKGROUND OF THE INVENTION

The present invention relates to the construction of a new class of Targeted Secretion Inhibitors (TSIs), to a method for the activation thereof, and to the activated product.

Non-cytotoxic proteases are a well-recognised group of proteases, which act on target cells by incapacitating cellular function. Importantly, non-cytotoxic proteases do not kill the target cells upon which they act. Some of the best known examples of non-cytotoxic proteases include clostridial neurotoxins (e.g. botulinum neurotoxin, which is marketed under names such as Dysport™, Neurobloc™, and Botox™) and IgA proteases.

Non-cytotoxic proteases act by proteolytically-cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle formation, and thus to secretion of molecules via vesicle transport from a cell. Accordingly, once delivered to a desired target cell, the non-cytotoxic protease is capable of inhibiting cellular secretion from the target cell.

Non-cytotoxic proteases may be employed in their native or substantially native forms (i.e. as holotoxins, such as is the case with Dysport™, Neurobloc™, and Botox™), in which case targeting of the proteases to specific cell-types is reliant on (i) localised administration of the protease and/or (ii) the inherent binding ability of the native protease. Alternatively, non-cytotoxic proteases may be employed in a re-targeted form in which the native protease is modified to include an exogenous ligand known as a Targeting Moiety (TM). The TM is selected to provide binding specificity for a desired target cell, and, as part of the re-targeting process, the native binding portion of the non-cytotoxic protease may be removed.

The present Applicant has pioneered the concept and development of clostridial neurotoxin-based re-targeting technology, and the resulting fusion proteins are known as Targeted Secretion Inhibitors (TSIs).

TM replacement may be effected by conventional chemical conjugation techniques, which are well known to a skilled person. In this regard, reference is made to Hermanson, G. T. (1996), Bioconjugate techniques, Academic Press, and to Wong, S. S. (1991), Chemistry of protein conjugation and cross-linking, CRC Press.

Chemical conjugation is, however, often imprecise. For example, following conjugation, a TM may become joined to the remainder of the conjugate at more than one attachment site. Chemical conjugation is also difficult to control. For example, a TM may become joined to the remainder of the modified toxin at an attachment site on the protease component and/or on the translocation component. This is problematic when attachment to only one of said components (preferably at a single site) is desired for therapeutic efficacy. Thus, chemical conjugation results in a mixed population of modified toxin molecules, which is undesirable.

As an alternative to chemical conjugation, TM replacement may be effected by recombinant preparation of a single-chain polypeptide fusion protein. The preparation of such molecules is described in WO98/07864. However, the present inventors have identified that the WO98/07864 methodology is not suitable for all types of TM.

An alternative system to that of WO98/07864 is described in WO2006/059093. According to WO2006/059093, the TM is centrally-presented (CP) within the single-chain fusion protein, between the non-cytotoxic protease component and the translocation domain component. This results in a single-chain fusion protein having the following structure:

$NH_2$-[protease component]-[TM]-[translocation component]-COOH

The above-described fusion proteins are activated by treatment with a protease, which cleaves at a site located at the C-terminus of the protease component. This activation process results in a di-chain protein comprising the protease component attached covalently (via a disulphide linkage) to the translocation component of the fusion protein. In the case of WO2006/059093, the resulting di-chain molecule has a TM that is peptide-bonded via its C-terminus to the N-terminus of the translocation domain component. Accordingly, the N-terminal portion of the TM is then free to interact and bind to a desired receptor. This arrangement is important for the class of TMs that requires a free N-terminus or a free N-terminal portion in order to bind to its receptor.

By way of example, following proteolytic activation, WO2006/059093 provides polypeptides having the following di-chain conformation:

$NH_2$-[protease component]    [TM]-[translocation component]-COOH

In said di-chain conformation, the TM and translocation components are presented in the form of a single-chain fusion protein, wherein the C-terminus of the TM is peptide-bonded to the N-terminus of the translocation component.

The present inventors have found that the systems described in WO98/07864 and WO2006/059093 are not optimal for the presentation of all types of TM, and, as such, may result in the production of fusion proteins having undesirable/reduced binding ability for the intended target cell.

There is therefore a need for an alternative or improved system for constructing TSIs.

BRIEF DESCRIPTION OF THE DRAWING

FIG. 1 Illustrates an SDS-PAGE analysis of activated samples (eluted in the 80 mM and 250 mM imidazole fractions) from Example 4 in reducing & non-reducing conditions.

DETAILED DESCRIPTION OF THE INVENTION

The present invention addresses one or more of the above-mentioned problems by providing a single-chain, polypeptide fusion protein, comprising:

(a) a non-cytotoxic protease or a fragment thereof, which protease or protease fragment is capable of cleaving a protein of the exocytic fusion apparatus of a target cell;

(b) a targeting moiety that is capable of binding to a binding site on the target cell, which binding site is capable of undergoing endocytosis to be incorporated into an endosome within the target cell;

(c) a translocation domain that is capable of translocating the protease or protease fragment from within an endosome, across the endosomal membrane and into the cytosol of the target cell;

(d) a first protease cleavage site at which site the fusion protein is cleavable by a first protease, wherein the first protease cleavage site is located between the non-cytotoxic protease and the translocation domain;

(e) a second protease cleavage site at which site the fusion protein is cleavable by a second protease, wherein the second protease cleavage site is located between the translocation domain and the targeting moiety; and (f) a covalent linkage between the targeting moiety and the translocation domain, wherein following proteolytic cleavage at the second protease cleavage site the targeting moiety remains linked to the translocation domain by said covalent linkage.

The system described in WO2006/059093 provides TSIs having a TM with an N-terminus that is free to interact with a binding site on a target cell. However, the present inventors have found that the system described in WO2006/059093 is not suitable for TMs that require both a free N-terminal domain and a free C-terminal domain in order to interact with a binding site on a target cell.

Thus, in contrast to WO2006/059093, the present invention provides a system for providing TSIs wherein the TM component has both a free N-terminal domain and a free C-terminal domain.

In one embodiment, the present invention provides a single-chain fusion protein having the following N-terminus to C-terminus orientation, wherein P1 and P2 represent the first and second protease cleavage sites:

$NH_2$-[protease component]-[P1]-[TM]-[P2]-[translocation component]-COOH

Following cleavage at the first and second cleavage sites, said single-chain fusion protein assumes the following tri-chain structure in which the TM and translocation components are covalently linked together, and wherein A) the protease component is covalently linked to the TM component:

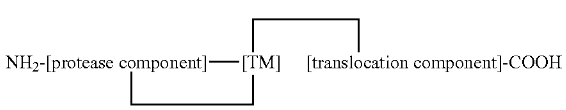

or B) the protease component is covalently linked to the translocation component:

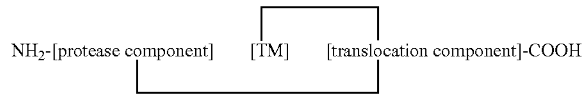

In another embodiment, the present invention provides a single-chain fusion protein having the following N-terminus to C-terminus orientation, wherein P1 and P2 represent the first and second protease cleavage sites:

$NH_2$-[protease component]-[P1]-[translocation component]-[P2]-[TM]-COOH

Following cleavage at the first and second cleavage sites, said single-chain fusion protein assumes the following tri-chain structure in which the TM and translocation components are covalently linked together, and wherein A) the protease component is covalently linked to the translocation component:

or B) the protease component is covalently linked to the TM component:

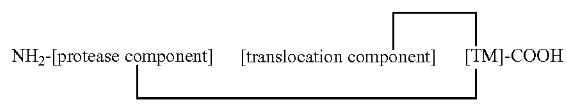

In another embodiment, the present invention provides a single-chain fusion protein having the following N-terminus to C-terminus orientation, wherein P1 and P2 represent the first and second protease cleavage sites:

$NH_2$-[TM]-[P2]-[protease component]-[P1]-[translocation component]-COOH

Following cleavage at the first and second cleavage sites, said single-chain fusion protein assumes the following tri-chain structure in which the TM and translocation components are covalently linked together, and wherein A) the protease component is covalently linked to the translocation component:

or B) the protease component is covalently linked to the TM component:

In use, a polypeptide TSI of the present invention binds to a target cell, the binding being facilitated by the TM. The translocation domain component then effects transport of the non-cytotoxic protease component into the cytosol of the target cell. Once inside, the non-cytotoxic protease component inhibits the exocytic fusion process of the target cell. Thus, by inactivating the exocytic fusion apparatus of the target cell, the polypeptide of the present invention inhibits secretion therefrom. Accordingly, the TSI polypeptides of the present invention can be used to suppress or treat a variety of pathophysiological conditions or symptoms that are linked to cellular secretion.

The Non-Cytotoxic Protease

The biologically active component of the TSI polypeptides of the present invention is a non-cytotoxic protease. Thus, once delivered into the cytosol of a target cell, the non-cytotoxic protease component effects SNARE cleavage within the desired target cell. Since SNARE proteins are an essential component of the secretory process within mammalian target cells, proteolytic inactivation thereof inhibits/suppresses secretion from said target cells.

Non-cytotoxic proteases are a discrete class of molecules that do not kill cells; instead, they act by inhibiting cellular processes other than protein synthesis. Non-cytotoxic proteases are produced by a variety of higher organisms (e.g. plants, and animals)—an example of such a higher organism is the Brazilian scorpion. In addition, non-cytotoxic proteases are produced by a variety of microorganisms, notably bacteria such as *Clostridium* sp. and *Neisseria* sp.

Clostridial neurotoxins represent a major group of non-cytotoxic toxin molecules, and comprise two polypeptide chains joined together by a disulphide bond. The two chains are termed the heavy chain (H-chain), which has a molecular mass of approximately 100 kDa, and the light chain (L-chain), which has a molecular mass of approximately 50 kDa. It is the L-chain, which possesses a protease function and exhibits high substrate specificity for vesicle and/or plasma membrane associated (SNARE) proteins involved in the exocytic process (e.g. synaptobrevin, syntaxin, SNAP and/or VAMP). These substrates are important components of a cell's secretory machinery.

*Neisseria* sp., most notably from the species *N. gonorrhoeae*, produce functionally similar non-cytotoxic toxin molecules. An example of such a non-cytotoxic protease is IgA protease (see WO99/58571). Similar IgA proteases are produced by streptococci, such as *Streptococcus pneumoniae*.

Thus, in one embodiment the non-cytotoxic protease of the present invention may be a clostridial neurotoxin protease or an IgA protease (see, for example, WO 99/032272). Another example of non-cytotoxic proteases is a scorpion venom protease, such as those from the venom of the Brazilian scorpion *Tityus serrulatus*, or the protease antarease (see, for example, WO 2011/022357).

The Targeting Moiety (TM)

The TM component of the present invention is responsible for binding the polypeptide of the present invention to a Binding Site on a target cell. Thus, the TM component is a ligand through which a polypeptide of the present invention binds to a selected target cell.

In the context of the present invention, the target cell may be any mammalian (preferably human) cell. Thus, the TM may bind to a non-neuronal cell and/or to a neuronal cell.

The TM component of the polypeptides of the present invention has both a free N-terminal portion and a free C-terminal portion. Thus, in one embodiment, the TM is capable of interacting with the binding site (e.g. a receptor or acceptor) on a target cell via an interaction between an N-terminal portion of the targeting moiety and a domain of the binding site. In another embodiment, the TM is capable of an interaction between the C-terminal portion of the targeting moiety and a domain of a binding site. In another embodiment, the TM is capable of a dual interaction, wherein an N-terminal portion of the targeting moiety interacts with a domain of the binding site and a C-terminal portion of the targeting moiety interacts with a domain of a binding site. In this latter embodiment, the N- and C-terminal portions of the TM may bind to the same or different domains of a binding site, and/or may bind to domains on different binding sites.

Suitable TMs for use in the polypeptides of the present invention include cytokines, growth factors, neuropeptides, lectins, and antibodies—this term includes monoclonal antibodies, protein binding scaffolds, antibody fragments such as Fab, $F(ab)'_2$, Fv, ScFv, and single-chain antibodies such as camelids etc.

In one embodiment, the TM component comprises or consists of a peptide ligand (e.g. a peptide hormone) that binds to a receptor present on a target cell. In one embodiment, the peptide ligand has an amino acid sequence of 5-200 consecutive amino acid residues. By way of example, said peptide ligand consists or comprises an amino acid sequence of 5-150 or 5-100 or 5-50 or 5-40 or 5-30 or 5-25 or 5-20 or 7-12 or approximately 10 consecutive amino acid residues.

The TM component comprises an N-terminal portion and a C-terminal portion. Each of said portions typically comprise at least 5, at least 10, at least 15, at least 20, or at least 25 consecutive amino acid residues.

In one embodiment, the TM comprises or consists of a peptide ligand (or an analogue thereof) that binds to a receptor selected from $MRGPRX_1$ (e.g. a Bovine Adrenal Medulla (BAM) peptide receptor), an opioid peptide receptor, $OPRM_1$ or $OPRID_1$ (e.g. a beta-endorphin peptide receptor), $BDKRIB_1$ or $BDKRB_2$ (e.g. a bradykinin peptide receptor), OPRM1 or OPRD1 (e.g. a met- or leu-enkephalin peptide receptor), $OPRK_1$ (e.g. a dynorphin peptide receptor), $GALR_1$, $GALR_2$ or $GALR_3$ (e.g. a galanin peptide receptor), $OPRL_1$ (e.g. a nociceptin peptide receptor), and $TACR_1$, $TACR_2$ or $TACR_3$ (e.g. a substance P peptide receptor).

In one embodiment, the TM comprises or consists of a peptide ligand (or an analogue thereof) selected from a Bovine Adrenal Medulla (BAM) peptide, an opioid peptide, a beta-endorphin peptide, a bradykinin peptide, a met- or leu-enkephalin peptide, a dynorphin peptide, a galanin peptide, a nociceptin peptide, and a substance P peptide.

In one embodiment, the TM comprises or consists of a gonadotropin-releasing hormone (GnRH) peptide. GnRH is a 10 amino acid peptide hormone. The N-terminal amino acids of GnRH have a role in receptor activation while the C-terminal amino acids are required for high affinity binding to the GnRH receptor (see Flanagan, Millar & IIling (1997) *Reviews of Reproduction,* 2, 113-120, which is hereby incorporated in its entirety by reference thereto). The function of GnRH in vivo is to act on GnRH receptors located on the anterior pituitary gland and to stimulate the synthesis and release of gonadotropins, such as luteinising hormone (LH) and follicle-stimulating hormone (FSH). Reference to GnRH peptide embraces all functional binding fragments, variants and analogues thereof. By way of example, the term GnRH peptide embraces a GnRH peptide into which a cysteine amino acid (flanked by two achiral amino acid residues such as glycine and/or alanine) has been inserted as a replacement amino acid for position 6 of the GnRH peptide. GnRH is also known as Luteinizing-Hormone Releasing Hormone (LHRH). Further examples include GnRHI peptides, GnRHII peptides and GnRHIII peptides, as well as the full-length 92 amino acid GnRH precursor polypeptide and truncations thereof.

In one embodiment, the TM comprises or consists of a corticotrophin-releasing factor (CRF) peptide. CRF is a 41 amino acid hypothalamic peptide hormone that interacts with CRF, and $CRF_2$ receptors. The main function of CRF in vivo is to stimulate the release of ACTH from the corticotropes within the anterior lobe of the pituitary.

Reference to CRF peptide embraces full-length CRF, urocortin 1 and urocortin 2, as well as all functional binding fragments, variants and analogues thereof.

In one embodiment, the TM comprises or consists of a gastrin releasing peptide (GRP). GRP is a 27 amino acid peptide hormone. GRP regulates numerous functions of the gastrointestinal and central nervous systems, including release of gastrointestinal hormones, smooth muscle cell contraction, and epithelial cell proliferation and is a potent mitogen for neoplastic tissues. Reference to GRP peptide embraces all functional binding fragments, variants and analogues thereof.

In one embodiment, the TM comprises or consists of a neuromedin B. Neuromedin B is a 10 amino acid peptide hormone. The function of neuromedin B acts on BB, receptors in vivo and is a potent mitogen and growth factor for normal and neoplastic lung and for gastrointestinal epithelial tissue. Reference to neuromedin B peptide embraces all functional binding fragments, variants and analogues thereof. Reference to Neuromedin B embraces the human homolog peptide, bombesin, and includes full-length: bombesin—a 14 amino acid peptide originally isolated from the skin of a frog—as wells as truncations and peptide analogues thereof.

In one embodiment, the TM comprises or consists of gastrin or cholecystokinin (CCK). Gastrin is a 17 amino acid peptide hormone, CCK is a 8 amino acid peptide hormone. Both gastrin and cholecystokinin act on CCK1 and CCK2 receptors in vivo primarily within the gastrointestinal system and CNS to modulate pancreatic enzyme secretion and smooth muscle contraction of the gallbladder and stomach, anxiety, analgesia, arousal, and neuroleptic activity. Reference to gastrin and cholecystokinin peptides embraces all functional binding fragments, variants and analogues thereof.

In one embodiment, a TM comprises or consists of a somatostatin (SST) peptide. Examples of suitable SST peptide TMs include full-length SST and cortistatin (CST), as well as truncations and peptide analogues thereof such as BIM 23052, BIM 23056 or BIM23268; octreotide peptides, lanreotide peptides, BIM23027, CYN154806, BIM23027, vapreotide peptides, seglitide peptides, and SOM230. These TMs bind to sst receptors, such as $sst_1$, $sst_2$, $sst_3$, $sst_4$ and $sst_5$ receptors. SST and CST have high structural homology, and bind to all known sst receptors. Reference to SST or CST peptides embraces all functional binding fragments, variants and analogues thereof.

In one embodiment, a TM comprises or consists of a growth hormone releasing hormone (GHRH) peptide. GHRH is also known as growth-hormone-releasing factor (GRF or GHRF) or somatocrinin. Suitable GHRH peptides include full-length GHRH (1-44) peptide, and truncations thereof such as GHRH (1-27, 1-28, 1-29), GHRH (1-37), and GHRH (1-40, 1-43)-OH, as well as peptide analogues such as BIM 28011 or NC-9-96. Reference to GHRH peptide embraces all functional binding fragments, variants and analogues thereof.

In one embodiment, a TM comprises or consists of a proteinase activated receptor (PAR) peptide, for example PAR1. PAR peptides represent a unique subtype of 7-transmembrane receptor G-protein-coupled receptors in that they are proteolytically modified to expose a new extracellular N-terminus, which acts as a tethered activating ligand. PAR1 agonists (such as TFLLR) have been identified that activate their cognate receptor. Reference to PAR peptide embraces all functional binding fragments, variants and analogues thereof.

In one embodiment, a TM comprises or consists of a parathyroid hormone (PTH). PTH is a peptide that is released by the parathyroid gland and binds to the PTH-1 receptor. This receptor has a widespread distribution but is particularly abundant in PTH target tissues, predominantly the kidney and in bone. Reference to PTH peptide embraces all functional binding fragments, variants and analogues thereof.

In one embodiment, a TM comprises or consists of a peptide that binds to a mucus-secreting cell, or to a neuronal cell controlling or directing mucus secretion. For example, the TM binds to (a) cells that secrete mucins, such as epithelial goblet cells and submucosal gland mucus secreting cells, (b) cells that secrete aqueous components of mucus, such as Clara cells and serous cells, and/or (c) cells that control or direct mucus secretion, such as "sensory-efferent" C-fibres, or NANC neural system fibres. Particular mention is made to the following peptide TMs: VIP; $beta_2$ adrenoreceptor agonists; gastrin-releasing peptide; and calcitonin gene related peptide. Reference to these peptide TMs embraces all functional binding fragments, variants and analogues thereof. Thus, TSIs according to this embodiment have therapeutic application in treating mucus hypersecretion, asthma, and/or chronic obstructive pulmonary disease.

In another embodiment, the TM comprises or consists of a peptide that binds to an endocrine cell. Particular mention is made here to GHRH; thyroid stimulating hormone (TSH); insulin, insulin-like growth factor; TSH releasing hormone (protirelin); FSH/LH releasing hormone (gonadorelin); corticotrophin releasing hormone (CRH); and ACTH. Reference to these peptide TMs embraces all functional binding fragments, variants and analogues thereof. Thus, TSIs according to this embodiment have therapeutic application in treating: endocrine neoplasia including MEN; thyrotoxicosis and other diseases dependent on hypersecretions from the thyroid; acromegaly, hyperprolactinaemia, Cushings disease and other diseases dependent on anterior pituitary hypersecretion; hyperandrogenism, chronic anovulation and other diseases associated with polycystic ovarian syndrome.

In another embodiment the TM comprises or consists of a peptide that binds to an inflammatory cell. Particular mention here is made to peptide TMs (i) for mast cells, such as the C4 domain of the Fc IgE; (ii) for eosinophils, such as ligands to the C3a/C4a-R complement receptor, antigens reactive towards CR4 complement receptor; (iii) for macrophages and monocytes, such as macrophage stimulating factor, (iv) for neutrophils, such as an antigen associated with the iC3b complement receptor, or IL8. Reference to these peptide TMs embraces all functional binding fragments, variants and analogues thereof. Thus, TSIs according to this embodiment have therapeutic application for treating allergies (seasonal allergic rhinitis (hay fever), allergic conjunctivitis, vasomotor rhinitis and food allergy), eosinophilia, asthma, rheumatoid arthritis, systemic lupus erythematosus, discoid lupus erythematosus, ulcerative colitis, Crohn's disease, haemorrhoids, pruritus, glomerulonephritis, hepatitis, pancreatitis, gastritis, vasculitis, myocarditis, psoriasis, eczema, chronic radiation-induced fibrosis, lung scarring and other fibrotic disorders.

In another embodiment, the TM comprises or consists of a peptide that binds to an exocrine cell. Particular mention here is made to pituitary adenyl cyclase activating peptide (PACAP-38). Reference to these peptide TMs embraces all functional binding fragments, variants and analogues thereof. Thus, TSIs according to this embodiment have therapeutic application for treating mucus hypersecretion from mucus-secreting cells located in the alimentary tract, in particular located in the colon.

In a further embodiment, the TM comprises or consists of a peptide that binds to an immunological cell. Mention here is made to the ligands such as Epstein Barr virus fragment/surface feature. Reference to these peptide TMs embraces all functional binding fragments, variants and analogues thereof. Thus, TSIs according to this embodiment, have therapeutic application for treating myasthenia gravis, rheumatoid arthritis, systemic lupus erythematosus, discoid lupus erythematosus, organ transplant, tissue transplant, fluid transplant, Graves disease, thyrotoxicosis, autoimmune diabetes, haemolytic anaemia, thrombocytopenic purpura, neutropenia, chronic autoimmune hepatitis, autoimmune gastritis, pernicious anaemia, Hashimoto's thyroiditis, Addison's disease, Sjogren's syndrome, primary biliary cirrhosis, polymyositis, scleroderma, systemic sclerosis, pemphigus vulgaris, bullous pemphigoid, myocarditis, rheumatic carditis, glomerulonephritis (Goodpasture type), uveitis, orchitis, ulcerative colitis, vasculitis, atrophic gastritis, pernicious anaemia, type 1 diabetes mellitus.

In a further embodiment the TM comprises or consists of a peptide that binds to a cardiovascular cell. Mention here is made to thrombin and TRAP (thrombin receptor agonist peptide), and ligands that bind to cardiovascular endothelial cells such as GP1b surface antigen-recognising antibodies. Reference to these peptide TMs embraces all functional binding fragments, variants and analogues thereof. Thus, TSIs according to this embodiment have therapeutic application for treating cardiovascular conditions and/or hypertension In a further embodiment, the TM comprises or consists of a peptide that binds to a bone cell. Mention here is made to ligands that bind to osteoblasts for the treatment of a disease selected from osteopetrosis and osteoporosis include calcitonin, and to ligands that bind to osteoclasts including osteoclast differentiation factors (e.g. TRANCE, or RANKL or OPGL). Reference to these peptide TMs embraces all functional binding fragments, variants and analogues thereof. Thus, TSIs according to this embodiment have therapeutic application for treating bone conditions.

Linear and cyclic integrin binding sequences represent a further group of peptide TMs of the present invention. Many integrins recognise the triple Arg-Gly-Asp (RGD) peptide sequence (Ruoslahti, 1996). The RGD motif is found in over 100 proteins including fibronectin, tenascin, fibrinogen and vitronectin. The RGD-integrin interaction is exploited as a conserved mechanism of cell entry by many pathogens including coxsackievirus (Roivaninen et al., 1991) and adenovirus (Mathias et al., 1994). The linear and cyclic peptide sequences, PLAEIDGIEL (SEQ ID NO: 17) and CPLAEIDGIELC (SEQ ID NO: 18) respectively, have been shown to bind and internalise DNA in cells expressing $\alpha_9\beta_1$ integrin (Schneider et al., 1999). Reference to these peptide TMs embraces all functional binding fragments, variants and analogues thereof.

Other TMs of the present invention include those discovered by phage display techniques, in particular those which target and are internalised by human airway epithelial cells. These include, linear and cyclic THALWHT (SEQ ID NO: 19) (Jost et al., 2001); LEBP-1 (QPFMQCLCLIYDASC) (SEQ ID NO: 20), LEBP-2 (RNVPPIFNDVYWIAF) (SEQ ID NO: 21) and LEBP-3 (VFRVRPWYQSTSQS) (SEQ ID NO: 22) (Wu et al., 2003); CDSAFVTVDWGRSMSLC (SEQ ID NO: 23) (Florea et al., 2003); SERSMNF (SEQ ID NO: 24), YGLPHKF (SEQ ID NO: 25), PSGAARA (SEQ ID NO: 26), LPHKSMP (SEQ ID NO: 27), LQHKSMP (SEQ ID NO: 28) (Writer et al., 2004); FSLSKPP (SEQ ID NO: 29), HSMQLST (SEQ ID NO: 30) and STQAMFQ (SEQ ID NO: 31) peptides (Rahim et al., 2003). Reference to these peptide TMs embraces all functional binding fragments, variants and analogues thereof.

In one embodiment, the TM comprises or consists of first and second portions (e.g. domains). In one embodiment, the first and second portions of the targeting moiety may be derived from the same ligand (e.g. any of the above-identified TM ligands). The first and second portions may bind to the same of different sites on the same receptor. Alternatively, the first and second portions may bind sites on different receptors.

The first and second portions of the targeting moiety may be derived from different ligands (e.g. any of the above-identified TM ligands), which may bind to the same or to different receptors. Accordingly, the TM may be a hybrid of two TMs. The first and second portions may bind to the same of different sites on the same receptor. Alternatively, the first and second portions may bind sites on different receptors.

The TM may further include third and/or subsequent portions from yet further TMs (e.g. any of the above-identified TM ligands).

In one embodiment, the first portion (e.g. domain) comprises or consists of a ligand that binds via a free N-terminal portion (e.g. a free N-terminus) to its target receptor. An example of such a ligand is a ligand that binds to an opioid receptor (e.g. a ligand that binds to an $ORL_1$ receptor, such as an opioid peptide). Further examples of opioid peptides include nociceptin, dynorphin, beta-endorphin, and enkephalin. Other non-opioid peptide TM ligands include BAM, galanin, substance P, GnRH, CRF, GRP, Neuromedin B, bombesin, gastrin, CCK, SST, CST, and GHRH peptides (as well as truncations, variants and analogues thereof).

In another (or the same) embodiment, the second portion (e.g. domain) comprises or consists of a ligand that binds via a free C-terminal portion (e.g. a free C-terminus) to its target receptor. An example of such a ligand is a ligand that binds to a bradykinin receptor (e.g. a bradykinin peptide) or to a substance P receptor (e.g. a substance P peptide). Other peptide TM ligands include BAM, galanin, substance P, GnRH, CRF, GRP, Neuromedin B, bombesin, gastrin, CCK, SST, CST, and GHRH peptides (as well as truncations, variants and analogues thereof).

By way of example, the hybrid TM includes a first portion that comprises or consists of a nociceptin peptide and a second portion that comprises or consists of a bradykinin peptide (or a substance P peptide). In further examples, the first portion comprises or consists of a nociceptin peptide and the second portion comprises or consists of a peptide selected from a BAM peptide, an opioid peptide, a beta-endorphin peptide, a bradykinin peptide, an enkephalin peptide, a dynorphin peptide, a galanin peptide, and a substance P peptide.

In another example, the hybrid TM includes a first portion that comprises or consists of a dynorphin peptide and a second portion that comprises or consists of a bradykinin peptide (or a substance P peptide). In further examples, the first portion comprises or consists of a dynorphin peptide and the second portion comprises or consists of a peptide selected from a BAM peptide, an opioid peptide, a beta-endorphin peptide, a bradykinin peptide, an enkephalin peptide, a nociceptin peptide, a galanin peptide, and a substance P peptide.

In another example, the hybrid TM includes a first portion that comprises or consists of a galanin peptide and a second portion that comprises or consists of a bradykinin peptide (or a substance P peptide). In further examples, the first portion comprises or consists of a galanin peptide and the second portion comprises or consists of a peptide selected from a BAM peptide, an opioid peptide, a beta-endorphin peptide, a bradykinin peptide, an enkephalin peptide, a nociceptin peptide, a dynorphin peptide, and a substance P peptide.

In another example, the hybrid TM includes a first portion that comprises or consists of a BAM peptide and a second portion that comprises or consists of a bradykinin peptide (or a substance P peptide). In further examples, the first portion comprises or consists of a BAM peptide and the second portion comprises or consists of a peptide selected from an opioid peptide, a beta-endorphin peptide, a bradykinin peptide, an enkephalin peptide, a nociceptin peptide, a dynorphin peptide, a galanin peptide, and a substance P peptide.

In another example, the hybrid TM includes a first portion that comprises or consists of a beta-endorphin peptide and a second portion that comprises or consists of a bradykinin peptide (or a substance P peptide). In further examples, the first portion comprises or consists of a beta-endorphin peptide and the second portion comprises or consists of a peptide selected from an opioid peptide, a BAM peptide, a bradykinin peptide, an enkephalin peptide, a nociceptin peptide, a dynorphin peptide, a galanin peptide, and a substance P peptide.

In another example, the hybrid TM includes a first portion that comprises or consists of an enkephalin (e.g. leu- or met-enkephalin) peptide and a second portion that comprises or consists of a bradykinin peptide (or a substance P peptide). In further examples, the first portion comprises or consists of an enkephalin peptide and the second portion comprises or consists of a peptide selected from an opioid peptide, a beta-endorphin peptide, a bradykinin peptide, a BAM peptide, a nociceptin peptide, a dynorphin peptide, a galanin peptide, and a substance P peptide.

In one embodiment, the TM comprises or consists of first and second portions (e.g. domains) that are identical (or similar) and, in combination, provide efficacious interaction with the receptor on the target cell. Further (e.g. third, and optionally additional etc) identical/similar portions may also be included. Thus, in this embodiment, the polypeptides of the present invention comprise a repeating structure (e.g. TM-TM; TM-TM-TM etc) of the same (or a similar) TM.

Examples of such repeating TM structures (e.g. TM-TM; TM-TM-TM; etc) are provided by a TM selected from an opioid peptide, a beta-endorphin peptide, a bradykinin peptide, a BAM peptide, a nociceptin peptide, a dynorphin peptide, a galanin peptide, an enkephalin peptide, a substance P peptide, a GnRH peptide, a CRF peptide, a GRP peptide, a Neuromedin B peptide, a bombesin peptide, a gastrin peptide, a CCK peptide, a SST peptide, a CST peptide, and a GHRH peptide (as well as truncations, variants and analogues thereof).

In one embodiment, the first and second (and/or subsequent) portions of the TM are separated by a spacer sequence, for example a peptide sequence. In one embodiment, the first and second (and/or subsequent) portions may be separated by a sequence of at most 40 or at most 35 or at most 30 or at most 25 or at most 20 or at most 15 or at most 10 at most 5 amino acid residues. In one embodiment, the first and second (and/or subsequent) portions may be separated by a sequence of 4, 3, 2, 1 or zero amino acid residues.

The fusion proteins of the present invention generally demonstrate a reduced binding affinity (in the region of up to 100-fold) for target cells when compared with the corresponding 'free' TM (i.e. the isolated TM per se). However, despite this observation, the fusion proteins of the present invention surprisingly demonstrate good efficacy. This can be attributed to two principal features. First, the non-cytotoxic protease component is catalytic—thus, the therapeutic effect of a few such molecules is rapidly amplified within a target cell. Secondly, the receptors present on the target cells need only act as a gateway for entry of the therapeutic, and need not necessarily be stimulated to a level required in order to achieve a ligand-receptor mediated pharmacological response. Accordingly, the fusion proteins of the present invention may be administered at a dosage that is lower than would be employed for other types of therapeutic molecules, which are typically administered at high microgram to milligram (even up to hundreds of milligram) quantities. In contrast, the fusion proteins of the present invention may be administered at much lower dosages, typically at least 10-fold lower, and more typically at 100-fold lower.

The Translocation Domain

The translocation component of the present invention enables translocation of the non-cytotoxic protease (or fragment thereof) into the target cell so that functional expression of protease activity occurs within the cytosol of the target cell. The translocation component is preferably capable of forming ion-permeable pores in lipid membranes (e.g. endosomal membranes) under conditions of low pH. The translocation component may be obtained from a microbial protein source, for example a bacterial or viral protein source. Hence, in one embodiment, the translocation component comprises or consists or a translocation domain of an enzyme, such as a bacterial toxin. In another embodiment, the translocation domain comprises or consists of the translocation domain of a viral protein. In one embodiment, the translocation component of the present invention may comprise or consist of a clostridial neurotoxin H-chain or a fragment thereof such as the $H_N$ domain (or a translocating fragment thereof) of a clostridial neurotoxin.

The First and Second Protease Cleavage Sites

The polypeptides of the present invention comprise a first protease cleavage site. The first protease cleavage site allows cleavage (e.g. controlled cleavage) of the fusion protein at a position between the non-cytotoxic protease component and the remainder of the fusion protein. This cleavage event serves to 'activate' the single-chain (non-cytotoxic protease-translocation domain) structure, and results in the formation of an 'activated' di-chain structure in which the non-cytotoxic protease component is covalently linked (e.g. disulphide-bonded) to the remainder of the fusion protein.

The polypeptides of the present invention also comprise a second protease cleavage site. The second protease cleavage site allows cleavage (e.g. controlled cleavage) of the fusion protein at a position between the targeting moiety component and the translocation domain component. This cleavage event serves to separate the single-chain (TM-translocation domain) structure, and results in the formation of a separate di-chain structure in which the TM component is covalently linked (e.g. disulphide-bonded) to the translocation component of the fusion protein. In doing so, the structural environment of the TM component is changed such that it becomes presented in a conformation in which both the N-terminal and C-terminal portions (e.g. domains) are no longer peptide-bonded to the remainder of the fusion protein and are thus each able freely to interact with (e.g. bind to) different binding domains on one (or more) receptor.

Thus, proteolytic cleavage at either the first or second protease cleavage sites converts the single-chain polypeptide fusion protein into a di-chain polypeptide. In the case of a cleavage reaction at the first protease cleavage site, the non-cytotoxic protease component remains linked by a covalent linkage (e.g. a disulphide bond) to the translocation domain component and/or to the TM component. Said covalent linkage may be indirect, for example, via one (or more) spacer or linker molecule, which is itself linked to the non-cytotoxic protease component, the TM component and/or the translocation component. Similarly, in the case of a cleavage reaction at the second protease cleavage site, the translocation domain component remains linked to the TM component by a covalent linkage (e.g. a disulphide bond). Said covalent linkage may be indirect, for example, via one (or more) spacer or linker molecule, which is itself linked to the translocation component and/or the TM.

Where cleavage reactions occur at both the first and second protease cleavage sites, the single-chain polypeptide fusion protein is converted into a tri-chain polypeptide.

The first and second protease cleavage sites may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.).

Whilst any protease cleavage site may be employed for use as the first protease cleavage site and/or for use as the second protease cleavage site in the polypeptides of the present invention, the following are preferred:

| | |
|---|---|
| Enterokinase | (DDDDK↓ (SEQ ID NO: 32)) |
| Factor Xa | (IEGR↓ (SEQ ID NO: 33)/ IDGR↓ (SEQ ID NO: 34)) |
| TEV (Tobacco Etch virus) | (ENLYFQ↓G (SEQ ID NO: 35)) |
| Thrombin | (LVPR↓GS (SEQ ID NO: 36)) |
| PreScission | (LEVLFQ↓GP (SEQ ID NO: 37)) |

Further non-limiting examples include plant papain cleavage site, and insect papain cleavage site, a crustacean papain cleavage site, a human rhinovirus 3C protease cleavage site, a human enterovirus 3C protease cleavage site, a tobacco etch virus (TEV) protease cleavage site, a Tobacco Vein Mottling Virus (TVMV) cleavage site, a subtilisin cleavage site, a hydroxylamine cleavage site, or a Caspase 3 cleavage site.

Also embraced by the term protease cleavage site is an intein, which is a self-cleaving sequence. The self-splicing reaction is controllable, for example by varying the concentration of reducing agent present. Also embraced by the term protease cleavage site is the cleavage sequence upon which a non-cytotoxic protease (e.g. a clostridial neurotoxin) acts. An example of such a cleavage site is a SNARE protein cleavage site sequence—examples of the native cleavage site recognition sequences for a range of non-cytotoxic proteases are provided towards the end of the present description section.

The first and second cleavage site may be the same or different. The first and second cleavage sites may be cleaved by (only) the same or (only) by different proteases.

As a separate aspect of the present invention, the above-mentioned cleavage sites/cleaving protease may be separately employed as a "destructive" cleavage site/protease (discussed below) should one be incorporated into a polypeptide of the present invention.

In one embodiment, in the single-chain polypeptide, the non-cytotoxic protease component and the translocation domain component are linked together by a disulphide bond. Thus, following cleavage of the first protease cleavage site, the polypeptide assumes a di-chain conformation, wherein the protease and translocation components remain linked together by the disulphide bond. This cleavage reaction is generally referred to as the "activation" step as it results in the non-cytotoxic protease component having increased (e.g. optimal) protease activity.

In one embodiment, the non-cytotoxic protease component forms a covalent bond with the translocation domain component of the fusion protein. For example, in one embodiment the amino acid residue of the protease component that forms the covalent bond is located within the last 20, preferably within the last 10 C-terminal amino acid residues of the protease component. Similarly, in one embodiment the amino acid residue within the translocation component that forms the second part of the covalent bond may be located within the first 20, preferably within the first 10 N-terminal amino acid residues of the translocation component.

The above covalent bond arrangements have the advantage that the protease and translocation components are arranged in a manner similar to that for a native non-cytotoxic protease (e.g. a native clostridial neurotoxin). By way of comparison, referring to the primary amino acid sequence for native clostridial neurotoxin, the respective cysteine amino acid residues are distanced apart by between 8 and 27 amino acid residues—taken from Popoff, M R & Marvaud, J-C, 1999, Structural & genomic features of clostridial neurotoxins, Chapter 9, in The Comprehensive Sourcebook of Bacterial Protein Toxins. Ed. Alouf & Freer:

| Serotype[1] | Sequence | 'Native' length between C-C |
|---|---|---|
| BoNT/A1 | CVRGIITSKTKS----LDKGYNKALNDLC (SEQ ID NO: 38) | 23 |
| BoNT/A2 | CVRGIIPFKTKS----LDEGYNKALNDLC (SEQ ID NO: 39) | 23 |

-continued

| Serotype[1] | Sequence | 'Native' length between C-C |
|---|---|---|
| BoNT/B | CKSVKAPG------------------IC (SEQ ID NO: 40) | 8 |
| BoNT/C | CHKAIDGRS---------LYNKTLDC (SEQ ID NO: 41) | 15 |
| BoNT/D | CLRLTK--------------NSRDDSTC (SEQ ID NO: 42) | 12 |
| BoNT/E | CKN-IVSVK---------GIRK---SIC (SEQ ID NO: 43) | 13 |
| BoNT/F | CKS-VIPRK---------GTKAPP-RLC (SEQ ID NO: 44) | 15 |
| BoNT/G | CKPVMYKNT---------GKSE----QC (SEQ ID NO: 45) | 13 |
| TeNT | CKKIIPPTNIRENLYNRTASLTDLGGELC (SEQ ID NO: 46) | 27 |

[1]Information from proteolytic strains only

In one embodiment, the non-cytotoxic protease component and the first protease cleavage site component of a single-chain fusion protein of the present invention are separated by at most 30, 25, 20, 15 or 10 amino acid residues. In one embodiment, said two components are separated within the single-chain fusion protein by at most 5, 4, 3, 2 or 1 amino acid residues. In another embodiment, said two components are separated within the single-chain fusion protein by zero amino acid residues.

Thus, in one embodiment, the non-cytotoxic protease and the first protease cleavage site may be separated using a first spacer sequence, said spacer sequence being located N-terminal to the first protease cleavage site and C-terminal of the non-cytotoxic protease component. In one embodiment, the first spacer sequence may comprise part or all of the first protease cleavage site, or may be part of the non-cytotoxic protease component.

In one embodiment, the translocation domain (or TM) component and the first protease cleavage site component of the single-chain fusion protein are separated by at most 30, 25, 20, 15 or 10 amino acid residues. In one embodiment, said two components are separated within the single-chain fusion protein by at most 5, 4, 3, 2 or 1 amino acid residues. In another embodiment, said two components are separated within the single-chain fusion protein by zero amino acid residues.

Thus, in one embodiment, the translocation domain (or TM) and the first protease cleavage site may be separated by a second spacer sequence, said second spacer sequence being located C-terminal to the first protease cleavage site and N-terminal of the translocation domain (or TM) component. The second spacer sequence may be identical to or different from the first spacer sequence separating the non-cytotoxic protease and the first protease cleavage site. In one embodiment, the second spacer sequence may comprise part or all of the second protease cleavage site, or may be part of the translocation domain component.

In one embodiment, the translocation domain component and the second protease cleavage site component of the single-chain fusion protein are separated at most 30, 25, 20, 15 or 10 amino acid residues. In one embodiment, said two components are separated within the single-chain fusion protein by at most 5, 4, 3, 2 or 1 amino acid residues. In another embodiment, said two components are separated within the single-chain fusion protein by zero amino acid residues.

Thus, in one embodiment, the translocation domain and the second protease cleavage site may be separated by a third spacer sequence, said third spacer sequence being located N-terminal or C-terminal to the translocation domain. The third spacer sequence may be identical to (or different from) one or both of the first and second spacer sequences. In one embodiment, the third spacer sequence may comprise part or all of the second protease cleavage site, or may be part of the translocation domain component.

In one embodiment, the targeting moiety and the second protease cleavage site are separated by at most 30, 25, 20, 15 or 10 amino acid residues. In one embodiment, said two components are separated within the single-chain fusion protein by at most 5, 4, 3, 2 or 1 amino acid residues. In another embodiment, said two components are separated within the single-chain fusion protein by zero amino acid residues.

Thus, following cleavage at the second protease cleavage site, a polypeptide is provided with a targeting moiety that has an N-terminal domain and a C-terminal domain that are substantially free from the remainder of the conjugate. This arrangement facilitates interaction of the N-terminal and C-terminal components of the targeting moiety with a binding site on a target cell.

In one embodiment, the targeting moiety and the second protease cleavage site may be separated by a fourth spacer sequence, said fourth spacer sequence being located N-terminal or C-terminal of the targeting moiety. The fourth spacer sequence may be identical to (or different from) one, two or all of the first, second and third spacer sequences. In one embodiment, the fourth spacer sequence may comprise part or all of the second protease cleavage site, or may be part of the translocation domain component.

In one embodiment, the first protease (by which the first protease cleavage site is cleavable) is the same as the second protease (by which the second protease cleavage site is cleavable).

Thus, in one embodiment, treatment of the single-chain polypeptide fusion protein with a single protease may result in the cleavage of both the first and second protease cleavage sites.

A variety of different spacer molecules may be employed in any of the fusion proteins of the present invention. Examples of such spacer molecules include GS5, GS10, GS15, GS20, GS25, and Hx27.

The Covalent Linkage

The polypeptide fusion proteins of the present invention comprise two covalent linkages: the first such linkage is between the non-cytotoxic protease component and the remainder of the fusion protein; and the second such linkage is between the targeting moiety and the translocation domain. Following proteolytic cleavage at the (respective) first and second protease cleavage sites, said two covalent linkages remain intact. In one embodiment, the covalent linkages are not peptide bonds (i.e. the covalent linkages are non-peptide bonds). For example, in one embodiment, one or both of said covalent linkages are disulphide bonds.

Following proteolytic cleavage at the second protease cleavage site, the covalent linkage remains intact. Cleavage at the second protease cleavage site has the effect of exposing the N-terminus (or C-terminus) of the targeting moiety. Thus, cleavage at the second protease cleavage site produces a targeting moiety having a free N-terminus and a free C-terminus.

Thus, following cleavage at the second protease cleavage site the targeting moiety component is no longer part of the same polypeptide chain as the translocation domain component, as the peptide linkage between the targeting moiety and the translocation domain has been cleaved. However, the targeting moiety remains attached to the translocation domain due to the presence of the covalent linkage.

The covalent linkage may comprise any covalent linkage capable of forming or being formed between two amino acid residues in a polypeptide chain.

In one embodiment, the covalent linkage is a disulphide linkage. A disulphide linkage may be formed between any two thiol (i.e. —SH) groups present in the polypeptide. By way of example, disulphide linkages may form between two cysteine residues (or functionally equivalent variants thereof) located in a polypeptide chain.

Thus, in one embodiment, a cysteine residue located in the translocation domain component forms a covalent linkage with another cysteine residue located in the targeting moiety component. Such a disulphide linkage remains intact following cleavage at the second protease cleavage site.

The amino acid residues located in the translocation domain component and in the targeting moiety component that are joined by the covalent linkage may be present naturally in said components. Thus, in one embodiment the covalent linkage forms between an amino acid residue present naturally in the translocation domain component and an amino acid residue present naturally in the targeting moiety component. Alternatively, one or both of said amino acid residues may be introduced into the translocation domain component and/or the targeting moiety component. The amino acid residues may be introduced as substitutions.

In one embodiment, the covalent linkage is a disulphide linkage formed between a cysteine residue naturally present in the translocation domain component and a cysteine residue naturally present in the targeting moiety component. In an alternative embodiment, a cysteine residue is specifically introduced into either the translocation domain or the targeting moiety, or both, in order to facilitate or allow the formation of a disulphide linkage between these two components.

In one embodiment, one or more cysteine residue is introduced into the TM and/or translocation domain. When doing so, the introduced cysteine residue(s) may be flanked by two, small, achiral amino acid residues (such as glycine and/or alanine). Use of such amino acid residues avoids immediate tertiary structure and facilitates disulphide bond formation. The small, achiral amino acid residues may be present naturally, or may be introduced into the TM and/or translocation domain.

In one embodiment, in addition to the covalent linkage, there is located between the translocation domain and the targeting moiety a short polypeptide (e.g. 1-20, or 1-10, or 5-10 amino acid residues) that provides a secondary polypeptide structure. Said secondary polypeptide structure helps position the translocation domain and the targeting moiety, thereby assisting (1) formation of the covalent linkage between the TM and the translocation domain, and/or (2) positioning of the TM such that it's C-terminal and N-terminal ends face away from the translocation component.

Thus, in one embodiment the secondary polypeptide structure acts to bring part of the targeting moiety into close proximity to the translocation domain, thereby making formation of the covalent linkage energetically more favourable.

In one embodiment, a polypeptide capable of forming a secondary polypeptide structure as described above is a polypeptide sequence containing at least one 'bulky' amino acid residue such as a proline residue.

Thus, in one embodiment, there is located between the translocation domain and the targeting moiety a polypeptide comprising at least one bulky amino acid residue. Said bulky residue helps to form a bend in the polypeptide chain, such that part of the targeting moiety is brought into closer proximity with the translocation domain than would otherwise be the case.

The corresponding covalent linkage between the non-cytotoxic protease component and the remainder of the fusion protein (e.g. the translocation component and/or the TM component) may be formed in the same way as described above for the covalent linkage between the translocation domain component and the TM component. As described above, one or more secondary structure and/or one or more bulky amino acid residue may be introduced.

In one embodiment, the covalent linkage between the non-cytotoxic protease component and the remainder of the fusion protein is between the non-cytotoxic protease component and the translocation domain component. In one embodiment, the covalent linkage between the non-cytotoxic protease component and the translocation domain component employs naturally-occurring cysteine residues located on the respective components, such as for example one or more of the cysteine residues illustrated earlier in the description section. Alternatively, one or more appropriate cysteine residue(s) may be introduced into the respective components.

The fusion protein may comprise one or more purification tags, which are located N-terminal to the protease component and/or C-terminal to the translocation component.

Whilst any purification tag may be employed, the following are preferred:

His-tag (e.g. 6× histidine (SEQ ID NO: 47)), preferably as a C-terminal and/or N-terminal tag MBP-tag (maltose binding protein), preferably as an N-terminal tag GST-tag (glutathione-S-transferase), preferably as an N-terminal tag His-MBP-tag, preferably as an N-terminal tag GST-MBP-tag, preferably as an N-terminal tag Thioredoxin-tag, preferably as an N-terminal tag CBD-tag (Chitin Binding Domain), preferably as an N-terminal tag.

Therapeutic Applications

The TM component directs the targeted secretion inhibitor (TSI) therapeutic molecule of the present invention to the desired target cell.

By way of example, use of TMs described throughout this specification (such as an opioid peptide, a beta-endorphin peptide, a bradykinin peptide, a BAM peptide, a nociceptin peptide, a dynorphin peptide, a galanin peptide, an enkephalin peptide, a substance P peptide) direct the targeted secretion inhibitor (TSI) therapeutic molecule of the present invention to pain-sensing cells (e.g. primary sensory afferents). The resulting fusion proteins thus provide therapeutic molecules for suppressing pain—Applicant refers to WO2006/059093, WO2007/138339 and WO96/33273, each of which is incorporated in its entirety by reference thereto.

TMs described throughout this specification may be used to direct the targeted secretion inhibitor (TSI) molecules of the present invention to cells that promote neurogenic inflammation. Accordingly, the targeted secretion inhibitor (TSI) molecules of the present invention provide therapeutic molecules for suppressing neurogenic inflammation—Applicant refers to WO2010/138395, WO2010/138392, WO2010/138387, WO2010138382 and WO2010/138379, each of which is incorporated in its entirety by reference thereto. Preferred TMs for use in such TSI molecules and therapies include opioid TMs such as nociceptin and dynorphin.

TMs described throughout this specification may be used to direct the targeted secretion inhibitor (TSI) molecules of the present invention to cells that promote urogenital-neurological disorders such as over-active bladder. Accordingly, the targeted secretion inhibitor (TSI) molecules of the present invention provide therapeutic molecules for suppressing urogenital-neurological disorders such as over-active bladder—Applicant refers to WO2010/138393, WO2010/138389, WO2010/138384, and WO2010/138366, each of which is incorporated in its entirety by reference thereto. Preferred TMs for use in such TSI molecules and therapies include opioid TMs such as nociceptin and dynorphin.

TMs such as gonadotropin-releasing hormone (GnRH) peptide, CRF peptide, GRP peptide, Neuromedin B peptide, bombesin peptide, gastrin peptide, CCK peptide, SST peptide, CST peptide, and GHRH peptide may be used to direct the TSI molecules of the present invention to cells that promote cancer or indeed to cancerous cells per se. Accordingly, the targeted secretion inhibitor (TSI) molecules of the present invention provide therapeutic molecules for suppressing neuroendocrine conditions such as acromegaly and Cushing's disease and for suppressing cancer (e.g. lung cancer, renal cancer, brain cancer, breast cancer, pancreatic cancer, colorectal cancer, adrenal cancer, oesophageal cancer, lymphoma, leukaemia, acute leukaemia, bladder cancer, bone cancer, bowel cancer, cervical cancer, chronic lymphocytic leukaemia, Hodgkin's lymphoma, liver cancer, skin cancer, oropharyngeal cancer, myeloma, prostate cancer, gastric cancer, testicular cancer, uterine cancer or Kaposi sarcoma—Applicant refers to WO2009/150489, WO2009/150470 and WO2010/055358, each of which is incorporated in its entirety by reference thereto. Preferred TMs for use in such TSI molecules and therapies include GHRH peptides, SST peptides and CST peptides.

Destructive Cleavage Sites

The polypeptides of the present invention may be further modified to reduce or prevent unwanted side-effects associated with dispersal into non-targeted areas. According to this embodiment, the polypeptide comprises a destructive cleavage site. The destructive cleavage site is distinct from the 'activation' site (i.e. di-chain formation) and from the second protease cleavage site (i.e. formation of a TM with free C-terminal and N-terminal domains). Said destructive cleavage site is cleavable by a third protease and not by the first or second proteases. Moreover, when so cleaved at the destructive cleavage site by the third protease, the polypeptide of the invention has reduced potency (e.g. reduced binding ability to the intended target cell, reduced translocation activity and/or reduced non-cytotoxic protease activity). By way of example, Applicant refers to WO 2010/094905 & WO 02/044199, each of which is hereby incorporated in its entirety by reference thereto.

Thus, according to this embodiment, the present invention provides a polypeptide that can be controllably inactivated and/or destroyed at an off-site location.

In one embodiment, the destructive cleavage site is recognised and cleaved by a third protease (i.e. a destructive protease) selected from a circulating protease (e.g. an extracellular protease, such as a serum protease or a protease of the blood clotting cascade), a tissue-associated protease (e.g. a matrix metalloprotease (MMP), such as an MMP of muscle), and an intracellular protease (preferably a protease that is absent from the target cell). Thus, in use, should a polypeptide of the present invention become dispersed away from its intended target cell and/or be taken up by a non-target cell, the polypeptide will become inactivated by cleavage of the destructive cleavage site (by the third protease).

Matrix metalloproteases (MMPs) are a preferred group of destructive proteases in the context of the present invention. Within this group, ADAM17 (EC 3.4.24.86, also known as TACE), is preferred and cleaves a variety of membrane-anchored, cell-surface proteins to "shed" the extracellular domains. Additional, preferred MMPs include adamalysins, serralysins, and astacins. Another group of preferred destructive proteases is a mammalian blood protease, such as Thrombin, Coagulation Factor VIIa, Coagulation Factor IXa, Coagulation Factor Xa, Coagulation Factor XIa, Coagulation Factor XIIa, Kallikrein, Protein C, and MBP-associated serine protease.

In accordance with a second aspect of the present invention, there is provided a nucleic acid sequence encoding the above-described polypeptide fusion protein.

In a preferred aspect of the present invention, the DNA sequence is prepared as part of a DNA vector, wherein the vector comprises a promoter and terminator. The DNA sequence encoding the above-described polypeptide fusion protein is located downstream of the promoter; the terminator is located downstream of the nucleic acid sequence.

In a preferred embodiment, the vector has a promoter selected from:

| Promoter | Induction agent | Typical induction condition |
|---|---|---|
| tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

The DNA construct of the present invention is preferably designed in silico, and then synthesised by conventional DNA synthesis techniques.

The above-mentioned DNA sequence information is optionally modified for codon-biasing according to the ultimate host cell (e.g. E. coli) expression system that is to be employed.

The DNA backbone is preferably screened for any inherent nucleic acid sequence, which when transcribed and translated would produce an amino acid sequence corresponding to the protease cleave site encoded by the second peptide-coding sequence. This screening may be performed manually or with the assistance of computer software (e.g. the MapDraw program by DNASTAR, Inc.).

According to another embodiment of the present invention, there is provided a method for preparing a single-chain polypeptide fusion protein as described above, comprising expressing a nucleic acid sequence encoding the above-described fusion protein, or a DNA vector as described above, in a host cell.

According to a further embodiment of the present invention, there is provided a method of preparing a non-cytotoxic agent, comprising:
  a. providing a solution containing a single-chain polypeptide fusion protein of the invention;
  b. adding to said solution a first protease capable of cleaving the first protease cleavage site and a second protease capable of cleaving the second protease cleavage site;
  c. cleaving the first protease cleavage site and the second protease cleavage site;
  thereby forming a tri-chain fusion protein.

In one embodiment, the first protease and the second protease are added sequentially. In an alternative embodiment, the second protease is added before the first protease. In yet another embodiment, the first protease and the second protease are added simultaneously.

This aspect provides a tri-chain polypeptide. In more detail, the resulting tri-chain polypeptide typically has a structure wherein:
  a. the first chain comprises the non-cytotoxic protease, or a fragment thereof, which protease or protease fragment is capable of cleaving a protein of the exocytic fusion apparatus of a target cell;
  b. the second chain comprises the translocation domain that is capable of translocating the protease or protease fragment from within an endosome, across the endosomal membrane and into the cytosol of the target cell;
  c. the third chain comprises the targeting moiety that is capable of binding to a binding site on the target cell, which binding site is capable of undergoing endocytosis to be incorporated into an endosome within the target cell;
  d. the first and second chains are disulphide linked together; and the second and third domains are linked together by a non-peptide covalent linkage.

Polypeptide Delivery

According to a further aspect of the present invention, there is provided a single-chain polypeptide fusion protein as described above, or a non-cytotoxic polypeptide as described above, for use in treating, preventing or ameliorating a medical condition.

In use, the present invention employs a pharmaceutical composition, comprising a polypeptide, together with at least one component selected from a pharmaceutically acceptable carrier, excipient, adjuvant, propellant and/or salt.

The polypeptides of the present invention may be formulated for oral, parenteral, continuous infusion, implant, inhalation or topical application. Compositions suitable for injection may be in the form of solutions, suspensions or emulsions, or dry powders which are dissolved or suspended in a suitable vehicle prior to use.

Local delivery means may include an aerosol, or other spray (e.g. a nebuliser). In this regard, an aerosol formulation of a polypeptide enables delivery to the lungs and/or other nasal and/or bronchial or airway passages. A preferred route of administration is selected from: systemic (e.g. iv), laparoscopic and/or localised injection (for example, transsphenoidal injection directly into a target cell such as a tumour).

In the case of formulations for injection, it is optional to include a pharmaceutically active substance to assist retention at or reduce removal of the polypeptide from the site of administration. One example of such a pharmaceutically active substance is a vasoconstrictor such as adrenaline. Such a formulation confers the advantage of increasing the residence time of polypeptide following administration and thus increasing and/or enhancing its effect.

The dosage ranges for administration of the polypeptides of the present invention are those to produce the desired therapeutic effect. It will be appreciated that the dosage range required depends on the precise nature of the polypeptide or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages (per kg weight of patient) are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or preferably less frequently, such as weekly or six monthly. A particularly preferred dosing regimen is based on 2.5 ng of polypeptide as the 1× dose. In this regard, preferred dosages are in the range 1×-100× (i.e. 2.5-250 ng).

Fluid dosage forms are typically prepared utilising the polypeptide and a pyrogen-free sterile vehicle. The polypeptide, depending on the vehicle and concentration used, can be either dissolved or suspended in the vehicle. In preparing solutions the polypeptide can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition/s to facilitate uniform distribution of the components.

Definitions Section

Targeting Moiety (TM) means any chemical structure that functionally interacts with a Binding Site to cause a physical association between the polypeptide of the invention and the surface of a target cell. The term TM embraces any molecule (i.e. a naturally occurring molecule, or a chemically/physically modified variant thereof) that is capable of binding to a Binding Site on the target cell, which Binding Site is capable of internalisation (e.g. endosome formation)—also referred to as receptor-mediated endocytosis. The TM may possess an endosomal membrane translocation function, in which case separate TM and Translocation Domain components need not be present in an agent of the present invention. Throughout the preceding description, specific TMs have been described. Reference to said TMs is merely exemplary, and the present invention embraces all variants and derivatives thereof, which retain the basic binding (i.e. targeting) ability of the exemplified TMs.

As mentioned previously, preferred TMs include antibodies (e.g. antibody fragments) and binding scaffolds; especially commercially available antibodies/fragments and scaffolds designed for the purpose of binding (e.g. specifically) to target cells.

Protein scaffolds represent a new generation of universal binding frameworks to complement the expanding repertoire of therapeutic monoclonal antibodies and derivatives such as scFvs, Fab molecules, dAbs (single-domain antibodies), camelids, diabodies and minibodies, each of which may be employed as a TM of the present invention. Scaffold systems create or modify known protein recognition domains either through creation of novel scaffolds or modification of known protein binding domains. Such scaffolds include but are not limited to:

(i) protein A based scaffolds—affibodies (Nord, K. et al 1997 "Binding proteins selected from combinatorial libraries of an alpha-helical bacterial receptor domain". Nat Biotechnol 15, 772-777);

(ii) lipocalin based scaffolds—anticalins (Skerra 2008 "Alternative binding proteins: anticalins—harnessing the structural plasticity of the lipocalin ligand pocket to engineer novel binding activities". FEBS J. 275:2677-83);

(iii) fibronectin based scaffolds—adnectin (Dineen et al 2008 "The Adnectin CT-322 is a novel VEGF receptor 2 inhibitor that decreases tumor burden in an orthotopic mouse model of pancreatic cancer". BMC Cancer 8:352);

(iv) avimers (Silverman et al 2005 "Multivalent avimer proteins evolved by exon shuffling of a family of human receptor domains". Nat Biotechnol 23:1556-61);

(v) ankyrin based scaffolds—darpins (Zahnd et al 2006 "Selection and characterization of Her2 binding-designed ankyrin repeat proteins". J Biol Chem. 281:35167-75); and (vi) centyrin scaffolds—based on a protein fold that has significant structural homology to Ig domains with loops that are analogous to CDRs. Ig domains are a common module in human proteins and have been widely applied as alternative scaffold proteins. Each of the above 'scaffold' publications is hereby incorporated (in its entirety) by reference thereto.

Binding scaffolds can be used to target particular cell types via interaction with specific cell surface proteins, receptors or other cell surface epitopes such as sugar groups. Such modified scaffolds can be engineered onto recombinant non-cytotoxic protease based polypeptides of the present invention.

The TM of the present invention binds (preferably specifically binds) to the target cell in question. The term "specifically binds" preferably means that a given TM binds to the target cell with a binding affinity (Ka) of $10^6$ $M^{-1}$ or greater, preferably $10^7$ $M^{-1}$ or greater, more preferably $10^8$ $M^{-1}$ or greater, and most preferably, $10^9$ $M^{-1}$ or greater.

Reference to TM in the present specification embraces fragments and variants thereof, which retain the ability to bind to the target cell in question. By way of example, a variant may have at least 80%, preferably at least 90%, more preferably at least 95%, and most preferably at least 97 or at least 99% amino acid sequence homology with the reference TM. Thus, a variant may include one or more analogues of an amino acid (e.g. an unnatural amino acid), or a substituted linkage. Also, by way of example, the term fragment, when used in relation to a TM, means a peptide having at least ten, preferably at least twenty, more preferably at least thirty, and most preferably at least forty amino acid residues of the reference TM. The term fragment also relates to the above-mentioned variants. Thus, by way of example, a fragment of the present invention may comprise a peptide sequence having at least 10, 20, 30 or 40 amino acids, wherein the peptide sequence has at least 80% sequence homology over a corresponding peptide sequence (of contiguous) amino acids of the reference peptide.

It is routine to confirm that a TM binds to the selected target cell. For example, a simple radioactive displacement experiment may be employed in which tissue or cells representative of a target cell in question are exposed to labelled (e.g. tritiated) TM in the presence of an excess of unlabelled TM. In such an experiment, the relative proportions of non-specific and specific binding may be assessed, thereby allowing confirmation that the TM binds to the target cell. Optionally, the assay may include one or more binding antagonists, and the assay may further comprise observing a loss of TM binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

In the context of the present invention, reference to a peptide TM embraces peptide analogues thereof, so long as the analogue binds to the same receptor as the corresponding 'reference' TM. Said analogues may include synthetic residues such as:

β-Nal=β-naphthylalanine
β-Pal=β-pyridylalanine
hArg(Bu)=N-guanidino-(butyl)-homoarginine
hArg(Et)$_2$=N,N'-guanidino-(dimethyl)-homoarginine
hArg(CH$_2$CF$_3$)$_2$=N,N'-guanidino-bis-(2,2,2,-trifluoro-ethyl)-homoarginine
hArg(CH$_3$, hexyl)=N,N'-guanidino-(methyl, hexyl)-homoarginine
Lys(Me)=N$^e$-methyllysine Lys(iPr)=N$^e$-isopropyllysine
AmPhe=aminomethylphenylalanine
AChxAla=aminocyclohexylalanine
Abu=α-aminobutyric acid
Tpo=4-thiaproline
MeLeu=N-methylleucine
Orn=ornithine
Nle—norleucine
Nva=norvaline
Trp(Br)=5-bromo-tryptophan
Trp(F)=5-fluoro-tryptophan
Trp(NO$_2$)=5-nitro-tryptophan
Gaba=γ-aminodutyric acid
Bmp=J-mercaptopropionyl
Ac=acetyl
Pen—pencillamine The polypeptides of the present invention may lack a functional H$_C$ or H$_{CC}$ domain of a clostridial neurotoxin. Accordingly, said polypeptides are not able to bind rat synaptosomal membranes (via a clostridial H$_C$ component) in binding assays as described in Shone et al. (1985) Eur. J. Biochem. 151, 75-82. In one embodiment, the polypeptides lack the last 50 C-terminal amino acids of a clostridial neurotoxin holotoxin. In another embodiment, the polypeptides lack the last 100, 150, 200, 250, or 300 C-terminal amino acid residues of a clostridial neurotoxin holotoxin. Alternatively, the H$_C$ binding activity may be negated/reduced by mutagenesis—by way of example, referring to BoNT/A for convenience, modification of one or two amino acid residue mutations (W1266 to L and Y1267 to F) in the ganglioside binding pocket causes the H$_C$ region to lose its receptor binding function. Analogous mutations may be made to non-serotype A clostridial peptide components, e.g. a construct based on botulinum B with mutations (W1262 to L and Y1263 to F) or botulinum E (W1224 to L and Y1225 to F). Other mutations to the active site achieve the same ablation of H$_C$ receptor binding activity, e.g. Y1267S in botulinum type A toxin and the corresponding highly conserved residue in the other clostridial neurotoxins. Details of this and other mutations are described in Rummel et al (2004) (Molecular Microbiol. 51:631-634), which is hereby incorporated by reference thereto.

The H$_C$ peptide of a native clostridial neurotoxin comprises approximately 400-440 amino acid residues, and consists of two functionally distinct domains of approximately 25 kDa each, namely the N-terminal region (commonly referred to as the H$_{CN}$ peptide or domain) and the C-terminal region (commonly referred to as the H$_{CC}$ peptide or domain). Moreover, it has been well documented that the C-terminal region (H$_{CC}$), which constitutes the C-terminal 160-200 amino acid residues, is responsible for binding of a clostridial neurotoxin to its natural cell receptors, namely to nerve terminals at the neuromuscular junction. Thus, reference throughout this specification to a clostridial heavy-chain lacking a functional heavy chain H$_C$ peptide (or domain) such that the heavy-chain is incapable of binding to cell surface receptors to which a native clostridial neurotoxin binds means that the clostridial heavy-chain simply lacks a functional H$_{CC}$ peptide. In other words, the H$_{CC}$ peptide region is either partially or wholly deleted, or otherwise modified (e.g. through conventional chemical or proteolytic treatment) to inactivate its native binding ability for nerve terminals at the neuromuscular junction.

Thus, in one embodiment, a clostridial H$_N$ peptide of the present invention lacks part of a C-terminal peptide portion (H$_{CC}$) of a clostridial neurotoxin and thus lacks the H$_C$ binding function of native clostridial neurotoxin. By way of example, in one embodiment, the C-terminally extended clostridial H$_N$ peptide lacks the C-terminal 40 amino acid residues, or the C-terminal 60 amino acid residues, or the C-terminal 80 amino acid residues, or the C-terminal 100 amino acid residues, or the C-terminal 120 amino acid residues, or the C-terminal 140 amino acid residues, or the C-terminal 150 amino acid residues, or the C-terminal 160 amino acid residues of a clostridial neurotoxin heavy-chain. In another embodiment, the clostridial H$_N$ peptide of the present invention lacks the entire C-terminal peptide portion (H$_{CC}$) of a clostridial neurotoxin and thus lacks the H$_C$ binding function of native clostridial neurotoxin. By way of example, in one embodiment, the clostridial H$_N$ peptide lacks the C-terminal 165 amino acid residues, or the C-terminal 170 amino acid residues, or the C-terminal 175 amino acid residues, or the C-terminal 180 amino acid residues, or the C-terminal 185 amino acid residues, or the C-terminal 190 amino acid residues, or the C-terminal 195 amino acid residues of a clostridial neurotoxin heavy-chain. By way of further example, the clostridial H$_N$ peptide of the present invention lacks a clostridial H$_{CC}$ reference sequence selected from the group consisting of:

Botulinum type A neurotoxin—amino acid residues (Y1111-L1296)
Botulinum type B neurotoxin—amino acid residues (Y1098-E1291)
Botulinum type C neurotoxin—amino acid residues (Y1112-E1291)
Botulinum type D neurotoxin—amino acid residues (Y1099-E1276)
Botulinum type E neurotoxin—amino acid residues (Y1086-K1252)
Botulinum type F neurotoxin—amino acid residues (Y1106-E1274)
Botulinum type G neurotoxin—amino acid residues (Y1106-E1297)
Tetanus neurotoxin—amino acid residues (Y1128-D1315).

The above-identified reference sequences should be considered a guide as slight variations may occur according to sub-serotypes.

The protease of the present invention embraces all non-cytotoxic proteases that are capable of cleaving one or more proteins of the exocytic fusion apparatus in eukaryotic cells. The protease of the present invention is preferably a bacterial protease (or fragment thereof). More preferably the bacterial protease is selected from the genera *Clostridium* or *Neisseria/Streptococcus* (e.g. a clostridial L-chain, or a neisserial IgA protease preferably from *N. gonorrhoeae* or *S. pneumoniae*).

The present invention also embraces variant non-cytotoxic proteases (i.e. variants of naturally-occurring protease molecules), so long as the variant proteases still demonstrate the requisite protease activity. By way of example, a variant may have at least 70%, preferably at least 80%, more preferably at least 90%, and most preferably at least 95 or at least 98% amino acid sequence homology with a reference protease sequence. Thus, the term variant includes non-cytotoxic proteases having enhanced (or decreased) endo-peptidase activity—particular mention here is made to the increased K$_{cat}$/K$_m$ of BoNT/A mutants Q161A, E54A, and K165L see Ahmed, S. A. (2008) Protein J. DOI 10.1007/s10930-007-9118-8, which is incorporated by reference thereto. The term fragment, when used in relation to a protease, typically means a peptide having at least 150, preferably at least 200, more preferably at least 250, and most preferably at least 300 amino acid residues of the reference protease. As with the TM 'fragment' component (discussed above), protease 'fragments' of the present invention embrace fragments of variant proteases based on a reference sequence.

The protease of the present invention preferably demonstrates a serine or metalloprotease activity (e.g. endopeptidase activity). The protease is preferably specific for a SNARE protein (e.g. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins. Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A).

BoNTs share a common structure, being di-chain proteins of ~150 kDa, consisting of a heavy chain (H-chain) of ~100 kDa covalently joined by a single disulphide bond to a light chain (L-chain) of ~50 kDa. The H-chain consists of two domains, each of ~50 kDa. The C-terminal domain ($H_C$) is required for the high-affinity neuronal binding, whereas the N-terminal domain ($H_N$) is proposed to be involved in membrane translocation. The L-chain is a zinc-dependent metalloprotease responsible for the cleavage of the substrate SNARE protein.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

Examples of suitable protease (reference) sequences include:

Botulinum type A neurotoxin—amino acid residues (1-448)
Botulinum type B neurotoxin—amino acid residues (1-440)
Botulinum type C neurotoxin—amino acid residues (1-441)
Botulinum type D neurotoxin—amino acid residues (1-445)
Botulinum type E neurotoxin—amino acid residues (1-422)
Botulinum type F neurotoxin—amino acid residues (1-439)
Botulinum type G neurotoxin—amino acid residues (1-441)
Tetanus neurotoxin—amino acid residues (1-457)
IgA protease—amino acid residues (1-959)*

* Pohlner, J. et al. (1987). Nature 325, pp. 458-462, which is hereby incorporated by reference thereto.

The above-identified reference sequence should be considered a guide as slight variations may occur according to sub-serotypes. By way of example, US 2007/0166332 (hereby incorporated by reference thereto) cites slightly different clostridial sequences:

Botulinum type A neurotoxin—amino acid residues (M1-K448)
Botulinum type B neurotoxin—amino acid residues (M1-K441)
Botulinum type C neurotoxin—amino acid residues (M1-K449)
Botulinum type D neurotoxin—amino acid residues (M1-R445)
Botulinum type E neurotoxin—amino acid residues (M1-R422)
Botulinum type F neurotoxin—amino acid residues (M1-K439)
Botulinum type G neurotoxin—amino acid residues (M1-K446)
Tetanus neurotoxin—amino acid residues (M1-A457)

A variety of clostridial toxin fragments comprising the light chain can be useful in aspects of the present invention with the proviso that these light chain fragments can specifically target the core components of the neurotransmitter release apparatus and thus participate in executing the overall cellular mechanism whereby a clostridial toxin proteolytically cleaves a substrate. The light chains of clostridial toxins are approximately 420-460 amino acids in length and comprise an enzymatic domain. Research has shown that the entire length of a clostridial toxin light chain is not necessary for the enzymatic activity of the enzymatic domain. As a non-limiting example, the first eight amino acids of the BoNT/A light chain are not required for enzymatic activity. As another non-limiting example, the first eight amino acids of the TeNT light chain are not required for enzymatic activity. Likewise, the carboxyl-terminus of the light chain is not necessary for activity. As a non-limiting example, the last 32 amino acids of the BoNT/A light chain (residues 417-448) are not required for enzymatic activity. As another non-limiting example, the last 31 amino acids of the TeNT light chain (residues 427-457) are not required for enzymatic activity. Thus, aspects of this embodiment can include clostridial toxin light chains comprising an enzymatic domain having a length of, for example, at least 350 amino acids, at least 375 amino acids, at least 400 amino acids, at least 425 amino acids and at least 450 amino acids. Other aspects of this embodiment can include clostridial toxin light chains comprising an enzymatic domain having a length of, for example, at most 350 amino acids, at most 375 amino acids, at most 400 amino acids, at most 425 amino acids and at most 450 amino acids.

In one embodiment, the non-cytotoxic protease cleaves a non-neuronal SNARE protein such as a SNAP-23 protein. In one embodiment, the non-cytotoxic protease is a modified botulinum toxin L-chain capable of cleaving SNAP-23. An example of such a modified L-chain is described by Chen and Barbieri, PNAS, vol. 106, no. 23, p 9180-9184, 2009.

In one embodiment, the non-cytotoxic protease is a BoNT/A, BoNT/C or BoNT/E protease, and the preferred SNARE motif is a SNAP (e.g. SNAP 25) motif. In another embodiment, the non-cytotoxic protease is a BoNT/B, BoNT/D, BoNT/F or BoNT/G or tetanus neurotoxin (TeNT) protease, and the preferred SNARE motif is a VAMP motif. In another embodiment, the non-cytotoxic protease is a BoNT/C, protease, and the preferred SNARE motif is a syntaxin motif.

The polypeptides of the present invention, especially the protease component thereof, may be PEGylated—this may help to increase stability, for example duration of action of the protease component. PEGylation is particularly preferred when the protease comprises a BoNT/A, B or $C_1$ protease. PEGylation preferably includes the addition of PEG to the N-terminus of the protease component. By way of example, the N-terminus of a protease may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is incorporated in its entirety by reference thereto.

A Translocation Domain is a molecule that enables translocation of a protease into a target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored [see Shone C. (1987) Eur. J. Biochem; vol. 167(1): pp. 175-180]. A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120]. Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The present invention also embraces variant translocation domains, so long as the variant domains still demonstrate the requisite translocation activity. By way of example, a variant may have at least 70%, preferably at least 80%, more preferably at least 90%, and most preferably at least 95% or at least 98% amino acid sequence homology with a reference translocation domain. The term fragment, when used in relation to a translocation domain, means a peptide having at least 20, preferably at least 40, more preferably at least 80, and most preferably at least 100 amino acid residues of the reference translocation domain. In the case of a clostridial translocation domain, the fragment preferably has at least 100, preferably at least 150, more preferably at least 200, and most preferably at least 250 amino acid residues of the reference translocation domain (e.g. $H_N$ domain). As with the TM 'fragment' component (discussed above), translocation 'fragments' of the present invention embrace fragments of variant translocation domains based on the reference sequences.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, such as the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. In this regard, should it be desired to remove the $H_C$ cell-binding function, this may be done by deletion of the $H_C$ or $H_{CC}$ amino acid sequence (either at the DNA synthesis level, or at the post-synthesis level by nuclease or protease treatment). Alternatively, the $H_C$ function may be inactivated by chemical or biological treatment.

Examples of suitable (reference) Translocation Domains include:
Botulinum type A neurotoxin—amino acid residues (449-871)
Botulinum type B neurotoxin—amino acid residues (441-858)
Botulinum type C neurotoxin—amino acid residues (442-866)
Botulinum type D neurotoxin—amino acid residues (446-862)
Botulinum type E neurotoxin—amino acid residues (423-845)
Botulinum type F neurotoxin—amino acid residues (440-864)
Botulinum type G neurotoxin—amino acid residues (442-863)
Tetanus neurotoxin—amino acid residues (458-879)

The above-identified reference sequence should be considered a guide as slight variations may occur according to sub-serotypes. By way of example, US 2007/0166332 (hereby incorporated by reference thereto) cites slightly different clostridial sequences:
Botulinum type A neurotoxin—amino acid residues (A449-K871)
Botulinum type B neurotoxin—amino acid residues (A442-5858)
Botulinum type C neurotoxin—amino acid residues (T450-N866)
Botulinum type D neurotoxin—amino acid residues (D446-N862)
Botulinum type E neurotoxin—amino acid residues (K423-K845)
Botulinum type F neurotoxin—amino acid residues (A440-K864)
Botulinum type G neurotoxin—amino acid residues (S447-S863)
Tetanus neurotoxin—amino acid residues (S458-V879)

In the context of the present invention, a variety of clostridial toxin $H_N$ regions comprising a translocation domain can be useful in aspects of the present invention with the proviso that these active fragments can facilitate the release of a non-cytotoxic protease (e.g. a clostridial L-chain) from intracellular vesicles into the cytoplasm of the target cell and thus participate in executing the overall cellular mechanism whereby a clostridial toxin proteolytically cleaves a substrate. The $H_N$ regions from the heavy chains of Clostridial toxins are approximately 410-430 amino acids in length and comprise a translocation domain. Research has shown that the entire length of a $H_N$ region from a Clostridial toxin heavy chain is not necessary for the translocating activity of the translocation domain. Thus, aspects of this embodiment can include clostridial toxin $H_N$ regions comprising a translocation domain having a length of, for example, at least 350 amino acids, at least 375 amino acids, at least 400 amino acids and at least 425 amino acids. Other aspects of this embodiment can include clostridial toxin $H_N$ regions comprising translocation domain having a length of, for example, at most 350 amino acids, at most 375 amino acids, at most 400 amino acids and at most 425 amino acids.

For further details on the genetic basis of toxin production in *Clostridium botulinum* and *C. tetani*, we refer to Henderson et al (1997) in *The Clostridia: Molecular Biology and Pathogenesis*, Academic press. The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin. Examples of non-clostridial (reference) Translocation Domain origins include, but not be restricted to, the translocation domain of diphtheria toxin [O'Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.*, 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS*, 89, pp. 7934-7938], and amphiphilic peptides [Murata et al (1992) *Biochem.*, 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral (reference) Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the (reference) Translocation Domains includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

The polypeptides of the present invention may further comprise a translocation facilitating domain. Said domain facilitates delivery of the non-cytotoxic protease into the cytosol of the target cell and are described, for example, in WO 08/008803 and WO 08/008805, each of which is herein incorporated by reference thereto.

By way of example, suitable translocation facilitating domains include an enveloped virus fusogenic peptide domain, for example, suitable fusogenic peptide domains include influenzavirus fusogenic peptide domain (e.g. influenza A virus fusogenic peptide domain of 23 amino acids), alphavirus fusogenic peptide domain (e.g. Semliki Forest virus fusogenic peptide domain of 26 amino acids), vesiculovirus fusogenic peptide domain (e.g. vesicular stomatitis virus fusogenic peptide domain of 21 amino acids), respirovirus fusogenic peptide domain (e.g. Sendai virus fusogenic peptide domain of 25 amino acids), morbiliivirus fusogenic peptide domain (e.g. Canine distemper virus fusogenic peptide domain of 25 amino acids), avulavirus fusogenic peptide domain (e.g. Newcastle disease virus fusogenic peptide domain of 25 amino acids), henipavirus fusogenic peptide domain (e.g. Hendra virus fusogenic peptide domain of 25 amino acids), metapneumovirus fusogenic peptide domain (e.g. Human metapneumovirus fusogenic peptide domain of 25 amino acids) or spumavirus fusogenic peptide domain such as simian foamy virus fusogenic peptide domain; or fragments or variants thereof.

By way of further example, a translocation facilitating domain may comprise a Clostridial toxin $H_{CN}$ domain or a fragment or variant thereof. In more detail, a Clostridial toxin $H_{CN}$ translocation facilitating domain may have a length of at least 200 amino acids, at least 225 amino acids, at least 250 amino acids, at least 275 amino acids. In this regard, a Clostridial toxin $H_{CN}$ translocation facilitating domain preferably has a length of at most 200 amino acids, at most 225 amino acids, at most 250 amino acids, or at most 275 amino acids. Specific (reference) examples include:

Botulinum type A neurotoxin—amino acid residues (872-1110)
Botulinum type B neurotoxin—amino acid residues (859-1097)
Botulinum type C neurotoxin—amino acid residues (867-1111)
Botulinum type D neurotoxin—amino acid residues (863-1098)
Botulinum type E neurotoxin—amino acid residues (846-1085)
Botulinum type F neurotoxin—amino acid residues (865-1105)
Botulinum type G neurotoxin—amino acid residues (864-1105)
Tetanus neurotoxin—amino acid residues (880-1127)

The above sequence positions may vary a little according to serotype/sub-type, and further examples of suitable (reference) Clostridial toxin $H_{CN}$ domains include:

Botulinum type A neurotoxin—amino acid residues (874-1110)
Botulinum type B neurotoxin—amino acid residues (861-1097)
Botulinum type C neurotoxin—amino acid residues (869-1111)
Botulinum type D neurotoxin—amino acid residues (865-1098)
Botulinum type E neurotoxin—amino acid residues (848-1085)
Botulinum type F neurotoxin—amino acid residues (867-1105)
Botulinum type G neurotoxin—amino acid residues (866-1105)
Tetanus neurotoxin—amino acid residues (882-1127)

Any of the above-described facilitating domains may be combined with any of the previously described translocation domain peptides that are suitable for use in the present invention. Thus, by way of example, a non-clostridial facilitating domain may be combined with non-clostridial translocation domain peptide or with clostridial translocation domain peptide. Alternatively, a Clostridial toxin $H_{CN}$ translocation facilitating domain may be combined with a non-clostridal translocation domain peptide. Alternatively, a Clostridial toxin $H_{CN}$ facilitating domain may be combined or with a clostridial translocation domain peptide, examples of which include:

Botulinum type A neurotoxin—amino acid residues (449-1110)

Botulinum type B neurotoxin—amino acid residues (442-1097)

Botulinum type C neurotoxin—amino acid residues (450-1111)

Botulinum type D neurotoxin—amino acid residues (446-1098)

Botulinum type E neurotoxin—amino acid residues (423-1085)

Botulinum type F neurotoxin—amino acid residues (440-1105)

Botulinum type G neurotoxin—amino acid residues (447-1105)

Tetanus neurotoxin—amino acid residues (458-1127)

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs Sampling, see, e.g., C. E. Lawrence et al., Detecting Subtle Sequence Signals: A Gibbs Sampling Strategy for Multiple Alignment, 262(5131) Science 208-214 (1993): Align-M, see, e.g., Ivo Van Walle et al., Align-M—A New Algorithm for Multiple Alignment of Highly Divergent Sequences, 20(9) Bioinformatics:1428-1435 (2004). Thus, percent sequence identity is determined by conventional methods. See, for example, Altschul et al., *Bull. Math. Bio.* 48: 603-16, 1986 and Henikoff and Henikoff, *Proc. Natl. Acad. Sci. USA* 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff.

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions
Basic: arginine; lysine; histidine
Acidic: glutamic acid; aspartic acid;
Polar: glutamine; asparagine
Hydrophobic: leucine; isoleucine; valine
Aromatic: phenylalanine; tryptophan; tyrosine
Small: glycine; alanine; serine; threonine; methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus oocytes* by microinjection of mutated mRNA and chemically amino-acylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., *Biochem.* 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, *Science* 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-12, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenised polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

SUMMARY OF EXAMPLES

Example 1 Creation of an LHD protein that incorporates a GnRH polypeptide to the C-terminus of the $H_N$ domain Example 2 Creation of an LHA protein that incorporates a GnRH polypeptide to the C-terminus of the $H_N$ domain Example 3 Creation of an LHD protein that incorporates a GnRH polypeptide to the C-terminus of the $H_N$ domain, where two different protease recognition sites are incorporated Example 4 Method of preparation of an LHD protein that incorporates a GnRH polypeptide to the C-terminus of the $H_N$ domain Example 5 Demonstration of presence of covalently attached ligand by Western blotting Example 6 Demonstration of presence of covalently attached TM by mass spectrometry Example 7 Assessment of the binding ability of an LHD protein that incorporates a GnRH polypeptide Example 8 Assessment of the in vitro functionality of an LHD protein that incorporates a GnRH polypeptide Example 9 Creation of an LHD protein that incorporates a dynorphin and a bradykinin polypeptide to the C-terminus of the $H_N$ domain Example 10 Creation of an LHA protein that incorporates a beta-endorphin and a bradykinin polypeptide to the C-terminus of the $H_N$ domain Example 11 Creation of an LHD protein that incorporates two GHRH polypeptides to the C-terminus of the $H_N$ domain Example 12 Creation of an LHD protein that incorporates a GnRH polypeptide to the C-terminus of the $H_N$ domain, spaced by 5 amino acids from the second protease activation site Example 13 Creation of an LHA protein that incorporates a Gastrin releasing peptide to the C-terminus of the $H_N$ domain Example 14 Method of treating patients suffering from prostate cancer Example 15 Method of treating patients suffering from neurogenic inflammation Example 16 Method of treating patients suffering from endometriosis

SUMMARY OF SEQ ID NOS

All of the following SEQ ID NOs may exclude any initial Methionine amino acid residue (or corresponding N-terminal nucleic acid codon/sequence).

SEQ ID NO: 1 DNA sequence of LHD-GnRH
SEQ ID NO: 2 Protein sequence of LHD-GnRH
SEQ ID NO: 3 DNA sequence of LHA-GnRH
SEQ ID NO: 4 Protein sequence of LHA-GnRH
SEQ ID NO: 5 DNA sequence of LHD-GnRH with two different protease sites
SEQ ID NO: 6 Protein sequence of LHD-GnRH with two different protease sites
SEQ ID NO: 7 DNA sequence of LHD that incorporates a dynorphin and a bradykinin polypeptide to the C-terminus of the $H_N$ domain
SEQ ID NO: 8 Protein sequence of LHD that incorporates a dynorphin and a bradykinin polypeptide to the C-terminus of the $H_N$ domain
SEQ ID NO: 9 DNA sequence of LHA that incorporates a beta-endorphin and a bradykinin polypeptide to the C-terminus of the $H_N$ domain
SEQ ID NO: 10 Protein sequence of LHA that incorporates a beta-endorphin and a bradykinin polypeptide to the C-terminus of the $H_N$ domain
SEQ ID NO: 11 DNA sequence of LHD that incorporates two GHRH polypeptides to the C-terminus of the $H_N$ domain
SEQ ID NO: 12 Protein sequence of LHD that incorporates two GHRH polypeptides to the C-terminus of the $H_N$ domain
SEQ ID NO: 13 DNA sequence of LHD that incorporates GnRH to the C-terminus of the $H_N$ domain
SEQ ID NO: 14 Protein sequence of LHD that incorporates GnRH to the C-terminus of the $H_N$ domain
SEQ ID NO: 15 DNA sequence of LHA that incorporates a Gastrin releasing peptide to the C-terminus of the $H_N$ domain
SEQ ID NO: 16 Protein sequence of LHA that incorporates a Gastrin releasing peptide to the C-terminus of the $H_N$ domain There now follows description of specific embodiments of the invention, illustrated by the Examples.

Example 1 Creation of an LHD Protein that Incorporates a GnRH Polypeptide to the C-Terminus of the $H_N$ Domain The primary sequence of a chimaeric protein constructed by a genetic fusion of the $LH_N$ fragment of BoNT/D and the 10 amino acid peptide GnRH is reviewed for the presence of amino acid strings that bear resemblance to the prototypical recognition site for Factor Xa (IEGR) (SEQ ID NO: 33). As no such string is found, the choice is made to use FXa as the protease to both activate the fusion protein at the LC-H$_N$ junction and also to cleave the peptide bond between the H$_N$ and the TM (GnRH).

DNA optimised for *E. coli* expression is obtained commercially from Entelechon (Germany) to encode a fusion protein which has the following structure, from N- to C-terminus:
- 10 His N-terminal purification tag (SEQ ID NO: 48),
- a 10 asparagine amino acid spacer (SEQ ID NO: 49),
- the LC of BoNT/D,
- an inter-domain linker with a primary sequence similar to the found in BoNT/A, modified to incorporate the tetra peptide IEGR (SEQ ID NO: 33) which is a substrate for FXa,
- the H$_N$ of BoNT/D modified to incorporate a C-terminal Cys,
- a Gly-Gly-Gly-Gly-Ser (SEQ ID NO: 50) spacer incorporating an IEGR (SEQ ID NO: 33) peptide sequence at the C-terminus
- a 10 amino acid GnRH peptide modified to incorporate a Cys residue at position 6 in place of the natural Gly (QHWSYCLRPG) (SEQ ID NO: 51).

*E. coli* codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the construction does not result in poor codon utilisation. The DNA was incorporated into a standard cloning vector, for example pCR4, prior to transformation into *E. coli* host. The integrity of the ORF DNA was checked by sequencing. The final ORF is illustrated as SEQ ID 1 and the amino acid sequence of the expression product is illustrated in SEQ ID 2.

Example 2 Creation of an LHA Protein that Incorporates a GnRH Polypeptide to the C-Terminus of the H$_N$ Domain The primary sequence of a chimaeric protein constructed by a genetic fusion of the LH$_N$ fragment of BoNT/A and the 10 amino acid peptide GnRH is reviewed for the presence of amino acid strings that bear resemblance to the prototypical recognition site for Factor Xa (IEGR) (SEQ ID NO: 33). As no such string is found, the choice is made to use FXa as the protease to both activate the fusion protein at the LC-H$_N$ junction and also to cleave the peptide bond between the H$_N$ and the TM (GnRH).

DNA optimised for *E. coli* expression is obtained commercially from Entelechon (Germany) to encode a fusion protein which has the following structure, from N- to C-terminus:
- 10 His N-terminal purification tag (SEQ ID NO: 48),
- a 10 asparagine amino acid spacer (SEQ ID NO: 49),
- the LC of BoNT/A,
- an inter-domain linker with a primary sequence similar to the found in BoNT/A, modified to incorporate the tetra peptide IEGR (SEQ ID NO: 33) which is a substrate for FXa,
- the H$_N$ of BoNT/A modified to incorporate a C-terminal Cys,
- a Gly-Gly-Gly-Gly-Ser (SEQ ID NO: 50) spacer incorporating an IEGR (SEQ ID NO: 33) peptide sequence at the C-terminus
- a 10 amino acid GnRH peptide modified to incorporate a Cys residue at position 6 in place of the natural Gly.

*E. coli* codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the construction does not result in poor codon utilisation. The DNA was incorporated into a standard cloning vector, for example pCR4, prior to transformation into *E. coli* host. The integrity of the ORF DNA was checked by sequencing. The final ORF is illustrated as SEQ ID 3 and the amino acid sequence of the expression product is illustrated in SEQ ID 4.

Example 3 Creation of an LHD Protein that Incorporates a GnRH Polypeptide to the C-Terminus of the H$_N$ Domain, where Two Different Protease Recognition Sites are Incorporated The primary sequence of a chimaeric protein constructed by a genetic fusion of the LH$_N$ fragment of BoNT/D and the 10 amino acid peptide GnRH is reviewed for the presence of amino acid strings that bear resemblance to the prototypical recognition site for Factor Xa (IEGR) (SEQ ID NO: 33) and enterokinase (DDDDK) (SEQ ID NO: 32). As no such string is found, the choice is made to use FXa as the protease to activate the fusion protein at the LC-H$_N$ junction and enterokinase to cleave the peptide bond between the H$_N$ and the TM (GnRH).

DNA optimised for *E. coli* expression is obtained commercially from Entelechon (Germany) to encode a fusion protein which has the following structure, from N- to C-terminus:
- 10 His N-terminal purification tag (SEQ ID NO: 48),
- a 10 amino acid asparagine spacer (SEQ ID NO: 49),
- the LC of BoNT/D,
- an inter-domain linker with a primary sequence similar to the found in BoNT/A, modified to incorporate the tetra peptide IEGR (SEQ ID NO: 33) which is a substrate for FXa,
- the H$_N$ of BoNT/D modified to incorporate a C-terminal Cys,
- a Gly-Gly-Gly-Gly-Ser (SEQ ID NO: 50) spacer incorporating a DDDDK (SEQ ID NO: 32) peptide sequence at the C-terminus
- a 10 amino acid GnRH peptide modified to incorporate a Cys residue at position 6 in place of the natural Gly.

*E. coli* codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the construction does not result in poor codon utilisation. The DNA was incorporated into a standard cloning vector, for example pCR4, prior to transformation into *E. coli* host. The integrity of the ORF DNA was checked by sequencing. The final ORF is illustrated as SEQ ID 5 and the amino acid sequence of the expression product is illustrated in SEQ ID 6.

Example 4 Method of Preparation of an LHD Protein that Incorporates a GnRH Polypeptide to the C-Terminus of the H$_N$ Domain The ORF created in Example 1 was cloned into an *E. coli* expression vector (a pET (Novagen) vector that has been modified to ensure mobilisation deficiency) and transformed into an *E. coli* host strain, most commonly BL21.

Expression of the LHD-GnRH fusion protein is achieved using the following protocol. Inoculate 100 ml of modified TB containing 0.2% glucose and 100 µg/ml ampicillin in a 250 ml flask with a single colony from the LHD-GnRH expression strain. Grow the culture at 37° C., 225 rpm for 16 hours. Inoculate 2×1 L of modified TB containing 0.2% glucose and 100 µg/ml ampicillin in a 2×2 L flask with 10 ml of overnight culture. Grow cultures at 37° C. until an approximate OD600 nm of 0.5 is reached at which point reduce the temperature to 16° C. After 1 hour induce the cultures with 1 mM IPTG and grow at 16° C. for a further 16 hours. Centrifugation of the culture yielded 35.2 g cell paste.

Purification of the LHD-GnRH fusion is achieved by affinity chromatography. In detail, a falcon tube containing 25 ml 50 mM HEPES pH 7.2 200 mM NaCl and approximately 10 g of *E. coli* BL21 cell paste is defrosted. Sonicate the cell paste on ice 30 seconds on, 30 seconds off for 10 cycles at a power of 22 microns ensuring the sample remains cool. Spin the lysed cells at 18 000 rpm, 4° C. for 30 minutes. Load the supernatant onto a HisTrap HP Chelating column (5 ml column is sufficient) equilibrated with 50 mM HEPES pH 7.2 200 mM NaCl. Following addition of 40 mM Imidazole to wash away the non-specific bound protein, fusion protein was eluted with a step gradient of 80 mM Imidazole, 250 mM Imidazole and 500 mM Imidazole. Dialyse the eluted fusion protein against 5 L of 50 mM HEPES pH 7.2 200 mM NaCl at 4° C. overnight and measure the OD of the dialysed fusion protein. Add 10 U Factor Xa/mg fusion protein and incubate at 25° C. static overnight. Load onto a HisTrap HP Chelating column (5 ml column is sufficient) equilibrated with 50 mM HEPES pH 7.2 200 mM NaCl. Wash column to baseline with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 25 mM Tris, 200 mM NaCl, pH 8.0 at 4° C. overnight and concentrate the fusion to about 2 mg/ml, aliquot sample and freeze at −20° C. Test purified protein using OD, BCA and purity analysis.

Samples of the activated protein are analysed by SDS-PAGE in both reducing and non-reducing conditions. Samples eluted in the 80 mM and 250 mM Imidazole fractions are analysed—see FIG. 1.

Example 5 Demonstration of Presence of Covalently Attached TM by Western Blotting The presence of the TM within the fusion protein may be assessed by a variety of methods. One method is to use specific antisera to the TM and visualise by SDS-PAGE and Western blotting. Antibodies to TM may be obtained commercially (e.g. anti-GnRH antibodies are available from Abcam (AB76560) or Novus Biologicals (H00002796-B01) or may be raised specifically to a given peptide sequence by a commercial service provider.

Using such techniques, the presence of GnRH is confirmed to be within the full length, activated fusion protein when run under non-reducing conditions, but it not present on the $H_N$ domain when run under reducing conditions.

Example 6 Demonstration of the Presence of Covalently Attached TM by Mass Spectrometry The presence of the TM within the fusion protein may be assessed by a variety of methods. One method is the use of mass spectrometry to determine the fusion protein mass before and after reduction.

Using the protein prepared according to Example 4, various samples of non-reduced and reduced protein were extracted from SDS-PAGE (see FIG. 1) and analysed by mass spectrometry (Intertek, Manchester).

The predicted mass of non-activated, non-reduced fusion protein is 105271 Da. The observed mass for the samples was 105284 Da, a difference of only 13 Da, which is within the error of the equipment. Therefore, the presence of the intact GnRH in the non-activated, non-reduced fusion protein is confirmed.

| Non-Reduced Sample: | | | |
| --- | --- | --- | --- |
| Theoretical Mass: | Corresponding Structure: | Observed Mass: | Mass Difference: |
| 105271 Da | Full Length | 105284 Da | 13 Da |

The predicted mass of activated, non-reduced fusion protein is 105271 Da. The observed mass for the samples was 105321 Da, a difference of only 50 Da, which is within the error of the equipment. Therefore, the presence of the intact GnRH in the activated, non-reduced fusion protein is confirmed.

| Non-Reduced Sample: | | | |
| --- | --- | --- | --- |
| Theoretical Mass: | Corresponding Structure: | Observed Mass: | Mass Difference: |
| 105271 Da | Full Length | 105321 Da | 50 Da |

When reduced samples of the LC and $H_N$ domain are assessed, the $H_N$ domain (which should comprise $H_N$+spacer+activation site) has a predicted mass of 49419 Da and an observed mass of 49421. This indicates that the reduced $H_N$ domain does not retain the GnRH peptide. This result is entirely as predicted since proteolysis and reduction of the disulphide bond will release the GnRH sequence from the C-terminus of the $H_N$ domain.

| Reduced Sample: $H_N$ Subunit Mass | | | |
| --- | --- | --- | --- |
| Theoretical Mass: | Corresponding Structure: | Observed Mass: | Mass Difference: |
| 49419 Da | Heavy Chain + Spacer + Activation Site | 49421 Da | 2 Da |

These data demonstrate that the GnRH ligand is attached to the fusion protein prior to activation and reduction, is attached to the fusion protein following activation in the absence of reducing agent, but is absent from the $H_N$ domain following activation and reduction. This confirms that the fusion protein has correctly activated at both proteolytic sites and that the GnRH ligand is attached to the $H_N$ domain through the engineered disulphide bond.

Example 7 Assessment of the Binding Ability of an LHD Protein that Incorporates a GnRH Polypeptide The protein prepared according to Example 4 is assessed for functionality of ligand-receptor interaction using one of a number of suitable assays. For example the Gonadotrophin-releasing hormone GnRHR receptor ligand binding assays supplied by Cisbio Bioassays is a competition assay that quantifies the binding activity in a sample (http://www.htrf.com/products/gpcr/binding/ligands/inserts/C1TT1GNRH.pdf). Alternatively, a range of publicly available binding assays are reported in the scientific literature (for example Christopher E. Heise, Susan K. Sullivan and Paul D. Crowe, J Biomol Screen 2007 12: 235; DOI: 10.1177/1087057106297362). Use of such assays indicate that the GnRH TM is capable of interacting with the target receptor.

The data indicate that the GnRH TM is capable of interacting with the target receptor.

Example 8 Assessment of the In Vitro Functionality of an LHD Protein that Incorporates a GnRH Polypeptide The protein prepared according to Example 4 is assessed for its ability to cleave SNARE proteins within the target cell. Briefly, an alpha T3-1 cell line (an immortalized gonadotroph cell line) that expresses high levels of the gonadotrophin-releasing hormone (GnRH) receptor is incubated with a compound of the invention. 24 hours later the cellular material is harvested and SNARE proteins analysed by Western blotting. The data indicate that the fusion protein comprising the GnRH TM is capable of interacting with the target receptor, leading to internalisation and cleavage of intracellular SNARE proteins.

Example 9 Creation of an LHD Protein that Incorporates a Dynorphin and a Bradykinin Polypeptide to the C-Terminus of the $H_N$ Domain The primary sequence of a chimaeric protein constructed by a genetic fusion of the $LH_N$ fragment of BoNT/D and the peptides dynorphin and bradykinin is reviewed for the presence of amino acid strings that bear resemblance to the prototypical recognition site for Factor Xa (IEGR) (SEQ ID NO: 33). As no such string is found, the choice is made to use FXa as the protease to both activate the fusion protein at the LC-$H_N$ junction and also to cleave the peptide bond between the $H_N$ and the dynorphin peptide. An 11 amino acid spacer is constructed between the dynorphin and bradykinin peptides incorporating a single Cys to facilitate disulphide binding to the $H_N$.

DNA optimised for *E. coli* expression is obtained commercially from Entelechon (Germany) to encode a fusion protein which has the following structure, from N- to C-terminus:
  10 His N-terminal purification tag (SEQ ID NO: 48),
  a 10 asparagine amino acid spacer (SEQ ID NO: 49),
  the LC of BoNT/D,
  an inter-domain linker with a primary sequence similar to the found in BoNT/A, modified to incorporate the tetra peptide IEGR (SEQ ID NO: 33) which is a substrate for FXa,
  the $H_N$ of BoNT/D modified to incorporate a C-terminal Cys,
  a Gly-Gly-Gly-Gly-Ser (SEQ ID NO: 50) spacer incorporating an IEGR (SEQ ID NO: 33) peptide sequence at the C-terminus
  a 17 amino acid dynorphin peptide
  a 11 amino acid Gly-Gly-Gly-Gly-Ser-Cys-Gly-Gly-Gly-Gly-Ser (SEQ ID NO: 52)
  a 9 amino acid bradykinin peptide.

*E. coli* codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the construction does not result in poor codon utilisation. The DNA was incorporated into a standard cloning vector, for example pCR4, prior to transformation into *E. coli* host. The integrity of the ORF DNA was checked by sequencing. The final ORF is illustrated as SEQ ID 7 and the amino acid sequence of the expression product is illustrated in SEQ ID 8.

Example 10 Creation of an LHA Protein that Incorporates a Beta-Endorphin and a Bradykinin Polypeptide to the C-Terminus of the $H_N$ Domain The primary sequence of a chimaeric protein constructed by a genetic fusion of the $LH_N$ fragment of BoNT/A and the peptides beta-endorphin and bradykinin is reviewed for the presence of amino acid strings that bear resemblance to the prototypical recognition site for Factor Xa (IEGR) (SEQ ID NO: 33). As no such string is found, the choice is made to use FXa as the protease to both activate the fusion protein at the LC-$H_N$ junction and also to cleave the peptide bond between the $H_N$ and the beta-endorphin peptide. An 11 amino acid spacer is constructed between the beta-endorphin and bradykinin peptides incorporating a single Cys to facilitate disulphide binding to the $H_N$.

DNA optimised for *E. coli* expression is obtained commercially from Entelechon (Germany) to encode a fusion protein which has the following structure, from N- to C-terminus:
  10 His N-terminal purification tag (SEQ ID NO: 48),
  a 10 asparagine amino acid spacer (SEQ ID NO: 49),
  the LC of BoNT/A,
  an inter-domain linker with a primary sequence similar to the found in BoNT/A, modified to incorporate the tetra peptide IEGR (SEQ ID NO: 33) which is a substrate for FXa,
  the $H_N$ of BoNT/A modified to incorporate a C-terminal Cys,
  a Gly-Gly-Gly-Gly-Ser (SEQ ID NO: 50) spacer incorporating an IEGR (SEQ ID NO: 33) peptide sequence at the C-terminus
  a 31 amino acid beta-endorphin peptide
  a 11 amino acid Gly-Gly-Gly-Gly-Ser-Cys-Gly-Gly-Gly-Gly-Ser (SEQ ID NO: 52)
  a 9 amino acid bradykinin peptide.

*E. coli* codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the construction does not result in poor codon utilisation. The DNA was incorporated into a standard cloning vector, for example pCR4, prior to transformation into *E. coli* host. The integrity of the ORF DNA was checked by sequencing. The final ORF is illustrated as SEQ ID 9 and the amino acid sequence of the expression product is illustrated in SEQ ID 10.

Example 11 Creation of an LHD Protein that Incorporates Two GHRH Polypeptides to the C-Terminus of the $H_N$ Domain The primary sequence of a chimaeric protein constructed by a genetic fusion of the $LH_N$ fragment of BoNT/D and two GHRH peptides is reviewed for the presence of amino acid strings that bear resemblance to the prototypical recognition site for Factor Xa (IEGR) (SEQ ID NO: 33). As no such string is found, the choice is made to use FXa as the protease to both activate the fusion protein at the LC-H$_N$ junction and also to cleave the peptide bond between the H$_N$ and the GHRH peptide. An 11 amino acid spacer is constructed between the two GHRH peptides incorporating a single Cys to facilitate disulphide binding to the H$_N$.

DNA optimised for *E. coli* expression is obtained commercially from Entelechon (Germany) to encode a fusion protein which has the following structure, from N- to C-terminus:

10 His N-terminal purification tag (SEQ ID NO: 48),
a 10 amino acid asparagine spacer (SEQ ID NO: 49),
the LC of BoNT/D,
an inter-domain linker with a primary sequence similar to the found in BoNT/A, modified to incorporate the tetra peptide IEGR (SEQ ID NO: 33) which is a substrate for FXa,
the H$_N$ of BoNT/D modified to incorporate a C-terminal Cys,
a Gly-Gly-Gly-Gly-Ser (SEQ ID NO: 50) spacer incorporating an IEGR (SEQ ID NO: 33) peptide sequence at the C-terminus
a 40 amino acid GHRH peptide
a 11 amino acid Gly-Gly-Gly-Gly-Ser-Cys-Gly-Gly-Gly-Gly-Ser (SEQ ID NO: 52)
a 40 amino acid GHRH peptide.

*E. coli* codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the construction does not result in poor codon utilisation. The DNA was incorporated into a standard cloning vector, for example pCR4, prior to transformation into *E. coli* host. The integrity of the ORF DNA was checked by sequencing. The final ORF is illustrated as SEQ ID 11 and the amino acid sequence of the expression product is illustrated in SEQ ID 12.

Example 12 Creation of an LHD Protein that Incorporates a GnRH Polypeptide to the C-Terminus of the H$_N$ Domain, Spaced by 5 Amino Acids from the Second Protease Activation Site The primary sequence of a chimaeric protein constructed by a genetic fusion of the LH$_N$ fragment of BoNT/D and the 10 amino acid peptide GnRH is reviewed for the presence of amino acid strings that bear resemblance to the prototypical recognition site for Factor Xa (IEGR) (SEQ ID NO: 33). As no such string is found, the choice is made to use FXa as the protease to both activate the fusion protein at the LC-H$_N$ junction and also to cleave the peptide bond between the H$_N$ and the spacer to the N-terminus of the TM (GnRH).

DNA optimised for *E. coli* expression is obtained commercially from Entelechon (Germany) to encode a fusion protein which has the following structure, from N- to C-terminus:

10 His N-terminal purification tag (SEQ ID NO: 48),
a 10 asparagine amino acid spacer (SEQ ID NO: 49),
the LC of BoNT/D,
an inter-domain linker with a primary sequence similar to the found in BoNT/A, modified to incorporate the tetra peptide IEGR (SEQ ID NO: 33) which is a substrate for FXa,
the H$_N$ of BoNT/D modified to incorporate a C-terminal Cys,
a Gly-Gly-Gly-Gly-Ser-Ile-Glu-Gly-Arg-Gly-Gly-Gly-Gly-Ser (SEQ ID NO: 50) spacer incorporating an IEGR (SEQ ID NO: 33) peptide,
a 10 amino acid GnRH peptide modified to incorporate a Cys residue at position 6 in place of the natural Gly (QHWSYCLRPG) (SEQ ID NO: 51).

*E. coli* codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the construction does not result in poor codon utilisation. The DNA was incorporated into a standard cloning vector, for example pCR4, prior to transformation into *E. coli* host. The integrity of the ORF DNA was checked by sequencing. The final ORF is illustrated as SEQ ID 13 and the amino acid sequence of the expression product is illustrated in SEQ ID 14.

Example 13 Creation of an LHA Protein that Incorporates a Gastrin Releasing Peptide to the C-Terminus of the H$_N$ Domain The primary sequence of a chimaeric protein constructed by a genetic fusion of the LH$_N$ fragment of BoNT/A and the 27 amino acid gastrin releasing peptide (GRP) is reviewed for the presence of amino acid strings that bear resemblance to the prototypical recognition site for Factor Xa (IEGR) (SEQ ID NO: 33). As no such string is found, the choice is made to use FXa as the protease to both activate the fusion protein at the LC-H$_N$ junction and also to cleave the peptide bond between the H$_N$ and the TM (GRP).

DNA optimised for *E. coli* expression is obtained commercially from Entelechon (Germany) to encode a fusion protein which has the following structure, from N- to C-terminus:

10 His N-terminal purification tag (SEQ ID NO: 48),
a 10 asparagine amino acid spacer (SEQ ID NO: 49),
the LC of BoNT/A,
an inter-domain linker with a primary sequence similar to the found in BoNT/A, modified to incorporate the tetra peptide IEGR (SEQ ID NO: 33) which is a substrate for FXa,
the H$_N$ of BoNT/A modified to incorporate a C-terminal Cys,
a Gly-Gly-Gly-Gly-Ser (SEQ ID NO: 50) spacer incorporating an IEGR (SEQ ID NO: 33) peptide sequence at the C-terminus
a 28 amino acid Gastrin releasing peptide modified to incorporate a Cys residue at position 17 in place of the natural Arg and an additional Gly residue at the C-terminus to replace the need for C-terminal amidation (VPLPAGGGTVLTKMYPCGNHWAVGHLMG) (SEQ ID NO: 54).

*E. coli* codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the construction does not result in poor codon utilisation. The DNA was incorporated into a standard cloning vector, for example pCR4, prior to transformation into *E. coli* host. The integrity of the ORF DNA was checked by sequencing. The final ORF is illustrated as SEQ ID 15 and the amino acid sequence of the expression product is illustrated in SEQ ID 16.

Example 14 Method of Treating Patients Suffering from Prostate Cancer

A 56 year old male is suffering from prostate cancer advances to a situation in which androgen-deprivation therapy is no longer sufficient to control the disease. The man is treated by local administration of a composition comprising a TSI of the present invention (in this specific example, a GnRH peptide TM based TSI) into the vicinity of the prostate. The patient's condition is monitored and about 2 months after treatment the physician notes a decrease in tumour size indicating successful treatment with the composition comprising a molecule of the invention.

Example 15 Method of Treating Patients Suffering from Neurogenic Inflammation A 62 year old female diagnosed with rheumatoid arthritis complains of joint stiffness and swelling. A physician determines that the joint stiffness and swelling is due to chronic neurogenic inflammation. The woman is treated by local administration of a composition comprising a TSI of the present invention (in this example, the TSI comprises an opioid TM—parallel examples are run with TSIs comprising nociceptin or dynorphin TMs) in the vicinity of the affected area. The patient's condition is monitored and after about 1-3 days after treatment the woman indicates there is reduced joint stiffness and swelling. At one and three month check-ups, the woman indicates that she continues to have reduced joint stiffness and swelling in the area treated. This reduction in chronic neurogenic inflammation symptoms indicates successful treatment with the composition comprising a molecule of the invention.

Example 16 Method of Treating Patients Suffering from Endometriosis

A 39 year old female presents with pelvic pain due to endometriosis that is not adequately treated with nonsteroidal anti-inflammatory drugs (NSAIDS) and combined estrogen-progestin contraceptives. The physician administers a composition comprising a TSI of the present invention (in this example, the TSI comprises an opioid TM—parallel examples are run with TSIs comprising nociceptin or dynorphin TMs). The patient's condition is monitored and after about 1-3 days after treatment the woman indicates there is reduced pain. At one and three month check-ups, the woman indicates that she continues to have reduced pain and has enhanced freedom of movement. This reduction in symptoms associated with endometriosis indicates successful treatment with the composition comprising a molecule of the invention.

Example 17 Method of Treating Patients Suffering from Overactive Bladder

A 58 year old male complains of increased urinary urgency. A physician diagnosis the patient with overactive bladder having a neurological component involving abnormal neuron activity. The man is treated by injecting urethroscopically a composition comprising a TSI of the present invention (in this example, the TSI comprises an opioid TM—parallel examples are run with TSIs comprising nociceptin or dynorphin TMs). Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that he has a reduced urgency to urinate. At one and three month check-ups, the man indicates that he continues to have a reduced urgency to urinate. This reduction in an overactive bladder symptom indicates successful treatment with the composition comprising a molecule of the invention.

Example 18 Method of Treating Patients Suffering from Neurogenic Inflammation A 62 year old female diagnosed with rheumatoid arthritis complains of joint stiffness and swelling. A physician determines that the joint stiffness and swelling is due to chronic neurogenic inflammation. The woman is treated by local administration a composition comprising a TSI of the present invention in the vicinity of the affected area (in this example, the TSI comprises an opioid TM—parallel examples are run with TSIs comprising nociceptin or dynorphin TMs). The patient's condition is monitored and after about 1-3 days after treatment, and the woman indicates there is reduced joint stiffness and swelling. At one and three month check-ups, the woman indicates that she continues to have reduced joint stiffness and swelling in the area treated. This reduction in chronic neurogenic inflammation symptoms indicates successful treatment with the composition comprising a molecule of the invention. A similar type of local administration of a protein as disclosed in the present specification can be used to treat a patient suffering from chronic neurogenic inflammation associated with any monoarthritis, oligoarthritis, or polyarthritis, such as, e.g., osteoarthritis, juvenile idiopathic arthritis, septic arthritis, a spondyloarthropathy (including ankylosing spondylitis, reactive arthritis (Reiter's syndrome), psoriatic arthritis, enteropathic arthritis associated with inflammatory bowel disease, Whipple disease or Behcet disease), a synovitis, gout, pseudogout, or Still's disease, as well as, a bursitis, a rheumatic fever, or a tenosynovitis. In addition, systemic administration could also be used to administer a composition comprising a molecule of the invention to treat chronic neurogenic inflammation.

The invention claimed is:

1. A nucleic acid encoding a single-chain polypeptide fusion protein comprising:
   (a) a non-cytotoxic protease capable of cleaving a protein of the exocytic fusion apparatus of a target cell;
   (b) a targeting moiety capable of binding to a binding site on the target cell, which binding site is capable of undergoing endocytosis and being incorporated into an endosome within the target cell;
   (c) a translocation domain capable of translocating the protease from within an endosome, across the endosomal membrane, and into the cytosol of the target cell;
   (d) a first cleavage site that is cleavable by a protease, wherein the first cleavage site is located between the non-cytotoxic protease and the translocation domain; and (e) a second cleavage site that is cleavable by a protease, wherein the second cleavage site is located between the translocation domain and the targeting moiety and is not a destructive cleavage site;

wherein the targeting moiety and the translocation domain are capable of forming a covalent linkage such that, following proteolytic cleavage at the second cleavage site, the targeting moiety remains linked to the translocation domain by the covalent linkage.

2. The nucleic acid of claim 1, wherein the translocation domain of the fusion protein is located between the non-cytotoxic protease and the targeting moiety.

3. The nucleic acid of claim 1, wherein the non-cytotoxic protease of the fusion protein is located at the N-terminus of the protein.

4. The nucleic acid of claim 1, wherein the covalent linkage of the fusion protein is a disulfide linkage.

5. The nucleic acid of claim 1, wherein a short polypeptide that provides a secondary polypeptide structure is located between the translocation domain of the fusion protein and the targeting moiety, and wherein the secondary polypeptide structure acts to bring part of the targeting moiety into close proximity to the translocation domain, thereby making formation of the covalent linkage energetically more favorable.

6. The nucleic acid of claim 1, wherein the targeting moiety of the fusion protein comprises first and second domains, and wherein the first and second domains are separated by at most 10 amino acid residues.

7. The nucleic acid of claim 6, wherein the first and second domains of the targeting moiety are derived from ligands to different receptors.

8. The nucleic acid of claim 1, wherein, following cleavage of the fusion protein at the first and second cleavage sites, the targeting moiety of the fusion protein is capable of interacting with the binding site on the target cell (i) via an interaction between an N-terminal domain of the targeting moiety and a domain of the binding site, and, simultaneously, (ii) via an interaction between a C-terminal domain of the targeting moiety and a domain of the binding site.

9. The nucleic acid of claim 1, wherein the targeting moiety of the fusion protein comprises a peptide selected from the group consisting of: a gonadotropin-releasing hormone (GnRH) peptide, an opioid peptide, a beta-endorphin peptide, a bradykinin peptide, a BAM peptide, a nociceptin peptide, a dynorphin peptide, a galanin peptide, an enkephalin peptide, a substance P peptide, a corticotropin-releasing factor (CRF) peptide, a gastrin-releasing peptide (GRP), a Neuromedin B peptide, a bombesin peptide, a gastrin peptide, a CCK peptide, a somatostatin (SST) peptide, a cortistatin (CST) peptide, a growth hormone releasing hormone (GHRH) peptide, a PAR peptide, a parathyroid hormone (PTH) peptide, a vasointestinal peptide (VIP), a beta2 adrenoreceptor agonist peptide, a gastrin-releasing peptide, a calcitonin gene related peptide, a thyroid stimulating hormone (TSH) peptide, an insulin peptide, an insulin-like growth factor peptide, a gonadorelin peptide, a corticotrophin releasing hormone (CRH) peptide, an adrenocorticotropic hormone (ACTH) peptide, and a pituitary adenyl cyclase activating peptide (PACAP).

10. The nucleic acid of claim 1, wherein the non-cytotoxic protease of the fusion protein and the first cleavage site are separated by at most 10 amino acid residues.

11. The nucleic acid of claim 1, wherein the translocation domain of the fusion protein and the first cleavage site are separated by at most 10 amino acid residues.

12. The nucleic acid of claim 1, wherein the translocation domain of the fusion protein and the second cleavage site are separated by at most 10 amino acid residues.

13. The nucleic acid of claim 1, wherein the targeting moiety of the fusion protein and the second cleavage site are separated by at most 10 amino acid residues.

14. The nucleic acid of claim 1, wherein the first and second cleavage sites are capable of being cleaved by the same protease.

15. The nucleic acid of claim 1, wherein the non-cytotoxic protease of the fusion protein is a clostridial neurotoxin L-chain or a fragment thereof.

16. The nucleic acid of claim 1, wherein the translocation domain of the fusion protein is a clostridial neurotoxin $H_N$ domain or a fragment thereof.

17. The nucleic acid of claim 1, wherein the fusion protein encoded by the nucleic acid comprises a purification tag.

18. A DNA vector comprising a promoter, the nucleic acid sequence of claim 1, and a terminator, wherein the nucleic acid sequence is located downstream of the promoter and the terminator is located downstream of the nucleic acid sequence.

19. The complementary DNA strand of the nucleic acid of claim 1.

* * * * *

UNITED STATES PATENT AND TRADEMARK OFFICE
CERTIFICATE OF CORRECTION

PATENT NO. : 10,704,038 B2  
APPLICATION NO. : 16/105203  
DATED : July 7, 2020  
INVENTOR(S) : John Chaddock et al.

Page 1 of 1

It is certified that error appears in the above-identified patent and that said Letters Patent is hereby corrected as shown below:

In the Specification

Column 3, Line 62:

"
$$\text{NH}_2\text{-[protease component]} \overset{\longleftarrow}{\underset{\longleftarrow}{-}} \text{[TM]} \quad \text{[translocation component]-COOH}$$
"

Should read:

$$\text{NH}_2\text{-[protease component]} \quad \overset{\longleftarrow}{\underset{\longleftarrow}{\phantom{xxx}}} \text{[TM]} \quad \text{[translocation component]-COOH}$$

--  --

Signed and Sealed this  
First Day of September, 2020

Andrei Iancu  
*Director of the United States Patent and Trademark Office*